(12) United States Patent
Jewett et al.

(10) Patent No.: US 11,514,627 B2
(45) Date of Patent: Nov. 29, 2022

(54) METHODS AND SYSTEMS FOR DETERMINING AND DISPLAYING PEDIGREES

(71) Applicant: 23andMe, Inc., Sunnyvale, CA (US)

(72) Inventors: Ethan M. Jewett, San Jose, CA (US); Andrew C. Seaman, San Jose, CA (US); Kimberly F. McManus, San Francisco, CA (US); William A. Freyman, Menlo Park, CA (US); Cordell T. Blakkan, San Francisco, CA (US); Adam Auton, Menlo Park, CA (US); Joanna L. Mountain, Menlo Park, CA (US); Susan M. Furest, San Francisco, CA (US); Rachel E. Lopatin, Los Altos, CA (US); Hang Xu, Sunnyvale, CA (US); Hilary M. Vance, Palo Alto, CA (US)

(73) Assignee: 23andMe, Inc., Sunnyvale, CA (US)

( * ) Notice: Subject to any disclaimer, the term of this patent is extended or adjusted under 35 U.S.C. 154(b) by 39 days.

(21) Appl. No.: 16/948,311

(22) Filed: Sep. 11, 2020

(65) Prior Publication Data

US 2021/0082167 A1 Mar. 18, 2021

Related U.S. Application Data

(60) Provisional application No. 62/936,267, filed on Nov. 15, 2019, provisional application No. 62/911,026, (Continued)

(51) Int. Cl.
*G06N 20/00* (2019.01)
*G06T 11/20* (2006.01)
(Continued)

(52) U.S. Cl.
CPC .......... *G06T 11/206* (2013.01); *G06F 3/0481* (2013.01); *G06F 3/04842* (2013.01);
(Continued)

(58) Field of Classification Search
None
See application file for complete search history.

(56) References Cited

U.S. PATENT DOCUMENTS 6,951,721 B2  10/2005  Murphy
7,797,302 B2   9/2010  Kenedy et al.
(Continued)

FOREIGN PATENT DOCUMENTS

EP  0834575 A2  4/1998
EP  1050831 A2  11/2000
(Continued)

OTHER PUBLICATIONS

International Search Report and Written Opinion dated Feb. 8, 2021 issued in Application No. PCT/US20/50582.
(Continued)

*Primary Examiner* — David R Vincent
(74) *Attorney, Agent, or Firm* — Weaver Austin Villeneuve & Sampson LLP; David K. Buckingham

(57) ABSTRACT

The disclosed embodiments concern methods, apparatus, systems and computer program products for determining and displaying pedigrees based on IBD data. Some implementations use a probabilistic relationship model to obtain various likelihoods of various potential relationships based on pairwise IBD data and pairwise age data. Some implementations build large pedigrees by combining smaller pedigrees. Some implementations display pedigree graphs with various features that are informative and easy to understand.

17 Claims, 35 Drawing Sheets
(11 of 35 Drawing Sheet(s) Filed in Color)

Related U.S. Application Data filed on Oct. 4, 2019, provisional application No. 62/900,373, filed on Sep. 13, 2019.

(51) Int. Cl.
- *G06F 3/14* (2006.01)
- *G06T 11/00* (2006.01)
- *G06F 3/04842* (2022.01)
- *G06N 7/00* (2006.01)
- *G06N 5/04* (2006.01)
- *G06F 16/245* (2019.01)
- *G06F 3/0481* (2022.01)

(52) U.S. Cl.
CPC .............. *G06F 3/14* (2013.01); *G06F 16/245* (2019.01); *G06N 5/04* (2013.01); *G06N 7/005* (2013.01); *G06N 20/00* (2019.01); *G06T 11/001* (2013.01); *G06T 11/203* (2013.01); *G06T 2200/24* (2013.01)

(56) References Cited

U.S. PATENT DOCUMENTS

| | | |
|---|---|---|
| 7,818,310 B2 | 10/2010 | Kenedy et al. |
| 7,844,609 B2 | 11/2010 | Kenedy et al. |
| 7,917,438 B2 | 3/2011 | Kenedy et al. |
| 7,933,912 B2 | 4/2011 | Kenedy et al. |
| 7,941,329 B2 | 5/2011 | Kenedy et al. |
| 7,941,434 B2 | 5/2011 | Kenedy et al. |
| 7,957,907 B2 | 6/2011 | Sorenson et al. |
| 8,024,348 B2 | 9/2011 | Kenedy et al. |
| 8,051,033 B2 | 11/2011 | Kenedy et al. |
| 8,055,643 B2 | 11/2011 | Kenedy et al. |
| 8,065,324 B2 | 11/2011 | Kenedy et al. |
| 8,099,424 B2 | 1/2012 | Kenedy et al. |
| 8,108,406 B2 | 1/2012 | Kenedy et al. |
| 8,185,461 B2 | 5/2012 | Kenedy et al. |
| 8,187,811 B2 | 5/2012 | Eriksson et al. |
| 8,200,509 B2 | 6/2012 | Kenedy et al. |
| 8,209,319 B2 | 6/2012 | Kenedy et al. |
| 8,224,821 B2 | 7/2012 | Graham et al. |
| 8,224,835 B2 | 7/2012 | Kenedy et al. |
| 8,255,403 B2 | 8/2012 | Kenedy et al. |
| 8,326,648 B2 | 12/2012 | Kenedy et al. |
| 8,356,023 B2 | 1/2013 | Graham et al. |
| 8,386,519 B2 | 2/2013 | Kenedy et al. |
| 8,428,886 B2 | 4/2013 | Wong et al. |
| 8,452,619 B2 | 5/2013 | Kenedy et al. |
| 8,458,097 B2 | 6/2013 | Kenedy et al. |
| 8,458,121 B2 | 6/2013 | Kenedy et al. |
| 8,463,554 B2 | 6/2013 | Hon et al. |
| 8,510,057 B1 | 8/2013 | Avey et al. |
| 8,543,339 B2 | 9/2013 | Wojcicki et al. |
| 8,589,437 B1 | 11/2013 | Khomenko et al. |
| 8,606,761 B2 | 12/2013 | Kenedy et al. |
| 8,645,343 B2 | 2/2014 | Wong et al. |
| 8,655,899 B2 | 2/2014 | Kenedy et al. |
| 8,655,908 B2 | 2/2014 | Kenedy et al. |
| 8,655,915 B2 | 2/2014 | Kenedy et al. |
| 8,738,297 B2 | 5/2014 | Sorenson et al. |
| 8,786,603 B2 | 7/2014 | Rasmussen et al. |
| 8,788,283 B2 | 7/2014 | Kenedy et al. |
| 8,788,286 B2 | 7/2014 | Kenedy et al. |
| 8,855,935 B2 | 10/2014 | Myres et al. |
| 8,938,439 B2 | 1/2015 | Graham et al. |
| 8,990,250 B1 | 3/2015 | Chowdry et al. |
| 9,031,870 B2 | 5/2015 | Kenedy et al. |
| 9,116,882 B1 | 8/2015 | Macpherson et al. |
| 9,170,992 B2 | 10/2015 | Kenedy et al. |
| 9,213,944 B1 | 12/2015 | Do et al. |
| 9,213,947 B1 | 12/2015 | Do et al. |
| 9,218,451 B2 | 12/2015 | Wong et al. |
| 9,336,177 B2 | 5/2016 | Hawthorne et al. |
| 9,367,663 B2 | 6/2016 | Deciu et al. |
| 9,367,800 B1 | 6/2016 | Do et al. |
| 9,390,225 B2 | 7/2016 | Barber et al. |
| 9,405,818 B2 | 8/2016 | Chowdry et al. |
| 9,582,647 B2 | 2/2017 | Kenedy et al. |
| 9,836,576 B1 | 12/2017 | Do et al. |
| 9,864,835 B2 | 1/2018 | Avey et al. |
| 9,977,708 B1 | 5/2018 | Do et al. |
| 10,025,877 B2 | 7/2018 | Macpherson |
| 10,162,880 B1 | 12/2018 | Chowdry et al. |
| 10,275,569 B2 | 4/2019 | Avey et al. |
| 10,296,847 B1 | 5/2019 | Do et al. |
| 10,379,812 B2 | 8/2019 | Kenedy et al. |
| 10,432,640 B1 | 10/2019 | Hawthorne et al. |
| 10,437,858 B2 | 10/2019 | Naughton et al. |
| 10,516,670 B2 | 12/2019 | Hawthorne et al. |
| 10,572,831 B1 | 2/2020 | Do et al. |
| 10,643,740 B2 | 5/2020 | Avey et al. |
| 10,658,071 B2 | 5/2020 | Do et al. |
| 10,691,725 B2 | 6/2020 | Naughton et al. |
| 10,699,803 B1 | 6/2020 | Do et al. |
| 10,755,805 B1 | 8/2020 | Do et al. |
| 10,777,302 B2 | 9/2020 | Chowdry et al. |
| 10,790,041 B2 | 9/2020 | Macpherson et al. |
| 10,803,134 B2 | 10/2020 | Kenedy et al. |
| 10,841,312 B2 | 11/2020 | Hawthorne et al. |
| 10,854,318 B2 | 12/2020 | Macpherson et al. |
| 10,891,317 B1 | 1/2021 | Chowdry et al. |
| 10,896,233 B2 | 1/2021 | Kenedy et al. |
| 10,936,626 B1 | 3/2021 | Naughton et al. |
| 10,957,455 B2 | 3/2021 | Kenedy et al. |
| 10,991,467 B2 | 4/2021 | Kenedy et al. |
| 10,999,285 B2 | 5/2021 | Hawthorne et al. |
| 11,003,694 B2 | 5/2021 | Kenedy et al. |
| 11,031,101 B2 | 6/2021 | Hon et al. |
| 11,049,589 B2 | 6/2021 | Hon et al. |
| 11,170,047 B2 | 11/2021 | Macpherson et al. |
| 11,170,873 B2 | 11/2021 | Avey et al. |
| 11,171,962 B2 | 11/2021 | Hawthorne |
| 2002/0032687 A1 | 3/2002 | Huff |
| 2003/0135607 A1 | 7/2003 | Bernard et al. |
| 2005/0176031 A1 | 8/2005 | Sears et al. |
| 2005/0287551 A1 | 12/2005 | Gretarsdottir et al. |
| 2006/0100790 A1 | 5/2006 | Downs et al. |
| 2006/0161521 A1 | 7/2006 | Dettinger et al. |
| 2006/0224631 A1 | 10/2006 | Kwon |
| 2006/0236089 A1 | 10/2006 | Cohen |
| 2007/0061424 A1 | 3/2007 | Mattaway |
| 2007/0065017 A1 | 3/2007 | Kotwaliwale et al. |
| 2007/0239538 A1 | 10/2007 | Misra |
| 2007/0266003 A1 | 11/2007 | Wong et al. |
| 2008/0131887 A1 | 6/2008 | Stephan et al. |
| 2008/0172407 A1 | 7/2008 | Sacks |
| 2008/0227063 A1 | 9/2008 | Kenedy et al. |
| 2008/0228043 A1 | 9/2008 | Kenedy et al. |
| 2008/0228410 A1 | 9/2008 | Kenedy et al. |
| 2008/0228451 A1 | 9/2008 | Kenedy et al. |
| 2008/0228677 A1 | 9/2008 | Kenedy et al. |
| 2008/0228698 A1 | 9/2008 | Kenedy et al. |
| 2008/0228699 A1 | 9/2008 | Kenedy et al. |
| 2008/0228700 A1 | 9/2008 | Kenedy et al. |
| 2008/0228701 A1 | 9/2008 | Kenedy et al. |
| 2008/0228702 A1 | 9/2008 | Kenedy et al. |
| 2008/0228704 A1 | 9/2008 | Kenedy et al. |
| 2008/0228705 A1 | 9/2008 | Kenedy et al. |
| 2008/0228706 A1 | 9/2008 | Kenedy et al. |
| 2008/0228708 A1 | 9/2008 | Kenedy et al. |
| 2008/0228722 A1 | 9/2008 | Kenedy et al. |
| 2008/0228753 A1 | 9/2008 | Kenedy et al. |
| 2008/0228756 A1 | 9/2008 | Kenedy et al. |
| 2008/0228757 A1 | 9/2008 | Kenedy et al. |
| 2008/0228765 A1 | 9/2008 | Kenedy et al. |
| 2008/0228766 A1 | 9/2008 | Kenedy et al. |
| 2008/0228767 A1 | 9/2008 | Kenedy et al. |
| 2008/0228768 A1 | 9/2008 | Kenedy et al. |
| 2008/0228797 A1 | 9/2008 | Kenedy et al. |
| 2008/0243843 A1 | 10/2008 | Kenedy et al. |
| 2008/0288886 A1 | 11/2008 | Sherwood et al. |
| 2009/0043752 A1 | 2/2009 | Kenedy et al. |
| 2009/0099789 A1 | 4/2009 | Stephan et al. |

(56) References Cited

U.S. PATENT DOCUMENTS

| | | |
|---|---|---|
| 2009/0112871 A1 | 4/2009 | Hawthorne et al. |
| 2009/0118131 A1 | 5/2009 | Avey et al. |
| 2009/0119083 A1 | 5/2009 | Avey et al. |
| 2009/0119333 A1 | 5/2009 | Sundstrom et al. |
| 2009/0240722 A1 | 9/2009 | Yu et al. |
| 2010/0042438 A1 | 2/2010 | Moore et al. |
| 2010/0063830 A1 | 3/2010 | Kenedy et al. |
| 2010/0063835 A1 | 3/2010 | Kenedy et al. |
| 2010/0063865 A1 | 3/2010 | Kenedy et al. |
| 2010/0070292 A1 | 3/2010 | Kenedy et al. |
| 2010/0070455 A1 | 3/2010 | Halperin et al. |
| 2010/0076950 A1 | 3/2010 | Kenedy et al. |
| 2010/0076988 A1 | 3/2010 | Kenedy et al. |
| 2010/0169262 A1 | 7/2010 | Kenedy et al. |
| 2010/0169313 A1 | 7/2010 | Kenedy et al. |
| 2010/0169338 A1 | 7/2010 | Kenedy et al. |
| 2010/0287213 A1 | 11/2010 | Rolls et al. |
| 2011/0078168 A1 | 3/2011 | Kenedy et al. |
| 2011/0184656 A1 | 7/2011 | Kenedy et al. |
| 2012/0215574 A1* | 8/2012 | Driessnack ......... G06Q 10/0639 705/7.12 |
| 2012/0270190 A1 | 10/2012 | Kenedy et al. |
| 2012/0270794 A1 | 10/2012 | Eriksson et al. |
| 2013/0345988 A1 | 12/2013 | Avey et al. |
| 2014/0006433 A1 | 1/2014 | Hon et al. |
| 2014/0025308 A1* | 1/2014 | Jorde ..................... G16B 30/00 702/19 |
| 2014/0067355 A1 | 3/2014 | Noto et al. |
| 2014/0108527 A1 | 4/2014 | Aravanis et al. |
| 2014/0278138 A1 | 9/2014 | Barber et al. |
| 2015/0112884 A1* | 4/2015 | Ostrovsky ............. G16B 30/10 705/325 |
| 2015/0227610 A1 | 8/2015 | Chowdry et al. |
| 2015/0248473 A1 | 9/2015 | Kenedy et al. |
| 2015/0347566 A1 | 12/2015 | Kenedy et al. |
| 2016/0026755 A1 | 1/2016 | Byrnes et al. |
| 2016/0103950 A1 | 4/2016 | Myres et al. |
| 2016/0171155 A1 | 6/2016 | Do et al. |
| 2016/0277408 A1 | 9/2016 | Hawthorne et al. |
| 2016/0300012 A1 | 10/2016 | Barber et al. |
| 2016/0350479 A1 | 12/2016 | Han et al. |
| 2017/0011042 A1 | 1/2017 | Kermany et al. |
| 2017/0017752 A1 | 1/2017 | Noto et al. |
| 2017/0053089 A1 | 2/2017 | Kenedy et al. |
| 2017/0185719 A1 | 6/2017 | Kenedy et al. |
| 2017/0213127 A1* | 7/2017 | Duncan .................. G16B 40/00 |
| 2017/0220738 A1 | 8/2017 | Barber et al. |
| 2017/0228498 A1 | 8/2017 | Hon et al. |
| 2017/0277827 A1 | 9/2017 | Granka et al. |
| 2017/0277828 A1 | 9/2017 | Avey et al. |
| 2017/0329866 A1 | 11/2017 | Macpherson |
| 2017/0329891 A1 | 11/2017 | Macpherson et al. |
| 2017/0329899 A1 | 11/2017 | Bryc et al. |
| 2017/0329901 A1 | 11/2017 | Chowdry et al. |
| 2017/0329902 A1 | 11/2017 | Bryc et al. |
| 2017/0329904 A1 | 11/2017 | Naughton et al. |
| 2017/0329915 A1 | 11/2017 | Kittredge et al. |
| 2017/0329924 A1 | 11/2017 | Macpherson et al. |
| 2017/0330358 A1 | 11/2017 | Macpherson et al. |
| 2018/0181710 A1 | 6/2018 | Avey et al. |
| 2018/0307778 A1 | 10/2018 | Macpherson |
| 2019/0012431 A1 | 1/2019 | Hon et al. |
| 2019/0034163 A1 | 1/2019 | Kenedy et al. |
| 2019/0034587 A1* | 1/2019 | Anderson ............. G16B 40/20 |
| 2019/0114219 A1 | 4/2019 | Do et al. |
| 2019/0139623 A1 | 5/2019 | Bryc et al. |
| 2019/0206514 A1 | 7/2019 | Avey et al. |
| 2019/0267115 A1 | 8/2019 | Avey et al. |
| 2019/0281061 A1 | 9/2019 | Hawthorne et al. |
| 2019/0384777 A1 | 12/2019 | Naughton et al. |
| 2020/0137063 A1 | 4/2020 | Hawthorne et al. |
| 2020/0210143 A1 | 7/2020 | Kenedy et al. |
| 2020/0372974 A1 | 11/2020 | Chowdry et al. |
| 2021/0020266 A1 | 1/2021 | Freyman et al. |
| 2021/0043278 A1 | 2/2021 | Hon et al. |
| 2021/0043279 A1 | 2/2021 | Hon et al. |
| 2021/0043280 A1 | 2/2021 | Hon et al. |
| 2021/0043281 A1 | 2/2021 | Macpherson et al. |
| 2021/0058398 A1 | 2/2021 | Hawthorne et al. |
| 2021/0074385 A1 | 3/2021 | Hon et al. |
| 2021/0082167 A1 | 3/2021 | Jewett et al. |
| 2021/0166452 A1 | 6/2021 | Jewett et al. |
| 2021/0166823 A1 | 6/2021 | Kenedy et al. |
| 2021/0193257 A1 | 6/2021 | Freyman et al. |
| 2021/0209134 A1 | 7/2021 | Kenedy et al. |
| 2021/0225458 A1 | 7/2021 | Hon et al. |
| 2021/0233665 A1 | 7/2021 | Kenedy et al. |
| 2021/0250357 A1 | 8/2021 | Hawthorne et al. |
| 2021/0313013 A1 | 10/2021 | Hon et al. |
| 2022/0044761 A1 | 2/2022 | O'Connell et al. |
| 2022/0051751 A1 | 2/2022 | Wilton et al. |

FOREIGN PATENT DOCUMENTS

| | | |
|---|---|---|
| EP | 1274020 A2 | 1/2003 |
| EP | 1550958 A2 | 7/2005 |
| EP | 1550959 A2 | 7/2005 |
| EP | 1550960 A1 | 7/2005 |
| WO | WO00/43542 A1 | 7/2000 |
| WO | WO0203252 A1 | 1/2002 |
| WO | WO03027236 A2 | 4/2003 |
| WO | WO2008042232 A2 | 4/2008 |
| WO | WO2008052344 A1 | 5/2008 |
| WO | WO2008117314 A2 | 10/2008 |
| WO | WO2012099890 A1 | 7/2012 |
| WO | WO2016/073953 | 5/2016 |
| WO | WO-2022036178 A1 | 2/2022 |

OTHER PUBLICATIONS

Almudevar, et al., "Estimation of Single-Generation Sibling Relationships Based on DNA Markers" Journal of Agricultural, Biological, and Environmental Statistics, vol. 4, No. 2 (1999) pp. 136-165.

Almudevar, A., "Most Powerful Permutation Invariant Tests for Relatedness Hypotheses Using Genotypic Data" Biometrics 57, Dec. 2001, pp. 1080-1088.

Almudevar, A., "A Bootstrap Assessment of Variability in Pedigree Reconstruction Based on Genetic Markers" Biometrics 57, Sep. 2001, pp. 757-763.

Almudevar, A., "A simulated annealing algorithm for maximum likelihood pedigree reconstruction" Theoretical Population Biology 63 (2003) pp. 63-75.

Aksentijevich et al. "Mutation and Haplotype Studies of Familial Mediterranean Fever Reveal New Ancestral Relationships and Evidence for a High Carrier Frequency with Reduced Penetrance in the Ashkenazi Jewish Population" American Journal of Human Genetics, vol. 64, Mar. 2, 1999, pp. 949-962.

Agarwala, R. et al., "Software for Constructing and Verifying Pedigrees within Large Genealogies and an Application to the Old Order Amish of Lancaster County" Genome Research, Mar. 1998, vol. 8(3), pp. 211-221.

Agarwala, et al., "Anabaptist Genealogy Database" American Journal of Medical Genetics Part C (Semin. Med. Genet.) 121C, (2003) pp. 32-37.

Agarwala, et al., "Towards a Complete North American Anabaptist Genealogy: A Systematic Approach to Merging Partially Overlapping Genealogy Resources" American Journal of Medical Genetics, vol. 86, pp. 156-161, Sep. 10, 1999.

Archive.org [Webpage] "Family Tree DNA History Unearthed Daily" Archive.org, 2007, pp. 1-39. [retrieved on Mar. 4, 2019] <URL:https://web.archive.org/web/20040614162839/http://www.familytreedna>.

Archive.org [Webpage] "Family Tree DNA Tutorial Links" Archive.org, 2005, Oct. 2005, pp. 1-2. [retrieved on Mar. 4, 2019] <URL:https://web.archive.org/web/20051024015952/http://www.familytreedna.com/dna101.html>.

Ball, C. et al., "ancestryDNA—DNA Circles White Paper—2014" AncestryDNA 2014, pp. 1-43.

(56) References Cited

OTHER PUBLICATIONS

Ball, C. et al., [Webpage] "ancestryDNA—Genetic Communities White Paper: Predicting fine-scale ancestral origins from the genetic sharing patterns among millions of individuals" Ancestry.com, Genetic Communitites, pp. 1-28. [retrieved on Jan. 22, 2021] <URL:https://www.ancestry.com/cs/dna-help/communities/whitepaper?_ga=2.31843766.964368407.1611355628-1267188993.1611355628>.

Ball, C. et al., "ancestryDNA—AncestryDNA Matching White Paper—Discovering genetic matches across a massive, expanding genetic database" AncestryDNA, Jul. 15, 2020, pp. 1-34.

Bender, et al., "Least Common Ancestors in Trees and Directed Acyclic Graphs" Journal of Algorithms, vol. 57 (2) (version Oct. 22, 2001) Nov. 2005, pp. 75-94.

Benner, S. et al., "Functional inferences from reconstructed evolutionary biology involving rectified databases—an evolutionarily grounded approach to functional genomics" Research in Microbiology, Mar. 2000, 151(2), pp. 97-106.

Browning, et al., "Identity by Descent Between Distant Relatives: Detection and Applications" Annu. Rev. Genet., Sep. 17, 2012, 46:617-33.

Chapman, C. "A Visual Interface to Computer Programs for Linkage Analysis" American Journal of Medical Genetics, Jun. 1990, vol. 36(2), pp. 155-160.

Carmi, S. et al., "Sequencing and Ashkenazi reference panel supports population-targeted personal genomics and illuminates Jewish and European origins" Nat. Commun. 5, Sep. 9, 2014, 4835. <doi:10.1038/ncomms5835>.

DeCODE Genetics [Webpage] "deCODE genetics, Decoding the Language of Life" Archive.org snapshot Aug. 31, 2000-Apr. 29, 2001, 12pgs. [retrieved on Dec. 31, 2018] <URL:https://web.archive.org/web/20001219153000/http://www.decode.com:8>.

Duerinck, K., [Webpage] "Genealogy Home Page" Archive.org, Jul. 2004, pp. 1-2. <URL:https://web.archive.org/web/20040825103616/http://duerinck.com/> [retrieved on Jan. 24, 2021].

Durand, E. et al. "Reducing Pervasive False-Positive Identical-by-Descent Segments Detected by Large-Scale Pedigree Analysis" Mol. Bio. Evol. 31(8)(2014) pp. 2212-2222.

Elliott, et al., "A Framework for Querying Pedigree Data" Proceedings of the 18th International Conference on Scientific and Statistical Database Management, 2006, pp. 1-10.

Felsenstein, J. (1981) "Evolutionary trees from DNA sequences: A maximum likelihood approach" J. Mol. Evol.17, pp. 368-376.

Fu, W. et al., "Robust Inference of Identity by Descent from Exome-Sequencing Data" The American Journal of Human Genetics 99, Nov. 3, 2016, pp. 1106-1116.

Gauvin, H. et al., "Genome-wide patterns of identity-by-descent sharing in the French Canadian founder population" European Journal of Human Genetics (2014) 22, pp. 814-821.

Graves, K., [Webpage] "The Graves Surname DNA Study" Archive.org, 2005, pp. 1-4. [retrieved Mar. 4, 2019] <URL: https://gravesfa.org/dna.html>.

Gusev, A. et al., "The Architecture of Long-Range Haplotypes Shared within and across Populations" Mol. Biol. Evol. 29(2) (2012) pp. 473-486.

Hammer, M.F. et al., "Jewish and Middle Eastern non-Jewish populations share a common pool of Y-chromosome biallelic haplotypes" PNAS, Jun. 6, 2000, 97(12), pp. 6769-6774.

Helgason et al., "mtDNA and the Islands of the North Atlantic: Estimating the Proportions of Norse and Gaelic Ancestry" American Journal Human Genetics, Mar. 2001, 68(3), pp. 723-737.

Helgason, A. et al., "Estimating Scandinavian and Gaelic Ancestry in the Male Settlers" American Journal of Human Genetics, Sep. 2000, 67(3), pp. 697-717.

Huff, C.D., et al., (2011) "Maximum-likelihood estimation of recent shared ancestry (ERSA)" Genome Research, 21, pp. 768-774.

Jobling, M.A., et al., "The Y chromosome in forensic analysis and paternity testing" International Journal of Legal Medicine, Jun. 1997, 110(3), pp. 118-124.

Kurtcephe, M., "Pedigree Query, Visualization, and Genetic Calculations Tool" Thesis Submitted to Case Western University, Aug. 2012, pp. 1-114.

Kennard, et al., "Improving historical research by linking digital library information to a global genealogical database" JCDL'09, pp. 255-258, Jun. 15-19, 2009, Austin, TX, USA.

Kirkpatrick, B., et al., "Pedigree reconstruction using identity by descent," Comput Biol., doi: 10.1089/cmb.2011.0156, (2010) Nov. 2011, vol. 18(11); pp. 1481-1493.

Kerchner, Jr., C.F., [Webpage] "Kerchner's Genetic Genealogy Y-DNA Surname Project" Archive.org, 2006, pp. 1-17. [retrieved on Mar. 4, 2019] <URL:http://www.kerchner.com/kerchdna.htm>.

Lee, et al. "Fine Mapping of a Gene Responsible for Regulating Dietary Cholesterol Absorpltion; Founder Effects Underlie Cases of Phytosterolemia in Multiple Communities" European Journal of Human Genetics, vol. 9, No. 5, May 2001, pp. 375-384.

Lee, et al., "PedHunter 2.0 and Its Usage to Characterize the Founder Structure of the Old Order Amish of Lancaster County" BMC Medical Genetics 2010, 11:68, pp. 1-13.

Li, Q. "An Algorithm for Finding Optimal Descent Trees in Genealogical Conditional on the Observed Data" Thesis Submitted to Memorial University, Sep. 2010, pp. 1-66.

Loh, et al., "Fast and accurate long-range phasing in a UK Biobank cohort" Nature Genetics, vol. 48, No. 7, Jul. 2016, pp. 811-817.

Loh, et al., "Reference-based phasing using the Haplotype Reference Consortium panel" Nature Genetics vol. 48, No. 11, Nov. 2016, pp. 1443-1450.

Mitosearch [Webpage] "Mitosearch Welcome" Archive.org, 2006, pp. 1-1. [retrieved on Mar. 4, 2019] <URL:https://web.archive.org/web/20051026043528/http://www.mitosearch.org>.

Mumma, D.M., "The Mumma Surname DNA Project" Jan. 20, 2004, pp. 1-20.

Padhukasahasram, B., "Inferring ancestry from population genomic data and its applications" Front. Genet. Jul. 2014, vol. 5, Article 204, pp.

Perego et al., "The Science of Molecular Genalogy" National Genealogical Society Quarterly, V93, Dec. 2005, pp. 245-259.

Ramstetter, et al., "Inferring Identical-by-Descent Sharing of Sample Ancestors Promotes High-Resolution Relative Detection" The American Journal of Human Genetics 103, Jul. 5, 2018, pp. 30-44.

Roper, D.L., "A Roper Y-Chromosome Testing Project" Archive.org, 2005.

Sajantila, et al., "Genes and Languages in Europe: An Analysis of Mitochondrial Lineages" Genome Research, Sep. 1995, 5(1), pp. 45-52.

Stone, et al., "Genetic and Physical Mapping of the McKusick-Kaufman Syndrome" Human Molecular Genetics, 1998, vol. 7, No. 3, pp. 475-481.

Thompson, E. "Identity by Descent Variation in Meiosis; Across Genomes, and in Populations" Genetics, vol. 194, Jun. 2013, pp. 301-326.

Wilson, et al., "Inferences from DNA Data: Population Histories, Evolutionary Processes and Forensic Match Probabilities" J. R. Statist. Soc. A, vol. 166, Part 2, (2003) pp. 155-201.

Wilson, D. Randall, "Graph-based remerging of genealogical databases" Proceedings of the 2001 Family History Technology Workshop (Provo UT, 2001). 2001, pp. 1-4.

Zheng, X. and Weir, B. "Eigenanalysis of SNP data with an identity by descent interpretation" Theoretical Population Biology 107 (2016) pp. 65-76.

U.S. Appl. No. 16/948,311, filed Sep. 11, 2020, Jewett et al.

Kirichenko, A.V., "An Algorithm of Step-by-step Pedigree Drawing," *Russian Journal of Genetics*, vol. 40, No. 10, 2004, pp. 1176-1178.

Ko, A., et al., "Composite Likelihood Method for Inferring Local Pedigrees," PLOS Genetics, https://doi.org/10.1371/journal.pgen.1006963, Aug. 21, 2017, pp. 1-21.

Makinen, V-P., et al., "High-throughput Pedigree Drawing," European Journal of Human Genetics, 2005, vol. 13, pp. 987-989.

Ramstetter, M.D., "Inferring identical by descent sharing of sample ancestors promotes high resolution relative detection," Department of Biological Statistics and Computational Biology, Cornell University, bioRxiv preprint first posted online Jan. 4, 2018, pp. 1-24.

(56) References Cited

OTHER PUBLICATIONS

Staples, J., et al., "PRIMUS: Rapid Reconstruction of Pedigrees from Genome-wide Estimates of Identity by Descent," *The American Journal of Human Genetics*, vol. 95, Nov. 6, 2014, pp. 553-564.
Thiele, H., et al., HaploPainter: a tool for drawing Pedigrees with complex haplotypes, vol. 21 No. 8, 2005, pp. 1730-1732.
Trager, E. H., et al., Madeline 2.0 PDE: A New Program for Local and Web-based Pedigree Drawing, Bioinformatics, vol. 23 No. 14, May 8, 2007, pp. 1854-1856.
Walker II, John Q., "A Node-Positioning Algorithm for General Trees," The University of North Carolina at Chapel Hill, Department of Computer Science, Sep. 1989, pp. 1-32.
International Search Report and Written Opinion dated Feb. 8, 2021, issued in PCT Application No. PCT/US2020/050582.

\* cited by examiner

4 — Choose an ancestor $A_1$ in $C_1$ who has no additional lineages extending from them (up, through their parents, or down through children) besides those extending to the members of $S_1$.

Common ancestor $A_1$ exists?

No → Are all genotyped descendants of members of C1 in S1?

No → Choose the subset $C_1'$ of $C_1$ with descendant leaves only in $S_1$.

Add parental nodes to all members of $C_1'$ until each individual has two parents.

Let C1 now denote the set of all newly-added parents.

Yes → Choose an individual in $C_1$ uniformly at random and call them $A_1$.

5 — Find the set $C_2$ of most recent common ancestor(s) of the set of individuals $S_2$.

Figure 2 (Continued)

```
[
    {
        "id": 1,
        "parent_ids": []
    },
    {
        "id": 2,
        "parent_ids": []
    },
    {
        "id": 12,
        "parent_ids": [1, 2]
    }
]
```

Figure 10

Add information about this grandparent.

First name

| Zhuangquan |

Last name at birth

| Lu |

Married last name

| |

:: Which best describes your grandparent?

○ Female

● Male

:: Is your grandparent living or deceased?

○ Living

● Deceased

:: Place of birth

| Foshan, Guangdong, China |

:: Date of birth

| January ⌄ | 7 ⌄ | 1910 |

:: Place of death

| Guangzhou, Guangdong, China |

:: Date of death

| March ⌄ | 12 ⌄ | 2002 |

Add a photo of your grandparent

| | Browse... |

Figure 30

METHODS AND SYSTEMS FOR DETERMINING AND DISPLAYING PEDIGREES

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

A pedigree refers to the genetic relationships among a group of genetically related individuals. Pedigrees can be used to produce family trees for consumers or genealogists. They can also be used to determine the heritability and genetic models for traits and dis-orders. Pedigree structure can be used to enable or improve genetic-analysis tools such as linkage, family-based association, pedigree-aware imputation, and pedigree-aware phasing.

However, there are many technical challenges in determining pedigrees using genetic data. Manually reconstructing an unknown pedigree with pairwise relationship comparisons requires arduous, error-prone labor. For example, Pemberton et al. manually reconstructed cryptic HapMap3 pedigrees, but the authors encountered inconsistencies they could not resolve by hand. Pemberton, et al. (2010). Inference of unexpected genetic relatedness among individuals in HapMap Phase III. Am. J. Hum. Genet. 87, 457-464. These problems become even more impractical or impossible to solve when the pedigrees are large and numerous.

Computer tools using identity-by-descent (IBD) genetic data to construct pedigrees have been developed to address some of these problems. However, the accuracy, qualities, and efficiencies of available computer tools have many limitations. In various implementations, methods and systems disclosed herein for determining, constructing and visualizing pedigrees provide various advantages and improvements over conventional approaches.

SUMMARY

The disclosed implementations concern methods, apparatus, systems, and computer program products for determining and displaying pedigrees among genetically individuals based on IBD data.

A first aspect of the disclosure provides computer-implemented methods for determining pedigree relationships among a plurality of genetically related individuals.

Another aspect of the disclosure provides systems for determining pedigree relationships among a plurality of genetically related individuals. In some implementations, the system involves a processor and one or more computer-readable storage media having stored thereon instructions for execution on said processor to determine pedigree relationships among a plurality of genetically related individuals.

Another aspect of the disclosure provides a computer program product including a non-transitory machine readable medium storing program code that, when executed by one or more processors of a computer system, causes the computer system to implement the methods above for determining pedigree relationships among a plurality of genetically related individuals.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the invention, reference is made to the following description and accompanying drawings, in which:

FIG. 10 illustrates three entries that can be used in the process for generating the pedigree graph;

FIG. 30 shows an example implementation of displaying a pedigree graph and receiving user input for annotating un-genotyped nodes of the pedigree graph;

DETAILED DESCRIPTION

Figure 1:
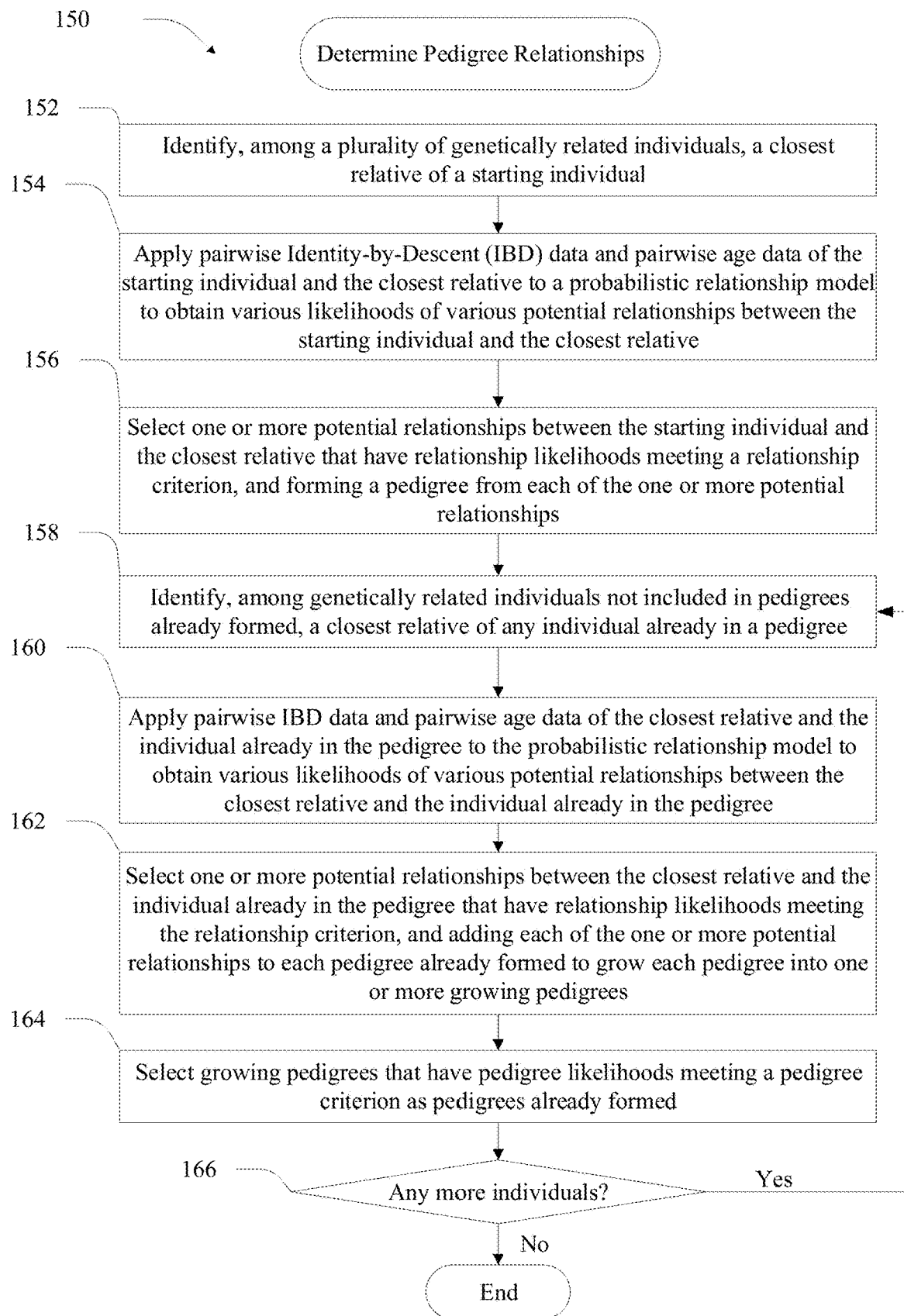
FIG. 1 shows a flowchart illustrating a process for determining pedigree relationships using IBD data and age data according to some implementations.

The disclosure concerns methods, apparatus, systems, and computer program products for determining pedigree relationships among a plurality of genetically related individuals. Various implementations operate on IBD data to perform the disclosed functions. IBD data may be provided in different formats or obtained by various methods. For example, U.S. patent application Ser. No. 16/947,107, entitled: PHASE-AWARE DETERMINATION OF IDENTITY-BY-DESCENT DNA SEGMENTS, filed on Jul. 17, 2020, which is incorporated by reference in its entirety, discloses suitable methods for determining IBD using genotype data.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

The term "plurality" refers to more than one element. For example, the term is used herein in reference to a number of nucleic acid molecules or sequence reads that is sufficient to identify significant differences in repeat expansions in test samples and control samples using the methods disclosed herein.

A DNA segment is identical by state (IBS) in two or more individuals if they have identical nucleotide sequences in this segment. An IBS segment is identical by descent (IBD) in two or more individuals if they have inherited it from a common ancestor without recombination, that is, the segment has the same ancestral origin in these individuals. DNA segments that are IBD are IBS per definition, but segments that are not IBD can still be IBS due to the same mutations in different individuals or recombinations that do not alter the segment.

The terms "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules.

The term "parameter" herein refers to a numerical value that characterizes a physical property. Frequently, a parameter numerically characterizes a quantitative data set and/or a numerical relationship between quantitative data sets. For example, the maximum degree of genetic distance between two genotyped individuals in a pedigree is a parameter of a genetic pedigree model.

The term "based on," when used in the context of obtaining a specific quantitative value, herein refers to using another quantity as input to calculate the specific quantitative value as an output.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

Introduction and Overview

Some existing computer implemented methods use identity-by-descent (IBD) data to estimate pedigrees. One such method for determining a pedigree is PRIMUS. Staples et al. (2014), PRIMUS: Rapid Reconstruction of Pedigrees from Genome-wide Estimates of Identity by Descent, The American Journal of Human Genetics 95, 553-564. PRIMUS uses the total lengths of half and full IBD between pairs of individuals to obtain likelihoods of different relationship types. It then attempts to construct a pedigree for which the product of all pairwise likelihoods induced by the pedigree is greatest. PRIMUS does not use the count of IBD fragments for determining a pedigree and it uses age information only to resolve apparent discrepancies, such as an inferred grandparent being younger than a grandchild or an inferred nephew-uncle pair having an age difference greater than a specified threshold. In general, previous methods do not use age information as part of the likelihood of relationship in constructing pedigrees. In contrast, some implementations disclosed herein use the count of IBD segments and pairwise age differences directly in modeling the likelihoods of relationships. These aspects of the implementations improve the accuracy of relationship estimate.

PRIMUS uses a kernel density estimation to estimate IBD-length distributions. Kernel density estimation is a non-parametric technique that can result in over-fitting data. In contrast, some implementations disclosed herein model distributions of IBD data (e.g., IBD length, number of IBD segments) and age difference data as parametric probability distributions. In various implementations, the probability distributions are modeled as Gaussian distributions, exponential distributions, or Poisson distributions. The parametric approach can provide more reliable estimates by avoiding overfitting the data.

PRIMUS computes likelihoods for only six general categories corresponding to different degrees of relationship:
Parent-child
Full-sibling
Half-sibling, avuncular, grandparental
First-cousin, great-grandparental, great-avuncular, half-avuncular
Distantly related
Unrelated PRIMUS does not compute separate estimates for different relationships within each category (e.g., half siblings, avuncular, and grandparental). This was because relationships within a category could be difficult to distinguish from one another based on genetic data alone. In contrast, methods disclosed herein estimate relationship likelihood for each specific relationship, including each relationship in a same category above. Methods disclosed herein use age data to determine likelihoods of relationships, which is especially helpful for distinguishing relationships with the same coefficient of relationship (e.g. half siblings vs. grandparents).

The coefficient of relationship is a measure of the degree of consanguinity (or biological relationship) between two individuals. With a simplifying assumption of non-consanguineous common ancestors, it can be calculated as:

$$r_{BC} = \sum_p e^{-L(p)},$$

where p enumerates all paths connecting B and C to unique common ancestors, and L(p) is the length of a common-ancestor path p, which may be expressed in generations or meioses through the path. The coefficient of relationship sometimes is also referred to as "average fraction of DNA shared." Table 1 lists various relationships and corresponding coefficients of relationships.

PRIMUS lumps all relationships having the same coefficient of relationship into one category, and relationships with coefficients smaller than 25% cannot be used to generate a pedigree. The disclosed methods herein provide pairwise relationship estimates at many levels beyond a 25% coefficient of relationship. In many applications, relationships up to 15th degree are estimated. This makes it possible to build very large pedigrees with many degrees of relationship.

Conventional methods for determining pedigrees using IBD data do not properly address noise caused by background IBD. For example, some individuals from Ashkenazi Jewish, Mexican, Puerto Rican, and other populations share IBD due to historical bottlenecks, rather than true recent relationships. Such shared IBD constitutes noise in the IBD

TABLE 1

Coefficient of Relationship and Degree of Relationship for Various Relationships

| Degree of Relationship | Relationship | Coefficient of Relationship (r) |
|---|---|---|
| 0 | identical twins; clones | 100% (1) |
| 1 | parent-offspring | 50% ($2^{-1}$) |
| 2 | full siblings | 50% ($2^{-2} + 2^{-2}$) |
| 2 | ¾ siblings or sibling-cousins | 37.5% ($2^{-2} + 2^{-3}$) |
| 2 | grandparent-grandchild | 25% ($2^{-2}$) |
| 2 | half siblings | 25% ($2^{-2}$) |
| 3 | aunt/uncle-nephew/niece | 25% ($2 \cdot 2^{-3}$) |
| 4 | double first cousins | 25% ($4 \cdot 2^{-4}$) |
| 3 | great grandparent-great grandchild | 12.5% ($2^{-3}$) |
| 4 | first cousins | 12.5% ($2 \cdot 2^{-4}$) |
| 6 | quadruple second cousins | 12.5% ($8 \cdot 2^{-6}$) |
| 6 | triple second cousins | 9.38% ($6 \cdot 2^{-6}$) |
| 4 | half-first cousins | 6.25% ($2^{-4}$) |
| 5 | first cousins once removed | 6.25% ($2 \cdot 2^{-5}$) |
| 6 | double second cousins | 6.25% ($4 \cdot 2^{-6}$) |
| 6 | second cousins | 3.13% ($2 \cdot 2^{-6}$) |
| 8 | third cousins | 0.78% ($2 \cdot 2^{-8}$) |
| 10 | fourth cousins | 0.20% ($2 \cdot 2^{-10}$) | data for determining recent relationships in pedigrees. Some implementations herein estimate the level of background IBD by computing the amount of IBD that each person in a group shares with him or herself between two chromosomes. Their IBD data can then be adjusted to remove the background IBD noise. This approach can help to improve the accuracy of pedigree estimates in various populations.

Some implementations described herein also statistically infer whether the IBD carried by an individual in a pedigree is due simply to background IBD. These approaches leverage previously inferred close relatives of such individuals to make these inferences. The methods then exclude such individuals from consideration when inferring degrees of relationship.

When adding a person to a pedigree, PRIMUS checks that the person's maximum likelihood estimated relationship with any person in the pedigree exceeds an initial threshold of 0.3, although this threshold can be adjusted downward over time if a pedigree fails to build properly on the first attempt. The methods disclosed herein do not have such a restriction. Being free of this restriction makes it possible to build larger pedigrees without having to progressively reduce this threshold, saving considerable computational time.

In the process of building pedigrees, PRIMUS does not distinguish among individuals within the same category of relationship. The PRIMUS method builds in stages, first combining all siblings and parent-child pairs, then second degree relatives (half-sibling, avuncular, and grandparent), then third degree relationships (first cousin, half-avuncular, great-avuncular, and great-grandparent). The goal is to combine high-confidence classes of relatives first, although confidence in an estimate can vary within a degree class. In contrast, methods disclosed herein first include a person that is most closely related to any individuals in the pedigree. By giving priority to the close relationship with the highest confidence, the disclosed methods can improve the accuracy of the pedigree estimate.

In adding a person to pedigree, PRIMUS adds the person in all possible relationships regardless of the likelihoods of the relationships. In contrast, the methods disclosed herein add a person to a pedigree in potential relationships that are highly likely. Moreover, the methods disclosed herein exclude low likelihood pedigrees in the process of building pedigrees. These likelihood-based techniques can greatly reduce the pedigree space that needs to be explored without significantly sacrificing accuracy. As a result, it can greatly improve computational speed and efficiency, and reduce memory and CPU loads.

All previous pedigree inference methods, including PRIMUS, attempt to search the full pedigree space. The full search of all possible pedigrees quickly becomes computationally intractable when the number of individuals in the pedigree is moderate or large. This is so even using modern computers. In contrast the methods disclosed herein use a two stage approach. In the first stage, small pedigrees are inferred using approaches that thoroughly search the space of possible pedigrees. In the second stage, small pedigrees are combined into large pedigrees using heuristic methods that greatly reduce the number of pedigrees that must be searched. Without this heuristic second step, it is computationally intractable to build large pedigrees. The methods disclosed herein are the only known methods to use such heuristic approaches and are the only computer-implemented methods capable of building very large pedigrees.

Process for Determining a Pedigree

FIG. 1 shows a flowchart illustrating a process 150 for determining pedigree relationships using IBD data and age data. The process is applicable for determining pedigrees for individual humans or animals, as well as to some other organisms having relevant genetic mechanisms that are analogous to humans and animals. Although persons, people, or humans are referred to in some descriptions, such descriptions are often applicable to other organisms with suitable modifications.

The illustrated process is implemented using a computer system that includes one or more processors and system memory. In many real-world applications, it is not practical or possible to implement these methods in a person's mind or using pen and paper. For pedigrees including a large number of individuals, many types or levels of relationship, or ambiguous data, the computation involved in the process would be too complex to be performed in the human mind.

The methods illustrated here apply IBD data and age data to a probabilistic relationship model to obtain likelihoods of many potential relationships. In each iteration of adding an individual to a pedigree, the number of possible pedigrees grows exponentially. The computational task of determining the likelihood of a single pairwise relationship given IBD data and age data is time-consuming. This computation needs to be performed for tens of relationships in each iteration of growing pedigrees. As the pedigrees grow larger, the computation of a pedigree likelihood becomes impractical to perform by hand.

Process 150 starts by identifying, among the plurality of genetically related individuals, the closest relative of a starting individual. See block 152. In some applications, the starting individual is an individual of interest, such as a consumer who wants to obtain a pedigree or pedigree graph with herself as a focal person. In some implementations, the starting individual is an individual meeting certain genetic relationship criteria, such as a person who has a high average degree of relationship with other individuals being considered. Various methods may be used to determine how closely two individuals are related or the relationship distance between them. For example, IBD data may be used to calculate a coefficient of relationship as explained above.

In various implementations, the plurality of genetically related individuals includes at least 20, 50, 100, 200, 300, 400, or 500 individuals. In some implementations the pedigree can include both genetically related individuals that have been genotyped and those individuals where genotype data is unknown or not available. In some implementations, every pair of individuals in the plurality of genetically related individuals has a total IBD length larger than an IBD threshold. In various implementations, the IBD threshold is 1 centimorgan (cM), 2 cM, 3 cM, 4 cM, 5 cM, 6 cM, 7 cM, 8 cM, 9 cM, 10 cM, 15 cM, 20 cM, 25 cM, 50 cM, 75 cM, 100 cM, 200 cM, or 500 cM. In some implementations, the total IBD length is adjusted by subtracting background IBD from the pairwise IBD data.

Various methods may be used to determine background IBD for a group of individuals or a population of individuals. In some implementations two chromosomes in each pair of one or more pairs of the 22 pairs of somatic chromosomes of the same individual can be compared to identify IBD regions. Two corresponding fragments on a pair of chromosomes are respectively inherited from two parents. Assuming that an individual's two parents are not more consanguineous than unrelated individuals in the population, the IBD amount between the two chromosomes of a pair in the individual provides a good estimate of population background IBD.

In some implementations, the level of background IBD can be inferred by estimating IBD between pairs of individuals assumed to be non-consanguineous.

In some implementations, IBD lengths are adjusted for the background IBD before being used to model or determine the relationship likelihood or pedigree likelihood. In some implementations, IBD lengths are adjusted before being compared to an IBD threshold to determine whether individuals should be included for consideration in a pedigree. In other implementations, pairs of individuals whose IBD sharing levels are inferred to be significantly lower than expected by chance are removed from consideration.

When selecting a next individual to be added to a pedigree, the process considers how closely individuals already included in the pedigrees are related to individuals not yet included. In some implementations, pairwise IBD data between two individuals are used to determine how closely related the two individuals are, or the relationship distance between the two individuals. In some implementations, the relatedness or relationship distance between individuals may be inferred from IBD data using a likelihood expression for the degree of relationship derived using a probabilistic recombination model. Other genetic information and methods may also be used to determine relatedness or relationship distance. In some implementations, relatedness or relationship distance may be measured by meioses on a common ancestor path. In some implementations, relatedness or relationship distance may be expressed as or measured by coefficient of relationship.

Process 150 proceeds to apply pairwise identity by descent (IBD) data and pairwise age data of the starting individual and the closest relative to the probabilistic relationship model to obtain various likelihoods of various potential relationships between the starting individual and the closest relative. In various implementations, the pairwise age data reflect the age difference between two individuals. In some implementations, the pairwise age data are obtained by simple subtraction. In other implementations, other operations may be performed on ages of two individuals, such as division (e.g., to obtain a ratio of two ages) or normalization (e.g., to obtain a z-score).

It is also possible to extrapolate from empirical distributions of age differences between different types of relatives to obtain distributions for relationships that are unobserved empirically. In particular, pairs of relatives sharing third great-grandparental relationships (5 generations) may be unobserved, and therefore, it is not possible to obtain the distribution of the age difference of a third great-grandparental pair empirically. However, the age difference distribution for third great-grandparents can be estimated by computing the mean ($\mu_{PC}$) and variance $\sigma_{PC}^2$ of the age differences among observed parent-child pairs. Then, noting that a third great-grandparental relationship is a string of five statistically independent parent-child relationships, we find that the mean and variance of the age difference distribution for third great-grandparental relationships are $\mu_{5GGP}=5\mu_{PC}$ and $\sigma_{5GGP}^2=5\sigma_{PC}^2$, respectively. This result is obtained by using properties of the means and variances of sums of independently distributed random variables.

Given the IBD data and the pairwise age data of the two individuals, the probabilities or likelihoods of different relationships between the two individuals can be determined using the probabilistic relationship model. Various probabilistic relationship models are further described herein after. See block 154. In some implementations, the pairwise IBD data include the lengths of IBD segments, such as the total or summed length of the IBD segments. In some implementations, the lengths of IBD segments include the length of full IBD segments (IBD2) and/or length of half IBD segments (IBD1). In some implementations, the two types of IBD lengths may be combined. In other implementations, the two IBD segment lengths are kept separate and are modeled by the probabilistic relationship model to have different probability distributions. In some implementations the lengths of half IBD segments (IBD1) are summed and the sum is used to compute the likelihood. Similarly, in some implementations the lengths of full IBD segments (IBD2) are summed and the sum is used to compute the likelihood. In some implementations, the pairwise IBD data also include numbers or counts of IBD segments. Similar to lengths of the two types of IBD segments, the numbers of the two types of IBD segments may be combined or modeled separately.

Given the IBD data and the pairwise age data of the two individuals, the probabilities or likelihoods of different relationships between the two individuals can be determined using the probabilistic relationship model. Various probabilistic relationship models are further described herein after. See block 154. In some implementations, the pairwise IBD data include the lengths of IBD segments, such as the total or summed length of the IBD segments. In some implementations, the lengths of IBD segments include the length of full IBD segments (IBD2) and/or length of half IBD segments (IBD1). In some implementations, the two types of IBD lengths may be combined. In other implementations, the two IBD segment lengths are kept separate and are modeled by the probabilistic relationship model to have different probability distributions. In some implementations the lengths of half IBD segments (IBD1) are summed and the sum is used to compute the likelihood. Similarly, in some implementations the lengths of full IBD segments (IBD2) are summed and the sum is used to compute the likelihood. In some implementations, the pairwise IBD data also include numbers or counts of IBD segments. Similar to lengths of the two types of IBD segments, the numbers of the two types of IBD segments may be combined or modeled separately.

In some implementations, the probabilistic relationship model is a machine learning model obtained by training the model using training data to determine a plurality of parameters of the model, including parameters of probability distributions for various independent/input variables and various relationships. In some implementations, the probabilistic relationship model models the probability distribution of the pairwise IBD as a Gaussian distribution, a Poisson distribution, an exponential distribution, a binomial distribution, a beta binomial distribution, or other distributions suitably determined from prior information. In some implementations, the probabilistic relationship model also models the probability distribution of the pairwise age data for each relationship using one or more of said forms of distributions.

In some implementations, the various potential relationships include more than 10, 20, 30, 40, or 50 different relationships. In various implementations, the various relationships Include relationships of the $0^{th}$, $1^{st}$ and $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, or $15^{th}$ degree or further. In some implementations, the various relationships include relationships of at least 0, 1, 2, 3, 4, 5, 6, 7, 8, 9, 10, 11, 12, 13, 14, 15, 16 or more meioses on a common-ancestor path between the two individuals through a common ancestor. In some implementations, the various relationships include two or more different relationships of the same degree or of the same coefficient of relationship (e.g., half sibling, grandparent, avuncular have a coefficient of relationship of 0.25). So in some implementations, the various relationships include these three relationships as different relationships instead of as a same category of relationship.

Process 150 involves selecting the one or more potential relationships between the starting individual and the closest relative that have relationship likelihoods meeting a relationship criterion, and forming a pedigree from each of the one or more potential relationships. See block 156. In various implementations, different relationship criteria may be used. For example, the relationship criterion may be determined by likelihood ranks or percentile. There may simply be a number of the most likely relationships, e.g., the top 1, 2, 3, 4, 5, 6, 7, 8, 9, 10, or 15 most likely relationships. In other implementations, the relationship criterion is based on a ratio of the candidate relationship likelihood over the maximum relationship likelihood. In some implementations, the ratio is a log likelihood ratio, and the criterion is for the ratio to be larger than a threshold c. In general, the larger the parameter c, the fewer potential relationships are included. By reducing the potential relationships to be used to construct different pedigrees, the process can reduce the number of relationships to be processed. This can increase computational speed and reduce computational load.

Process 150 proceeds to identify, among genetically related individuals not yet included in pedigrees already formed, a closest relative of any individual in the formed pedigrees. See block 158.

Process 150 further involves applying pairwise IBD data and pairwise age data of the closest relative and the individual already in the formed pedigrees to the probabilistic relationship model to obtain various likelihoods of various potential relationships between the closest relative and the individual already in the pedigrees. See block 160.

Process 150 then proceeds to select one or more potential relationships between the closest relative and the individual already in the pedigrees that have relationship likelihoods meeting the relationship criterion. The process also adds each of the one or more potential relationships with the individual already in the pedigrees to grow each pedigree into one or more growing pedigrees. See block 162.

Process 150 further involves selecting growing pedigrees that have pedigree likelihoods meeting a pedigree criterion. In some implementations, a pedigree likelihood can be obtained by aggregating the likelihood of all the relationships in a pedigree, such as summing the log likelihoods of the pairwise relationships in a pedigree. In some implementations, the pedigree criterion is met when a ratio of the candidate pedigree likelihood over a maximum pedigree likelihood is larger than or equal to a threshold value d. In various implementations, d=0.1, 0.2, 0.3, 0.4, 0.5, 0.6, 0.7, 0.8, 0.9, or 1.0. In other implementations, d=$1/100,000$, $1/500,000$, $1/1,000,000$, $1/2,000,000$, $1/4,000,000$, or the like. In some implementations, the pedigree criterion may also be determined by pedigree likelihood ranks or percentile. Similar to the parameter c above, as d gets larger, fewer pedigrees are included for pedigree building. By increasing the value of d, one can increase computational speed and reduce CPU or memory load for exploring potential pedigrees.

Process 150 then decides whether there are more individuals to be considered for adding to the pedigrees. See block 166. If so, the process loops back to block 158 to identify another closest relative of any individual already in the pedigree. In some implementations, the process continues the loop until all individuals of the plurality of genetically related individuals have been identified as a closest relative or excluded from the pedigrees according to particular exclusion criteria.

FIG. 1 shows that process 150 ends when no more individuals need to be considered. But in some applications, a number of pedigrees having high likelihoods are selected for further downstream processing. In some implementations, the pedigree having the highest likelihood is stored in memory. In some implementations, the data of the pedigree having the highest pedigree likelihood are retrieved and used to generate a pedigree graph, such as those described hereinafter. The pedigree graph then can be displayed on a display device.

Combining Smaller Pedigrees into Larger Pedigrees

Figure 2:
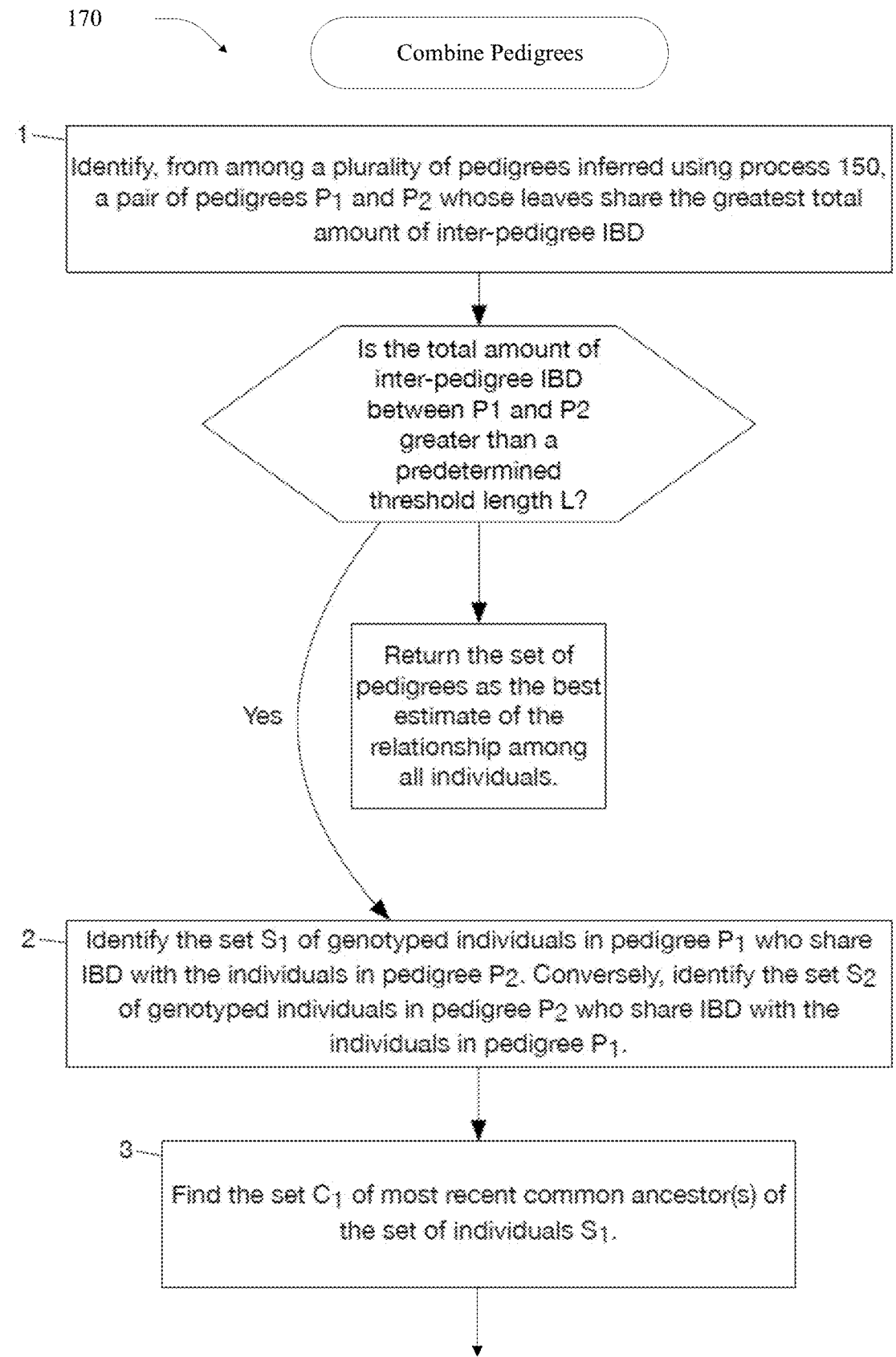
FIG. 2 shows parts 1-4 of a flow chart illustrating process 170 that can be used to combine smaller pedigrees into a larger one according to some implementations.
Figure 2:
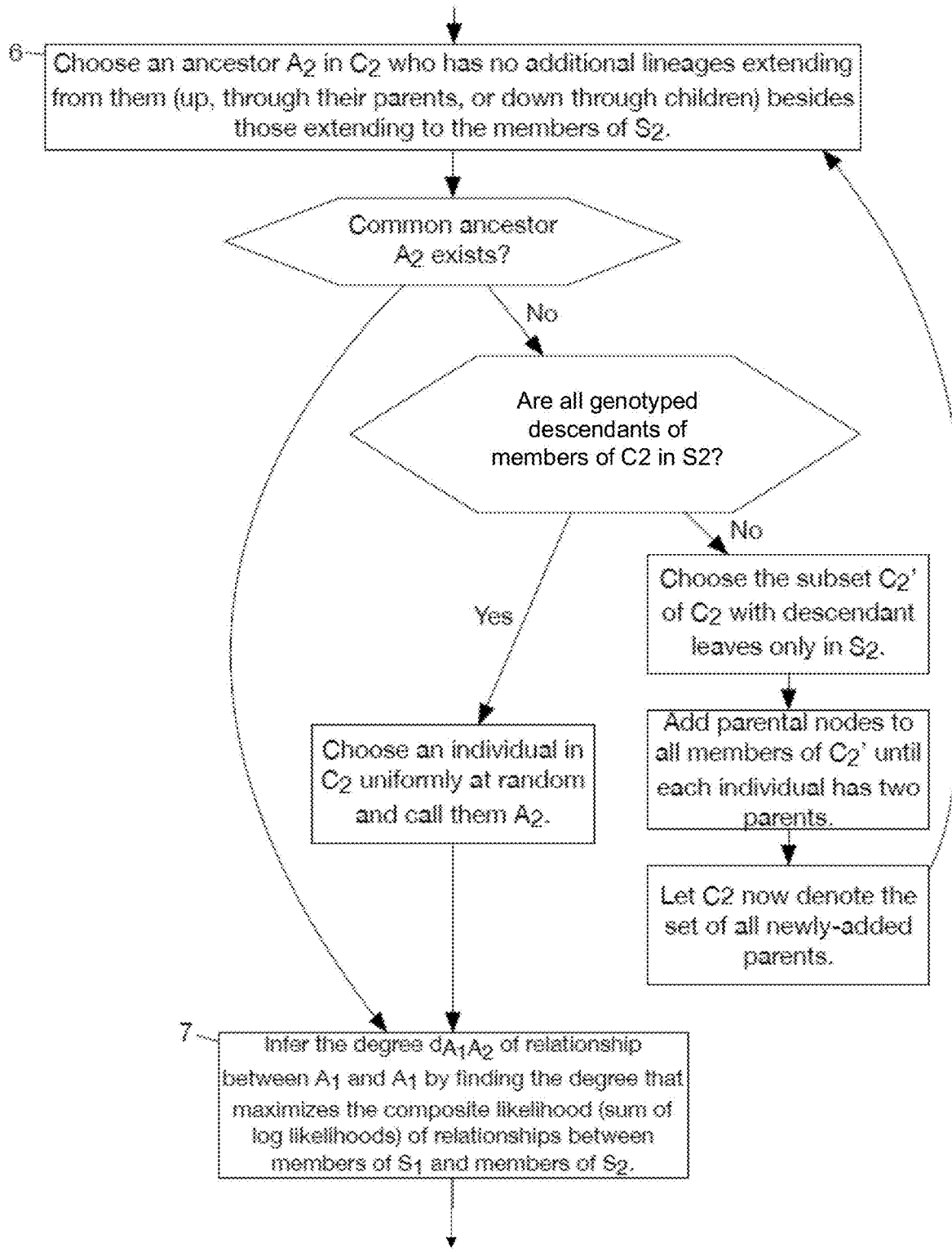
Figure 2:
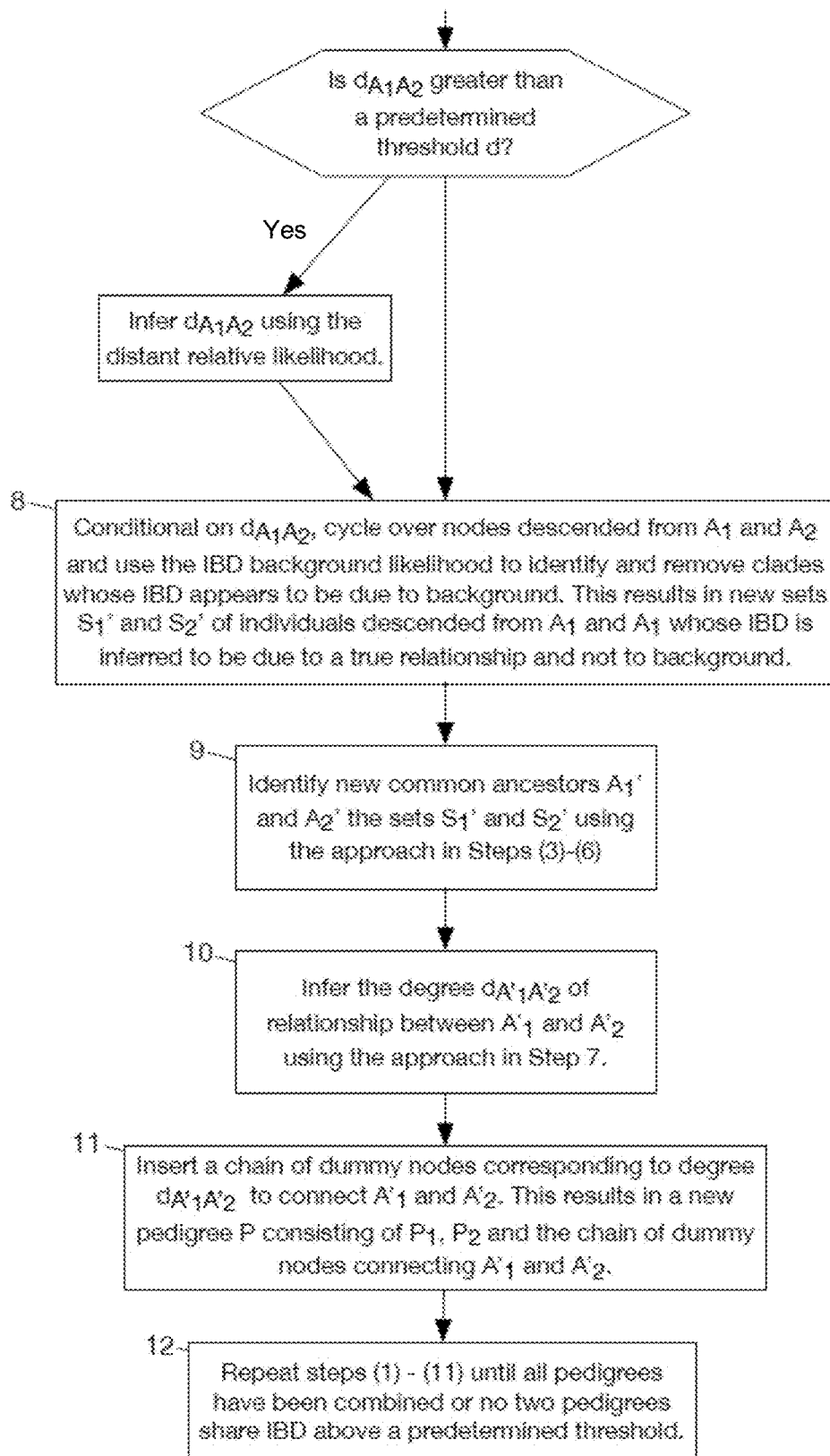

Pedigrees created using process 150 can be combined into even larger pedigrees. FIG. 2 shows a flow chart in four parts illustrating process 170 that can be used to combine smaller pedigrees into a larger one according to some implementations. Combining pedigrees has two primary uses. First, combining multiple pedigrees together makes it possible to create very large pedigrees connected by common ancestors many generations in the past. For such large pedigrees, it is not possible to add a single individual at a time to grow the pedigree as is done in process 150 and the PRIMUS method. This is because the amount of IBD shared between two distantly-related people decreases quickly in their degree of relationship. For example, relatives with more than 10 degrees of separation have a high probability of sharing no detectable IBD segments, especially if segments with lengths similar to background IBD are ignored or removed from the analysis.

Combining smaller pedigrees into larger pedigrees makes it possible to leverage all IBD segments observed between the smaller pedigrees when inferring the degree of relationship between individuals. This is because it is more likely that some individual in a small pedigree shares IBD with some individual in a related pedigree, even if not all cross-pedigree pairs of individuals share IBD. FIG. 2 show four parts of process 170 of using IBD segments in close relatives to improve the inference of relationship degrees.

Methods that combine pedigrees are also computationally much faster than methods that add one individual at a time. The reason for this is that, the amount of IBD shared between a single unplaced individual and a set of genotyped individuals in a pedigree is often consistent with many possible relationships. Consequently, it is necessary to consider many ways of placing the new individual, which is computationally slow. In contrast, when combining two pedigrees, the IBD shared between individuals in the first pedigree and individuals in the second pedigree is larger than the amount shared with any single individual, providing additional information about the way in which the two pedigrees are related. As a result, there are fewer highly likely ways in which the pedigrees can be related, reducing the number of combinations that must be explored and considerably increasing the speed of computation. Combining pedigrees makes it computationally possible to infer pedigrees that are much larger than pedigrees that are computationally tractable for PRIMUS or methods that must search many possible pedigree configurations.

Figure 3:
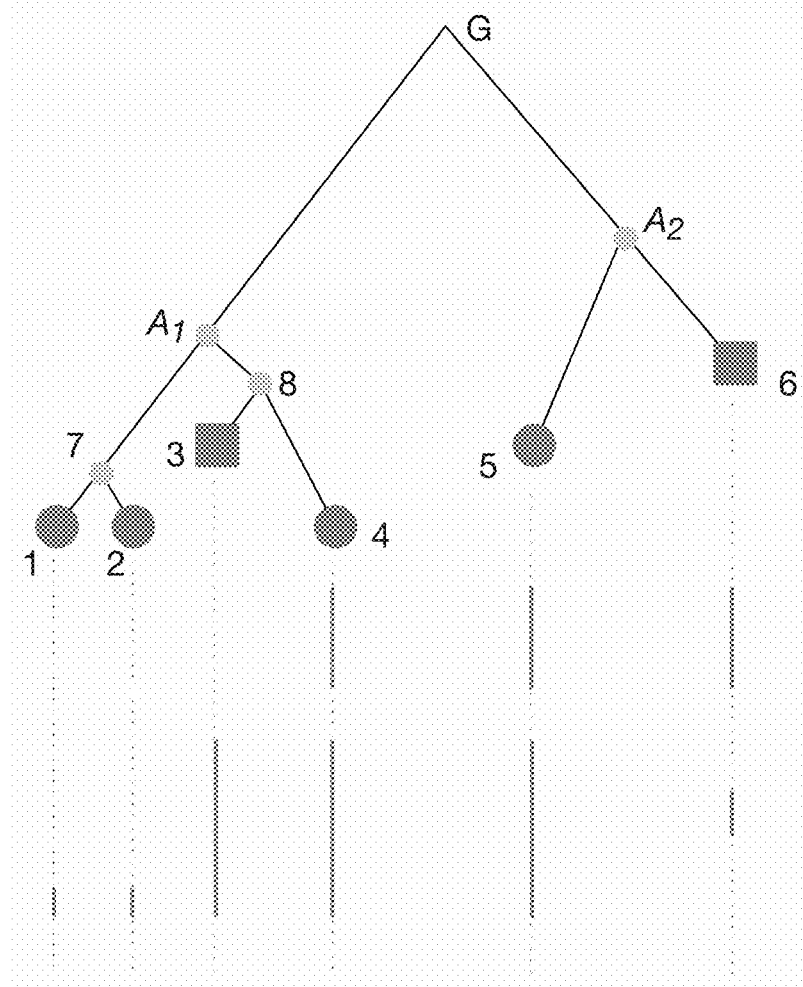
FIG. 3 shows the use of closely-related individuals for identifying background IBD. Genotyped individuals are represented by large shaded squares and circles. Vertical solid lines indicate regions where genotyped individuals in the left pedigree share IBD with individuals in the right pedigree. A most recent common ancestor, G, has transmitted genetic material to both pedigrees, some of which is shared as IBD among the left and right pedigrees. Note that there can be either one or two most recent common ancestors, G, and that the observed segments are the union of all segments inherited from these ancestors. White dots on genotyped individuals indicate the set of genotyped individuals with no direct genotyped ancestors. White dots on ungenotyped individuals indicate the most recent common ancestors transmitting the segments to the genotyped individuals. Dashed lines in the pedigree indicate the induced tree whose branch lengths correspond to degrees of relationship among individuals. All observed IBD segments in the left pedigree were inherited through their common ancestor $A_1$ and all IBD segments in the right pedigree were inherited through their common ancestor $A_2$. The number of meioses separating $A_1$ and $A_2$ from a common ancestor, G, are $d_{A_1,G}$ and $d_{A_2,G}$. The arrow and horizontal bar indicate a specific position along the genome at which one considers the pattern of presence and absence of IBD.

Another reason to combine pedigrees is that background IBD can be detected more effectively. When comparing a single pair of individuals, it is difficult to detect whether the IBD they share is due to background or to a recent relationship. However, by examining the amount of IBD shared among all genotyped or sequenced close relatives of a pair of individuals, it becomes easier to determine when observed IBD is background IBD. FIG. 3 shows the use of closely-related individuals for identifying background IBD.

Referring to FIG. 2, process 170 for combining smaller pedigrees into larger pedigrees begins by first considering a set of pedigrees inferred using various methods such as process 150 shown in FIG. 1. In some implementations the set of pedigrees can be obtained from another appropriate source besides process 150. Process 170 then proceeds by computing the total amount of IBD shared between each pair of pedigrees. The total amount of IBD between two pedigrees, $P_1$ and $P_2$, is found by merging the IBD segments between all pairs of individuals $i_1$ and $i_2$ such that $i_1$ is in $P_1$ and $i_2$ is in $P_2$.

Process 170 proceeds by identifying the two smaller pedigrees, $P_1$ and $P_2$, that share the greatest amount of IBD. See Box 1. These will be the next pair of pedigrees that will be combined. To combine pedigrees $P_1$ and $P_2$, the set $S_1$ of individuals in $P_1$ who share IBD with individuals in $P_2$ are then identified. Conversely, the set $S_2$ individuals in $P_2$ who share IBD with individuals in $P_1$ are identified. See box 2. Process 170 then proceeds by identifying a common ancestor $A_1$ of the set $S_1$ (box 3 and box 4) and a common ancestor $A_2$ of the set $S_2$ (box 5 and box 6). These common ancestors are identified using the small pedigree structures that were previously inferred using methods such as shown in process 150.

The degree of relationship between common ancestors $A_1$ and $A_2$ is then inferred. See box 7. In some implementations of the method, the degree of relationship between $A_1$ and $A_2$ is inferred by considering a degree of relationship between $A_1$ and $A_2$ and attaching $A_1$ and $A_2$ by a chain of dummy nodes reflecting this degree to create a combined pedigree P comprising $P_1$, $P_2$, and the newly-formed chain of dummy nodes. The log likelihood of this pedigree can then be computed as the sum over all pairwise log likelihoods among genotyped individuals in P. Process 170 considers many different possible degrees between $A_1$ and $A_2$ and forms a new pedigree P for each degree. The degree between $A_1$ and $A_2$ is then inferred as the degree that yields the pedigree P with the highest sum of pairwise log likelihoods.

In other implementations, the degree of relationship between $A_1$ and $A_2$ is inferred using a version of the DRUID estimator (M. D. Ramstetter, S. A. Shenoy, T. D. Dyer, D. M. Lehman, J. E. Curran, R. Duggirala, J. Blangero, J. G. Mezey, and A. L. Williams. Inferring identical-by-descent sharing of sample ancestors promotes high-resolution relative detection. Am. J. Hum. Genet., 103:30-44, 2018) that we generalize to the case of pedigrees with arbitrary outbred topologies. This generalized estimator of the degree between $A_1$ and $A_2$ is discussed in Section Distant Relatives Likelihood.

In some implementations, process 170 involves identifying individuals in the sets $S_1$ and $S_2$ whose observed IBD is likely due to background IBD. The IBD observed in these individuals can lead to biased estimates of the degree of relatedness between ancestors $A_1$ and $A_2$ and, more importantly, it can lead to the incorrect identification of $A_1$ and $A_2$, themselves.

The way in which background IBD can contribute to the mis-identification of $A_1$ and $A_2$ is shown in FIG. 3.

In FIG. 3, individuals 1 and 2 share a small amount of IBD with individuals 5 and 6. Because individuals 1 and 2 have approximately the same degree of relationship to 5 and 6 as individuals 3 and 4, it appears that the amount of IBD that 1 and 2 share with 5 and 6 is much lower than that expected by chance. Thus, one can ignore the IBD in 1 and 2 when connecting pedigrees $P_1$ and $P_2$.

Ignoring the IBD in individuals 1 and 2 will not only lead to a different inferred degree between $P_1$ and $P_2$, it also affects the choice of $A_1$. In particular, if individuals 1 and 2 are unrelated to individuals 5 and 6, then the correct common ancestor in pedigree $P_1$ to whom one will connect $A_2$ is individual 8. In some implementations, process cycles over nodes descended from $A_1$ and $A_2$ and identifies nodes whose descendants share significantly less IBD than expected, conditional on the current estimate of the pedigrees $P_1$ and $P_2$, the choice of ancestors $A_1$ and $A_2$, and the degree of relationship between $A_1$ and $A_2$. See box 8. In other implementations, the processing of these nodes is optional.

To determine whether the amount of observed IBD in the descendants of node $n_1$ below $A_1$ is statistically significantly lower than that expected by chance, some implementations consider the set $N_1$ of genotyped descendants of $n_1$ and compute the total merged amount of IBD shared between individuals in $N_1$ and all nodes in $S_2$. The process then uses the likelihood described hereinafter in the Distant Relatives Likelihood section to evaluate whether the total merged length of IBD is significantly lower than that expected by chance. If the amount of IBD is lower than expected, the descendants $N_1$ of node $n_1$ are removed from $S_1$. The aforementioned approach is then used to identify and remove nodes below of $A_2$ whose descendants have an amount of IBD that is significantly lower than that expected by chance. Some implementations cycle through nodes descended from $A_1$ and $A_2$ by repeat consideration of shared IBD of the nodes described above until the amount of IBD in all the remaining descendant nodes of $A_1$ and $A_2$ is not significantly different from that expected by chance.

In some implementations, process 170 identifies a new pair of common ancestors $A'_1$ and $A'_2$ of the reduced sets $S'_1$ and $S'_2$, where $S'_1$ consists of the individuals in $S_1$ who remain after removing individuals whose IBD is inferred to be due to background IBD. Similarly, $S'_2$ consists of the individuals in $S_2$ who remain after removing individuals whose IBD is inferred to be due to background IBD. See box 9. In some implementations, the operation shown in box 9 is optional, and downstream processes are performed on $A_1$ and $A_2$. Process 170 then computes the degree of relatedness between $A'_1$ and $A'_2$ using the likelihood described in the Distant Relatives Likelihood section. See box 10. The process then attaches $A'_1$ to $A'_2$ by a string of dummy ancestral nodes. This step yields a new pedigree P comprised of small pedigrees $P_1$ and $P_2$, and the dummy nodes connecting $A'_1$ and $A'_2$. See box 11.

Process 170 can repeat operations covered by box 1 through box 11 and interim boxes until all small pedigrees have been combined into a single pedigree, or until no two small pedigrees share an amount of merged IBD greater than a predetermined threshold.

Distant Relatives Likelihood

Likelihoods computed among pairs of individuals provide high accuracy for inferring the degree of relatedness when the degree is relatively small. However, the amount of IBD shared between two individuals decreases exponentially in their degree of relatedness, resulting in very little information for inferring degrees between distant relatives. In fact, an approach similar to that of Felsenstein's (1973) tree pruning algorithm. Felsenstein, J. (1981). Evolutionary trees from DNA sequences: A maximum likelihood approach. J. Mol. Evol. 17, 368-376.

Consider one of ancestor G's two alleles at a single locus and let $O_i$ be a random variable describing the event that a copy of the allele is transmitted to descendant i and is observed. One sets $O_i=1$ if the allele is observed in individual i and $O_i=0$ if it is not observed. The probability $Pr(O_i=1)$ can be computed by conditioning on whether G's allele was observed in a recent ancestor of individual i.

Figure 4:
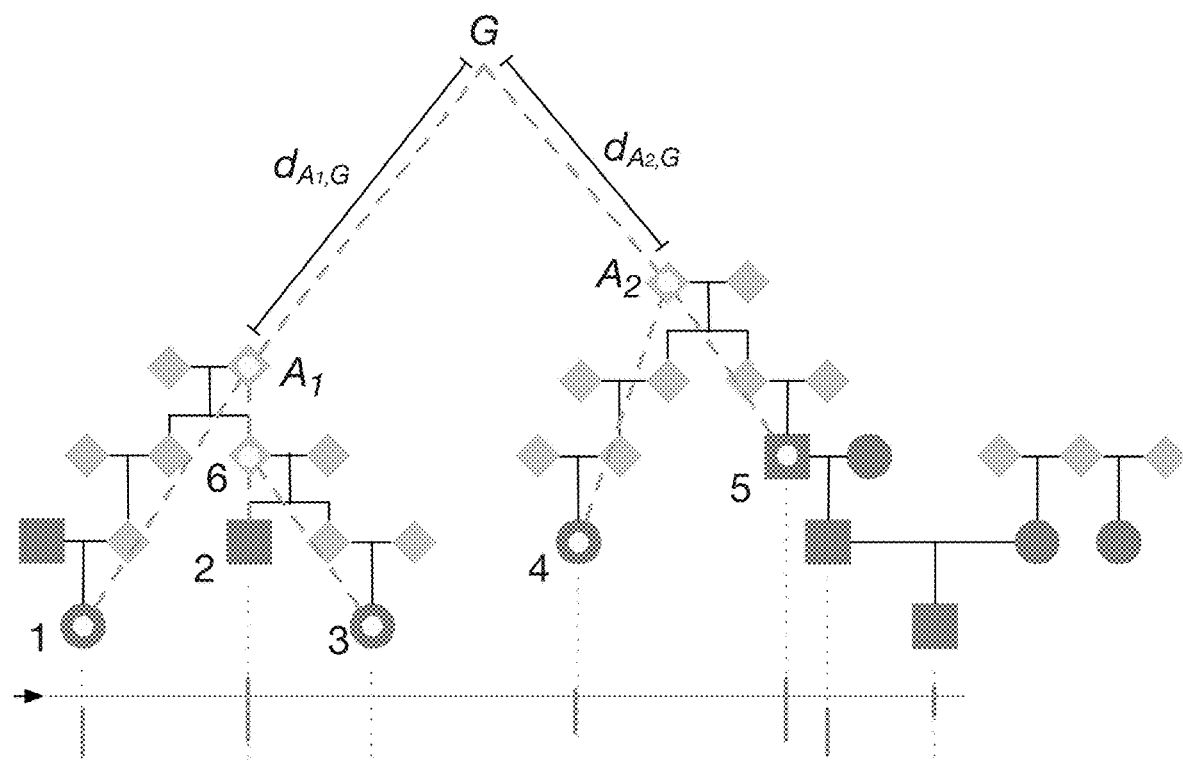
FIG. 4 illustrates the utility of considering IBD segments among groups of individuals rather than pairwise IBD. Genotyped individuals are represented by large shaded squares and circles. Vertical solid lines indicate IBD segments shared between the genotyped descendants of $A_1$ and the genotyped descendants of $A_2$.

Consider the tree relating a set of genotyped individuals with no genotyped direct ancestors and their respective most recent common ancestors (dashed orange lines and red dots in FIG. 4). Let a(i) denote the parent node of node i in this tree. For example, in the tree in FIG. 4, $a(1)=A_1$, $a(6)=A_1$, $a(2)=6$, $a(3)=6$, $a(4)=A_2$, $a(5)=A_2$, $a(A_1)=G$ and $a(A_2)=G$. It follows:

$$Pr(O_i = 1) = Pr(O_i = 1 \mid O_{a(i)} = 1)Pr(O_{a(i)} = 1) + Pr(O_i = 1 \mid O_{a(i)} = 0)Pr(O_{a(i)} = 0) \quad (1)$$
$$= Pr(O_i = 1 \mid O_{a(i)} = 1)Pr(O_{a(i)} = 1)$$
$$= 2^{-d_{i,a(i)}} Pr(O_{a(i)} = 1),$$

and $$Pr(O_i = 0) = Pr(O_i = 0 \mid O_{a(i)} = 1)Pr(O_{a(i)} = 1) + Pr(O_i = 0 \mid O_{a(i)} = 0)Pr(O_{a(i)} = 0) \quad (2)$$
$$= [1 - 2^{-d_{i,a(i)}}]Pr(O_{a(i)} = 1) + Pr(O_{a(i)} = 0),$$

there can be a sizable probability that distant relatives will share no IBD segments at all, especially if IBD segments below a threshold are discarded to reduce the rate of observation of false positives.

When inferring the degree of relatedness between two distant relatives, it is helpful to leverage information from IBD segments shared among close relatives of these two individuals. FIG. 4 illustrates the utility of considering IBD segments among groups of individuals rather than pairwise IBD when the degree of relatedness is not small. In particular, individuals 3 and 4 in FIG. 4 share no IBD segments. Thus, one cannot infer their degree of relatedness without prior knowledge. However, if close relatives of 3 and close relatives of 4 have been genotyped and local pedigree structures have been previously inferred, one can use the IBD in close relatives of 3 and close relatives of 4 to estimate their degree of relationship.

Practitioners have developed a likelihood estimator of the pairwise degree of relatedness between the common ancestors $A_1$ and $A_2$ of two sets of genotyped individuals. To do this, practitioners derive the probability of the observed pattern of IBD shared among descendants of $A_1$ and $A_2$, given the degree $d=d_{A_1,G}+d_{A_2,G}$ separating $A_1$ and $A_2$ from their most recent common ancestor, G. Note that there can be more than one most recent common ancestor, G. There are two such individuals, G, if $A_1$ and $A_2$ are descended from a single ancestral couple and there is one most recent common ancestors if $A_1$ and $A_2$ are descended from a pair of half siblings.

FIG. 4 shows an IBD segment shared among genotyped individuals in two small pedigrees. If one considers a fixed position on the genome, the segment will be present in some individuals at the position and absent in others. The probability of the observed presence and absence pattern can be computed recursively by conditioning on whether the segment was observed in the ancestor of each individual using where $d_{i,a(i)}$ is the number of meioses separating individual i from their ancestor a(i). In the final lines of Equations (1) and (2), one has used the fact that the probability that an allelic copy is transmitted in one meiosis is ½.

Equations (1) and (2) establish a recursion for computing the probability of an observed presence and absence pattern from a given ancestral allelic copy at a single base of the genome. Defining $$p_{i,0} \equiv Pr(O_i=0), p_{i,1} \equiv Pr(O_i=1), \quad (3)$$

one can express the recursion compactly as $$p_{i,0} = [1-2^{-d_{i,a(i)}}]p_{a(i),1} + p_{a(i),0},$$

$$p_{i,1} = 2^{-d_{i,a(i)}} p_{a(i),1}, \quad (4)$$

with the base conditions $p_{g,0}=0$ and $p_{g,1}=1$ for $g \in G$. The probability of an observed IBD sharing pattern $\{O_1, \ldots, O_k\}$ across k leaf nodes can then be computed recursively using Equation (4).

Equation (4) allows one to compute the expected total length $T_{1,2}$ of the genome that is covered by an IBD segment between some descendant of $A_1$ and some descendant of $A_2$. In other words, this is the length of IBD one would obtain if one merged all observed IBD segments between descendants of $A_1$ and $A_2$. The expected fraction of the genome that is observed IBD between descendants of $A_1$ and $A_2$ is given by the probability that an ancestral allele copy at a locus in G is passed down to at least one descendant of $A_1$ and at least one descendant of $A_2$.

Let $\mathcal{N}_1$ be a set of nodes descended from $A_1$ and let $\mathcal{N}_2$ be a set of nodes descended from $A_2$. In some implementations, $\mathcal{N}_1$ and $\mathcal{N}_2$ are the sets of genotyped nodes below $A_1$ and $A_2$. Let $D_1$ denote the event that a copy of the allele from G is observed in at least one descendant in $\mathcal{N}_1$. Then, given that the ancestral allele copy was passed to $A_1$, the probability of the event $D_1{}^c$ that no copy was passed to any node in $\mathcal{N}_1$ is $$Pr(D_1{}^c|O_{A_1}=1)=Pr(O_n=0 \text{ for } n\in \mathcal{N}_1|O_{A_1}=1), \quad (5)$$

which can be computed using the recursion in Equation (4) with the base conditions $p_{A_1,0}=0$ and $p_{A_1,1}=1$. The equivalent probability $Pr(D_2{}^c|O_{A_2}=1)$ that a particular allelic copy from G is not observed in any node in $\mathcal{N}_2$, given that $A_2$ inherited the copy is computed in the same way.

The probability that the allelic copy was observed in some member of $\mathcal{N}_1$ and in some member of $\mathcal{N}_2$ is then $$Pr(D_1, D_2) = Pr(D_1, D_2 | O_{A_1} = 1, O_{A_2} = 1)Pr(O_{A_1} = 1)Pr(O_{A_2} = 1) \quad (6)$$

$$= Pr(D_1 | O_{A_1} = 1)Pr(D_2 | O_{A_1} = 1)Pr(O_{A_1} = 1)Pr(O_{A_2} = 1)$$

$$= [1 - Pr(D_1^c | O_{A_1} = 1)][1 - Pr(D_2^c | O_{A_2} = 1)]Pr(O_{A_1} = 1)Pr(O_{A_2} = 1)$$

$$= [1 - Pr(D_1^c | O_{A_1} = 1)][1 - Pr(D_2^c | O_{A_2} = 1)]2^{-(d_{A_1,G}+d_{A_2,G})},$$

where $Pr(D_1{}^c|O_{A_1}=1)$ and $Pr(D_2{}^c|O_{A_2}=1)$ are computed using the recursion (4) and Equation (5).

If $A_1$ and $A_2$ had exactly one common ancestor with one allele to transmit, then Equation (6) would be the fraction of the genome in which we expect to find some IBD segment shared between some member of $\mathcal{N}_1$ and some member of $\mathcal{N}_2$. However, we must now account for the fact that each common ancestor of $A_1$ and $A_2$ in G carries two allelic copies and that there can be either one or two such common ancestors.

Let $|G|$ denote the number of common ancestors of $A_1$ and $A_2$, each of which carries two alleles at the locus of interest. The probability that a specific one of these $2|G|$ alleles is not observed IBD between the descendants of $A_1$ and $A_2$ is $1-Pr(D_1, D_2)$ and the probability that none of them results in an observed IBD segment is $[1-Pr(D_1, D_2)]^{2|G|}$. Therefore, the probability $Pr(\mathcal{I}_{1,2})$ that one of the $2|G|$ ancestral alleles results in an observed IBD segment between some descendant of $A_1$ and some descendant of $A_2$ is $$Pr(\mathcal{I}_{1,2})=1-[1-Pr(D_1,D_2)]^{2|G|}. \quad (7)$$

One can use the probability $Pr(\mathcal{I}_{1,2})$ to obtain an approximate likelihood of the total length $T_{1,2}$ of IBD observed between descendants of $A_1$ and $A_2$. The mean of this distribution is simply the expected length of the genome in a state of IBD between the two clades, which is $$E[T_{1,2}]=Pr(\mathcal{I}_{1,2})L_{genome}. \quad (8)$$

An approximation of the variance of $T_{1,2}$ is derived by noting that the length of a patch of IBD can be approximated as the maximum length of $|\mathcal{N}_1|\times|\mathcal{N}_2|$ different IBD segments, where $\mathcal{N}_i$ is the set of genotyped nodes below ancestor $A_i$ at locus m in which the IBD segment is observed. This approximation comes from conceptualizing IBD shared among the $|\mathcal{N}_1|$ IBD segment carrying descendants of $A_1$ and the $|\mathcal{N}_2|$ IBD segment carrying descendants of $A_2$ as $|\mathcal{N}_1|\times|\mathcal{N}_2|$ independent segments with a single point at which all segments overlap. The length of the merged segment to one side of this focal point then has a distribution given by the maximum of $|\mathcal{N}_1|\times|\mathcal{N}_2|$ exponential random variables whose means depend on the degree of separation between the corresponding pairs of leaf individuals.

This approximation is a simplification of the IBD sharing pattern because the segments are not truly independent and need not overlap at a single point. Moreover, under this approximation, the length of the merged segment would actually be the maximum over sums of identically distributed random variables, representing the sum of the length of a segment to the right of the center point and the length of the segment to the left. However, one need not be overly concerned with these drawbacks of the conceptualization because the goal is to obtain an accurate, yet simple approximation of the variance of the distribution. One may also assume that no member of $\mathcal{N}_i$ is the direct ancestor of another member of the set, which holds in practice if we drop all individuals from $\mathcal{N}_i$ who are descended from others.

The length, $\ell_{i,j}$, of an IBD segment between leaf nodes i and j can be modeled as an exponentially distributed random variable with mean length $\mu_{ij}=L_{genome}/d_{i,j}R$, where $d_{i,j}$ is the degree of relationship between them and R is the expected number of recombination events, genome wide, in one meiosis. This approximation is due to Huff, C. D., Witherspoon, D. J., Simonson, T. S., Xing, J., Watkins, W. S., Zhang, Y., Tuohy, T. M., Neklason, D. W., Burt, R. W., Guthery, S. L., Woodward, S. R., and Jorde, L. B. (2011). Maximum-likelihood estimation of recent shared ancestry (ERSA). Genome Research, 21, 768-774. When the length of the genome is expressed in centimorgans (cM), the expected number of recombination events in the genome is $L_{genome}/100$. Thus, the expected length in cM of an IBD segment between individuals i and j separated by $d_{i,j}$ meioses is $\mu_{ij}=100/d_{i,j}$.

Let $L_{1,2}$ denote a random variable describing the length of the segment formed by merging all segments at a given locus m, between descendants of $A_1$ and $A_2$. If the lengths of all segments at this locus were independent, their merged length would have a distribution given (approximately) by the maximum over independent exponentially distributed random variables with means $\{\mu_{i,j}\}_{i\in\mathcal{N}_1, j\in\mathcal{N}_2}$.

Then we have $L_{1,2}=\max(\{\ell_{i,j}\}_{i\in\mathcal{N}_1, j\in\mathcal{N}_2})$. Under this condition, the cumulative density function (CDF) $F_L(\ell;\mathcal{N}_1,\mathcal{N}_2)$ of L is $$F_{L_{1,2}}(\ell;\mathcal{N}_1, \mathcal{N}_2) \quad (9)$$

$$= Pr(L_{1,2} < \ell;\mathcal{N}_1, \mathcal{N}_2)$$

$$= Pr(\ell_{i,j} < \ell, \text{ for } i \in \mathcal{N}_1, j \in \mathcal{N}_2)$$

$$= \prod_{i\in\mathcal{N}_1}\prod_{j\in\mathcal{N}_2} Pr(\ell_{i,j} < \ell)$$

$$= \prod_{i\in\mathcal{N}_1}\prod_{j\in\mathcal{N}_2} (1 - e^{-\lambda_{i,j}\ell})$$

-continued
$$= 1 - \sum_{i \in N_1, j \in N_2} e^{-\lambda_{i,j}\ell} + \sum_{i,u \in N_1, j,v \in N_2} e^{-(\lambda_{i,j}+\lambda_{u,v})\ell}(1 - \delta_{(i,j),(u,v)}) -$$
$$\sum_{i,u,w \in N_1, j,v,z \in N_2} e^{-(\lambda_{i,j}+\lambda_{u,v}+\lambda_{z,w})\ell}(1 -$$
$$\delta_{(i,j),(u,v)})(1 - \delta_{(i,j),(z,w)})(1 - \delta_{(u,v),(z,w)}) + \ldots,$$

where $\delta_{(a,b),(c,d)}$ is the Kronecker delta between tuples (a, b) and (c, d), which is equal to one when (a, b)=(c, d) and zero, otherwise.

The sets $\mathcal{N}_1$ and $\mathcal{N}_2$ are, themselves, random variables. Summing over all sets $\mathcal{N}_1$ and $\mathcal{N}_2$, one obtains $$F_{L_{1,2}}(\ell) = \sum_{\mathcal{N}_1, \mathcal{N}_1} F_{L_{1,2}}(\ell; \mathcal{N}_1, \mathcal{N}_2) Pr(\mathcal{N}_1) Pr(\mathcal{N}_2), \quad (10)$$

where the probabilities $Pr(\mathcal{N}_1)$ and $Pr(\mathcal{N}_2)$ are probabilities of observing IBD in the sets of leaf nodes below $A_1$ and $A_2$ and can be computed using the recursion in Equation (4).

Over the length of the genome, the number $N_{1,2}$ of IBD segments between the descendants of $A_1$ and $A_2$ is approximately Poisson distributed with mean $Pr(\mathcal{I}_{1,2})L_{genome}/$ $E[L_{1,2}]$, where $\mathcal{I}_{1,2}$ is the event that IBD is observed between some individual in $\mathcal{N}_1$ and some individual in $\mathcal{N}_2$. This rate comes from the fact that the average total amount of the genome in a patch of IBD is $Pr(\mathcal{I}_{1,2})L_{genome}$ while the average length of any given segment is $E[L_{1,2}]$. Thus, there are approximately $Pr(\mathcal{I}_{1,2})L_{genome}/E[L_{1,2}]$ patches of IBD in the genome, on average. When the lengths of IBD are relatively short and far apart, which they are when the degree between $A_1$ and $A_2$ is large, this is a reasonable approximation. This is precisely the regime in which the distribution in Equation (20) is most useful.

The total length $T_{1,2}$ of merged IBD among the descendants of $A_1$ and $A_2$ is then $$T_{1,2} = \sum_{n=1}^{N_{1,2}} L_{1,2}. \quad (11)$$

One can derive the variance of $T_{1,2}$ using the law of total variance as $$\text{Var}(T_{1,2}) = E[\text{Var}(T_{1,2} \mid N_{1,2})] + \text{Var}(E[T_{1,2} \mid N_{1,2}]) \quad (12)$$
$$= E[N_{1,2}\text{Var}(L_{1,2})] + \text{Var}(N_{1,2}E[L_{1,2}])$$
$$= E[N_{1,2}]\text{Var}(L_{1,2}) + \text{Var}(N_{1,2})E[L_{1,2}]^2.$$

Note that because $N_{1,2} \sim \text{Poisson}(Pr(\mathcal{I}_{1,2})L_{genome}/E[L_{1,2}])$, one obtains $$E[N_{1,2}] = \text{Var}(N_{1,2}) = Pr(\mathcal{I}_{1,2})L_{genome}/E[L_{1,2}]. \quad (13)$$

So Equation (12) simplifies to $$\text{Var}(T_{1,2}) = \frac{Pr(I_{1,2})L_{genome}}{E[L_{1,2}]}[\text{Var}(L_{1,2}) + E[L_{1,2}]^2] \quad (14)$$
$$= Pr(I_{1,2})L_{genome}\frac{E[L_{1,2}^2]}{E[L_{1,2}]},$$

where the fact that $\text{Var}(X)=E[X^2]-E[X]^2$ has been used.

It remains to find $E[L_{1,2}]$ and $E[L_{1,2}^2]$. Using the cumulative density function (CDF) of $L_{1,2}$ in Equation (10) and the fact that $E[X^m]=m! \int_{\mathbb{R}} x^{m-1}[1-F_X(x)]dx$, one obtains $$E_{\mathcal{N}_1, \mathcal{N}_2}[L_{1,2}^m] = m! \int_{\ell=0}^{\infty} x^{m-1}[1 - F_{L_{1,2}}(\ell; \mathcal{N}_1, \mathcal{N}_2)]d\ell \quad (15)$$
$$= \sum_{i \in N_1, j \in N_2} \int_{\ell=0}^{\infty} m!\ell^{m-1}e^{-\lambda_{i,j}\ell}d\ell - \sum_{i,u \in N_1, j,v \in N_2} \int_{\ell=0}^{\infty} m!\ell^{m-1}e^{-(\lambda_{i,j}+\lambda_{u,v})\ell}d\ell +$$
$$\sum_{i,u,w \in N_1, j,v,z \in N_2} \int_{\ell=0}^{\infty} m!\ell^{m-1}e^{-(\lambda_{i,j}+\lambda_{u,v}+\lambda_{z,w})\ell}d\ell + \ldots$$
$$= \sum_{i \in N_1, j \in N_2} \frac{m!}{\lambda_{i,j}^m} - \sum_{i,u \in N_1, j,v \in N_2} \frac{m!}{(\lambda_{i,j}+\lambda_{u,v})^m} +$$
$$\sum_{i,u,w \in N_1, j,v,z \in N_2} \frac{m!}{(\lambda_{i,j}+\lambda_{u,v}+\lambda_{z,w})^m} + \ldots$$

where the integrals in Equation (15) can be evaluated by noting that they are essentially expressions for the moments of exponential random variables with parameters $\lambda_i$, $(\lambda_i+\lambda_j)$, $(\lambda_i+\lambda_j+\lambda_k)$, etc.

Thus, one can use Equation (15) to compute $$E[L_{1,2}^m] = \sum_{\mathcal{N}_1, \mathcal{N}_1} E_{\mathcal{N}_1, \mathcal{N}_2}[L_{1,2}^m]Pr(\mathcal{N}_1, \mathcal{N}_2), \quad (16)$$

where $Pr(\mathcal{N}_1, \mathcal{N}_2)$ is the probability of observing IBD segments at the leaves $\mathcal{N}_1$ and $\mathcal{N}_2$, and is obtained using the recursion in Equation (4). Equation (16) is then used into Equation (14) to obtain the variance of $T_{1,2}$.

In practice, it is too computationally demanding to compute the sums in Equation (16) because the terms $E_{\mathcal{N}_1, \mathcal{N}_2}[L_{1,2}]$, $E_{\mathcal{N}_1, \mathcal{N}_2}[L_{1,2}^2]$, and $Pr(\mathcal{N}_1, \mathcal{N}_2)$ are not fast to compute in large quantities. However, the probabilities $Pr(\mathcal{N}_1, \mathcal{N}_2)$ can be computed quickly, making it possible to find the most likely sets of leaf nodes, $\hat{\mathcal{N}}_1$ and $\hat{\mathcal{N}}_2$, with observed IBD. Thus, in some implementations one can use an approximation in which it is assumed that the most likely IBD pattern has been observed and one computes $$E[L_{1,2}{}^m] \approx E_{\hat{\mathcal{N}}_1, \hat{\mathcal{N}}_2}[L_{1,2}{}^m]. \tag{17}$$

The assumption used in this approximation is that most patterns of observed IBD at the leaves are unlikely compared with the most likely pattern and that most high-likelihood patterns of IBD will yield similar moments $E[L_{1,2}{}^m]$.

Equation (17) can then be used to obtain an approximation of the variance of $T_{1,2}$ as $$\mathrm{Var}(T_{1,2}) \approx Pr(I_{1,2}) L_{genome} \frac{E[L_{1,2}^2]}{E[L_{1,2}]}, \tag{18}$$

where $L_{1,2}$ is the length of any given IBD segment between $A_1$ and $A_2$ formed by merging all IBD segments between leaf nodes in $A_1$ and $A_2$ that overlap one another.

If the segments, $L_{1,2}$ were each exponentially distributed, then $T_{1,2}$ would have a gamma distribution. In practice, a gamma distribution is an accurate approximation for the distribution of $T_{1,2}$, given that the length $T_{1,2}$ is greater than zero, so one can approximate the distribution of $T_{1,2}$ by $$T_{1,2}|T_{1,2}>0 \sim \mathrm{Gamma}(k_{1,2}, \theta_{1,2}),$$

where $k_{1,2}$ and $\theta_{1,2}$ are found by matching the mean and variance of the gamma distribution with $E[T_{1,2}]$ and $\mathrm{Var}(T_{1,2})$. Thus, one obtains $$T_{1,2}\Big|T_{1,2}>0 \sim \mathrm{Gamma}\left(\frac{E[L_{1,2}]^2}{\mathrm{Var}(L_{1,2})}, \frac{\mathrm{Var}(L_{1,2})}{E[L_{1,2}]}\right), \tag{19}$$

where $E[L_{1,2}]$ and $E[L_{1,2}^2]$ are given by Equation (15).

If every IBD segment has some length, one can assume that $T_{1,2}$ is only identically zero when there are no IBD segments. The distribution of the number of segments can be modeled as a Poisson random variable with mean $E[N_{1,2}]$ equal to the expected number $N_{1,2}$ of merged segments shared between $\mathcal{N}_1$ and $\mathcal{N}_2$. The probability that there are no segments is then $e^{-E[N_{1,2}]}$. Thus, one has the approximation $$f_{T_{1,2}}(t_{1,2}) \approx \begin{cases} \frac{t_{1,2}^{k-1}}{\Gamma(k)\theta^k} e^{-t_{1,2}/\theta}(1-e^{-E[N_{1,2}]}) & \text{if } t_{1,2} > 0 \\ e^{-E[N_{1,2}]} & \text{if } t_{1,2} = 0. \end{cases} \tag{20}$$

where $k=E[L_{1,2}]^2/\mathrm{Var}(L_{1,2})$ and $\theta=\mathrm{Var}(L_{1,2})/E[L_{1,2}]$.

Estimators of Distant Relationships

A maximum likelihood estimator of the degree between $A_1$ and $A_2$ can be obtained by determining the degree $d_L(A_1, A_2)$ between $A_1$ and $A_2$ for which value of the distribution in Equation (20) is maximized. This gives the likelihood estimator $$d_L(A_1, A_2) = \mathrm{argmax}_d f_{T_{1,2}}(t_{1,2}; d). \tag{21}$$

One can also use Equation (5) to obtain a generalized version of the DRUID estimator of Ramstetter, M. D., Shenoy, S. A., Dyer, T. D., Lehman, D. M., Curran, J. E., Duggirala, R., Blangero, J., Mezey, J. G., and Williams, A. L. (2018). Inferring identical-by-descent sharing of sample ancestors promotes high-resolution relative detection. Am. J. Hum. Genet. 103, 30-44. The generalized estimator can provide fast estimates of the degree without the need to evaluate Equation (21). Using the approach of Ramstetter et al., the total length of IBD shared between $A_1$ and $A_2$ can be estimated as the total length of IBD shared between $\mathcal{N}_1$ and $\mathcal{N}_2$, divided by the total fraction of genetic material $A_1$ and $A_2$ are expected to pass to their descendants. The fraction $f_i$ of the genome of $A_i$ passed to their descendants $\mathcal{N}_i$, is given by $$f_i = 1 - Pr(O_n = 0 \text{ for } n \in \mathcal{N}_i | O_{A_i} = 1) \tag{22}$$

Thus, an estimate $\widehat{IBD}(A_1, A_2)$ of the amount of IBD shared between $A_1$ and $A_2$ is $$\widehat{IBD}(A_1, A_2) = \frac{IBD(\mathcal{N}_1, \mathcal{N}_2)}{f_1 f_2} \tag{23}$$

Using the expression $\hat{\phi} = \widehat{IBD}(A_1, A_2)/4L_{genome}$ for the kinship coefficient when all IBD is of type 1, one obtains the generalized DRUID estimator $$d_D(A_1, A_2) = d: \frac{1}{2^{d+3/2}} \leq \frac{IBD(\mathcal{N}_1, \mathcal{N}_2)}{4 f_1 f_2 L_{genome}} < \frac{1}{2^{d+1/2}}, \tag{24}$$

are the ones used for the DRUID estimator presented in Ramstetter et al. Thus, one obtains a version of the DRUID estimator that can be applied to general outbred pedigrees.

Likelihood for Identifying Background IBD

Individuals with no recent relationship can share small segments of IBD by chance, especially in populations with recent or severe bottlenecks. This kind of IBD is referred to as background IBD and it poses a considerable challenge to accurate pedigree inference. Previous methods have addressed background IBD by various approaches. For example, the authors of the ERSA method present an approach for modeling the distribution of background IBD among unrelated individuals and then performing a likelihood ratio test to determine whether the IBD shared between a new pair of individuals is significantly different from background; Huff, C. D., Witherspoon, D. J., Simonson, T. S., Xing, J., Watkins, W. S., Zhang, Y., Tuohy, T. M., Neklason, D. W., Burt, R. W., Guthery, S. L., Woodward, S. R., and Jorde, L. B. (2011). Maximum-likelihood estimation of recent shared ancestry (ERSA). Genome Research, 21, 768-774. This approach requires a background distribution of IBD and it requires testing each pair of individuals separately. The difficulty with detecting background IBD between each pair of individuals separately is that it can result in throwing out many pairs of individuals whose levels of IBD sharing are near background, even when those pairs are truly related. Improved power for detecting background IBD can be obtained by leveraging the information inherent in previously-inferred pedigree structures to infer background IBD for sets of multiple individuals at the same time.

Practitioners take an approach to identifying background IBD in which they consider the information contained in IBD sharing patterns across multiple individuals to determine when IBD is background and when it is due to true recent ancestry. In particular, we consider the problem in which all of the IBD observed in an individual is either background IBD, or true IBD due to a recent relationship.

To illustrate the approach, consider the IBD sharing pattern shown in FIG. 3. Individuals 3 and 4 share relatively large amounts of IBD with 5 and 6, compared with the amount shared between {1, 2} and {5, 6}. If 1 and 2 were much more distantly related to 5 and 6 than are 3 and 4, one might not consider the amount of IBD they share with 5 and 6 to be unusually small. However, because 1, 2, 3, and 4 have similar degrees of relatedness to 5 and 6, the amount of IBD shared by 1 and 2 appears to be unusually low. If one can say that the amount of IBD shared below node 7 is smaller than expected by chance, then one can assume that the IBD observed in 1 and 2 is background IBD and remove these nodes from consideration when connecting the left and right pedigrees.

One can test for background IBD through a series of hypothesis tests. Given that IBD is observed between two sets of nodes, $\mathcal{N}_1$ and $\mathcal{N}_2$, suppose that the putative common ancestors $A_1$ and $A_2$ through which the IBD was inherited are the most recent common ancestors of $\mathcal{N}_1$ and $\mathcal{N}_2$, respectively. One can then consider each of the descendant nodes immediately below $A_1$ in turn (e.g., 7 and 8 in FIG. 3) and ask whether the amount of observed IBD below the node is much lower or higher than expected by chance, given the degree between $A_1$ and $A_2$ inferred using all the descendant nodes below $A_1$.

All nodes that reject the null hypothesis of this test are dropped and the ancestral node is reset to be the common ancestor of all remaining IBD-carrying nodes. For example, if one detected that the clade below node 7 in FIG. 3 had much lower IBD than expected by chance, one would drop node 7 and its descendants from consideration and set the true common ancestor relating the two pedigrees to be node 8. One would then iteratively repeat this procedure until no nodes are dropped. One would then then repeat the procedure for the nodes immediately below $A_2$.

Let $\mathcal{C}_n$ denote the set of children of node n. To test whether the IBD observed below a child node $c \in \mathcal{C}_{A_1}$ is background IBD, consider the null hypothesis $H_0$ that the observed IBD below the node is real, and ask whether this hypothesis is rejected in favor of the alternative hypothesis $H_1$ that the IBD is background. Background IBD can either be lower than the expected true amount of IBD (as in the example in FIG. 3), or it can be higher than expected if, for example, the true branch between nodes 7 and $A_1$ in FIG. 3 were very long and the expectation is that no true IBD is observed. Therefore, the hypothesis test must be two-tailed to account for both scenarios.

Under the null hypothesis $H_0$, it is assumed that the IBD observed is real and we assume that the degree $d_{H_0}(A_1, A_2)$ between $A_1$ and $A_2$ is the maximum likelihood estimate: $d_{H_0}(A_1, A_2) = d_L(A_1, A_2)$, or the generalized DRUID estimate: $d_{H_0}(A_1, A_2) = d_D(A_1, A_2)$. One can then perform the following test Reject $H_0$ at level $\alpha$ if:

$$Pr(T_{c,A_2} \leq t_{c,A_2}; d_{H_0}(A_1,A_2)) < \alpha/2, \text{ or}$$

$$Pr(T_{c,A_2} \geq t_{c,A_2}; d_{H_0}(A_1,A_2)) < \alpha/2, \quad (25)$$

where $T_{c,A_2}$ is the random variable describing the observed amount of IBD between descendants of c and descendants of $A_2$ with observed value $t_{c,A_2}$. The distribution of $T_{c,A_2}$ is given by Equation (20). It is reasonable to be conservative when dropping background IBD so that true relationships are called as background IBD only a small fraction of the time. Thus, in practice, we take $\alpha$ to be small, such as $\alpha = 10^{-4}$.

Determining when Ancestral Branches are Unrelated

One difficulty in constructing large pedigrees is determining the ancestors through which two sets of gentoyped individuals are related. A simple fundamental question is whether two lineages are both on the maternal side of an individual, both on the paternal side, or on opposite parental sides. Without genotyped parents, the side through which a lineage passes can be difficult to determine, although sex chromosomes and mitochondrial haplotypes can be used to resolve the parent of origin in some cases.

Figure 5:
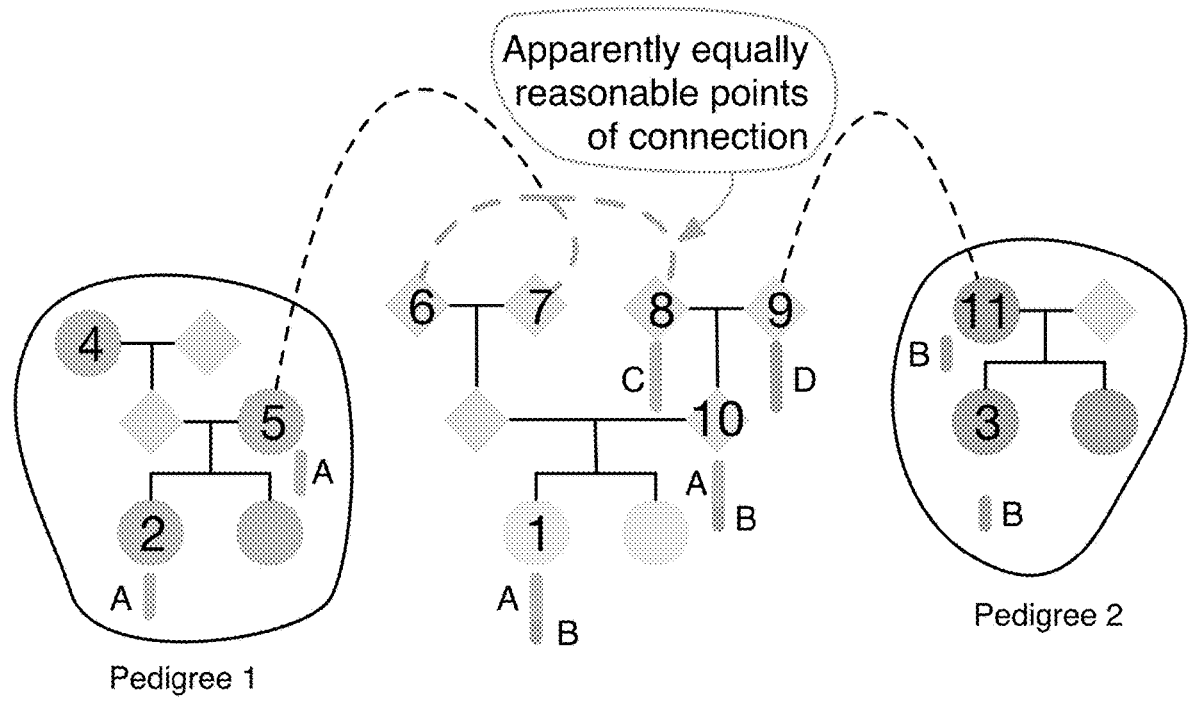
FIG. 5 Determining the parental side of distant relatives. Individual 1 in the cyan pedigree shares segment A IBD with individuals 2 and 5 in the purple pedigree and they share segment IBD B with individuals 3 and 11 in the red pedigree. If the lineage connecting individual 1 to the purple pedigree passes through ancestor 8 and the lineage connecting individual 1 to the red pedigree passes through individual 9, then the ranges of segments A and B cannot overlap because individual 10 only transmits one recombined haplotype to individual 1. Observing abutting segments A and B is evidence that the cyan pedigree is connected to the purple and red pedigrees through the same parent. Observing spatially overlapping segments A and B is evidence that the purple and red pedigrees are connected through different parents of individual 1. In the absence of segment overlaps and splicing information, the orange dashed lines indicate equally reasonable ways to connect the purple and cyan pedigrees.

Practitioners consider the problem of inferring whether two distant sets of relatives are related through the same parent of a focal individual, or through different parents. The scenario is shown in FIG. 5. Even if pedigrees 1 and 2 in FIG. 5 share no IBD, they could still be related to individual 1 through the same parent by passing through different grandparents.

The amount of IBD shared among pedigrees 1 and 2 is uninformative about whether they are related through the same parent. However, if pedigrees 1 and 2 are related to the focal individual 1 through the same parent, the IBD segments pedigree 1 shares with individual 1 cannot spatially overlap with the segments pedigree 2 shares with individual 1. This is because two overlapping segments would have undergone recombination in the parent (e.g., 10). The result will either be a spliced segment (FIG. 5), or the replacement of one segment by the other with possible reduction in segment size.

In the Bonsai method, when there are multiple possible grandparents through which we can connect two pedigrees $\mathcal{P}_1$ and $\mathcal{P}_2$ to a focal set of nodes $\mathcal{N}$ in a focal pedigree $\mathcal{P}$, we examine whether the IBD segments between $\mathcal{P}_1$ and $\mathcal{N}$ overlap with the IBD segments between $\mathcal{P}_2$ and $\mathcal{N}$.

Training the Probabilistic Relationship Model

Figure 7:
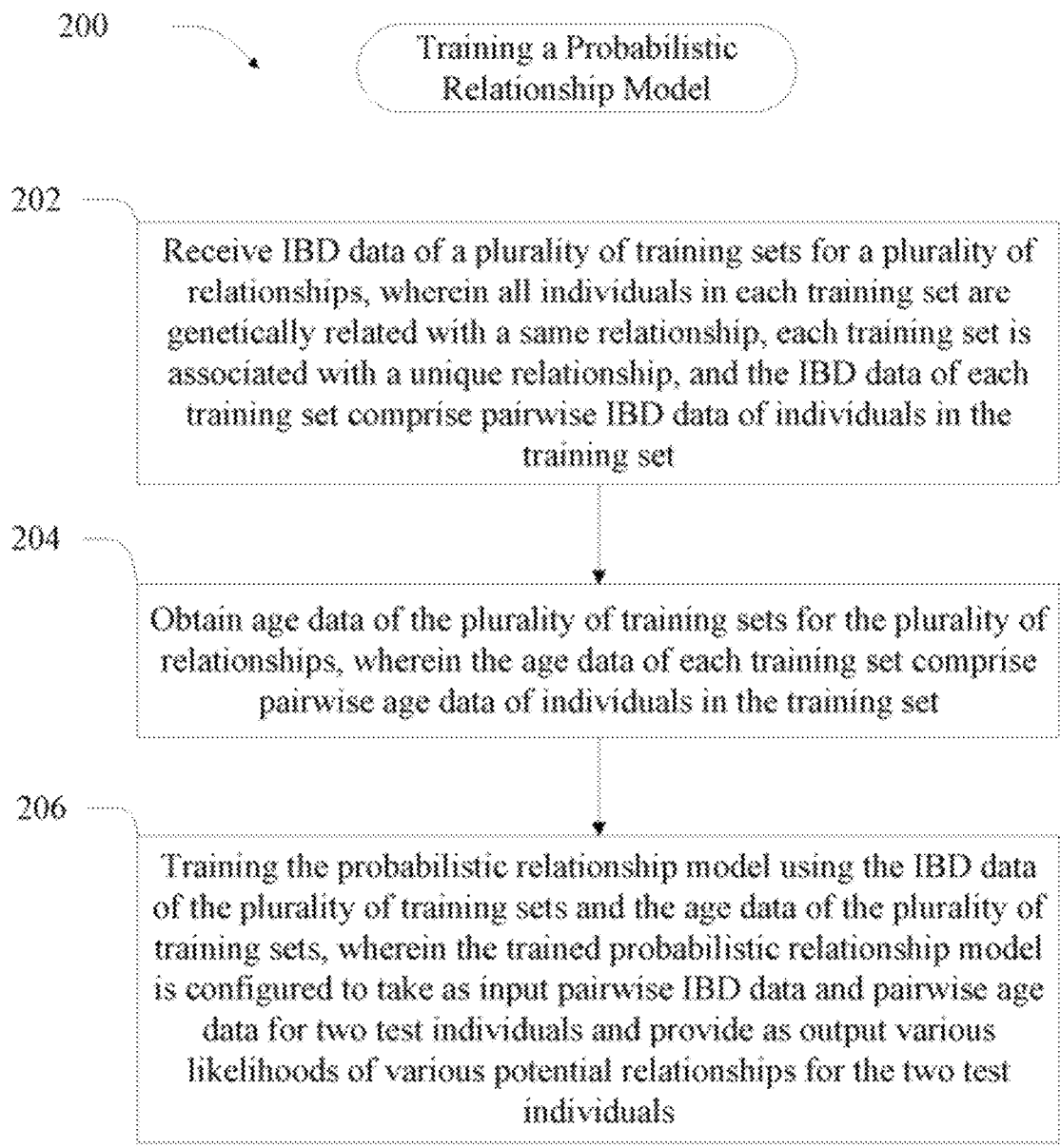
FIG. 7 shows a flowchart illustrating a process for training a probabilistic relationship model according to some implementations.

FIG. 7 shows a flowchart illustrating process 200 for training a probabilistic relationship model using a computer system including one or more processors and system memory. In some implementations, the probabilistic model is a machine-learning model. The trained probabilistic relationship model is configured to predict genetic relationships based on IBD data and age data.

Figure 8:
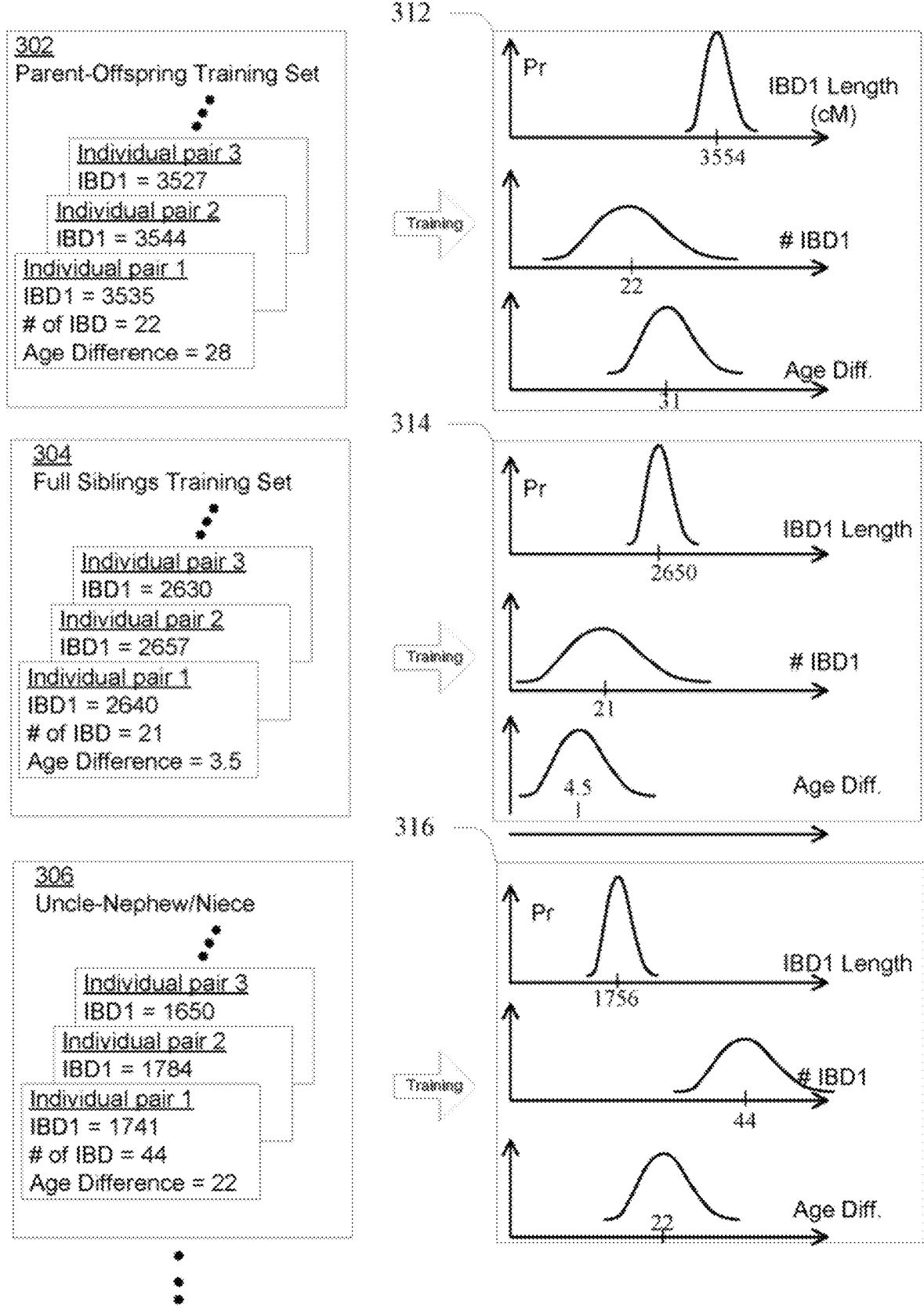
FIG. 8 schematically illustrates an example of how to train the machine learning relationship model using multiple training sets.

Process 200 starts by receiving IBD data of a plurality of training sets for a plurality of relationships. See block 202. All individuals in each training set are genetically related with the same relationship in a pairwise manner. Each training set is associated with a unique relationship. The IBD data of each training set include pairwise IBD data of individuals in the training set. FIG. 8 schematically illustrates an example of how to train the machine learning relationship model using multiple training sets. In some implementations, each training set includes hundreds, thousands, tens of thousands of individuals or more. In some implementations, the training set includes data of actual individuals having a particular genetic relationship. In some implementations, each training set includes data of simulated individuals. Such simulated data can be obtained from recombining reference individuals' data according to recombination models to generate related individuals' data for various types of relationships.

Process 200 further involves obtaining age data of the plurality of training sets for the plurality of relationships. The age data of each training set includes age data for individuals in the training set. See block 204.

Process 200 further involves training the probabilistic relationship model using the IBD data of the plurality of training sets and the age data of the plurality of training sets.

See block 206. The trained probabilistic relationship model is configured to take as input pairwise IBD data and age data for two test individuals and provide as output various likelihoods of various potential relationships for the two test individuals.

FIG. 8 schematically illustrates further details on how to train the probabilistic relationship model according to process 200 shown in FIG. 7. Boxes 302, 304 and 306 represent training sets for parent-offspring relationship, full siblings relationship, and avuncular relationship, respectively. The figure shows only three training sets for three relationships, but many more training sets that are used are not shown here. In some implementations, the various relationships include relationships of the $0^{th}$, $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, or $15^{th}$ degree or further. In some implementations, the various relationships include relationships of at least 0, 1, 2, 4, 6, 8, 10, 12, 14, or 16 meioses on a common-ancestor path between the two individuals through a common ancestor. In the training set of 302 for parent-offspring relations, the IBD data and age difference data for each pair of individuals is shown in a box. Here, the training data include half IBD (IBD1) length, number of IBD segments, and age difference. Other data may also be used to train relationship models. For example, the pairwise IBD data may include the length of full IBD (IBD2) segments, and/or the length of half IBD (IBD1) segments. The two types of lengths may be modeled as two separate probability distributions. Alternatively, the different types of IBD lengths may be combined, and the combined length may be modeled as a probability distribution.

As shown here the number of IBD segments is also used to train the probabilistic relationship model. In some implementations, the numbers of the two types of IBD segments may be modeled separately. In other implementations, the two numbers may be combined and modeled to have one probability distribution. Age difference between the two individuals in a pair is also used to train the probabilistic relationship model.

Three pairs of individuals are shown for parent-offspring training set 302. Each individual pair provides a data point of the length of half IBD, a data point of the number of IBD, and a data point of age difference. Although only three individuals are illustrated, the training set may include hundreds, thousands, or tens of thousands of individuals or more.

The data points from the individuals in the training set for each variable (IBD1, number of IBD segments, age difference) are used to train a probabilistic relationship model. The probabilistic relationship model models the probability distribution of each variable as a Gaussian distribution in this example. In other implementations, the probability distribution of each variable may be modeled as an exponential distribution, a Poisson distribution, a binomial distribution, a beta binomial distribution, and other suitable distributions based on prior knowledge of the variable.

The data points from the individuals in the training set for each variable (IBD1, number of IBD, age difference) are used to train a probabilistic relationship model. The probabilistic relationship model models the probability distribution of each variable as a Gaussian distribution in this example. In other implementations, the probability distribution of each variable may be modeled as an exponential distribution, a Poisson distribution, a binomial distribution, a beta binomial distribution, and other suitable distributions based on prior knowledge of the variable.

The data from the training set 302 for the three variables (IBD1 length, number of IBD segments, and age difference) are used to train the probabilistic model. In some implementations, training involves using various techniques to fit the probability distribution to the training data. In some implementations, method-of-moments techniques are used to fit the Gaussian distribution of each variable to the training data. The probability distributions for the three variables are shown in box 312 for parent-offspring relationship. The data and the distributions in the figure are for illustrative purposes only, and they do not reflect biological or mathematical reality. In the same manner, full siblings training set data 304 are used to train the probabilistic relationship model to obtain the probability distributions for the three variables as shown in box 314. The training data of avuncular relationship in box 306 are used to train the probabilistic relationship model to obtain the probability distributions for the three variables for the avuncular relationship.

After the model is trained, it can be applied to estimate relationship likelihoods between individuals based on IBD data and age differences between the individuals. To apply the probabilistic relationship model, test data of two test individuals are provided to the trained model. The model provides as output the probability of each variable for each relationship. Multiple probabilities for multiple independent variables are aggregated in a relationship to provide a likelihood of the relationship. For example, likelihoods for a relationship as functions of each of the three variables may be summed to provide a composite likelihood indicating how likely the relationship is given the two test individuals' IBD and age data.

Regarding training, various techniques may be used to fit the model to the data. In some implementations, maximum likelihood methods may be used to obtain parameters that maximize the likelihood of the model given the data. In some implementations, method-of-moments techniques may be used to calculate distribution parameters from the training data. Other model fitting techniques such as kernel density estimation may also be employed, although such techniques tend to provide less accurate estimates in some applications.

Generating Pedigree Graphs

Another aspect of the disclosure provides methods for generating pedigree graphs that are informative, user-friendly, easy to understand or intuitive.

Figure 9:
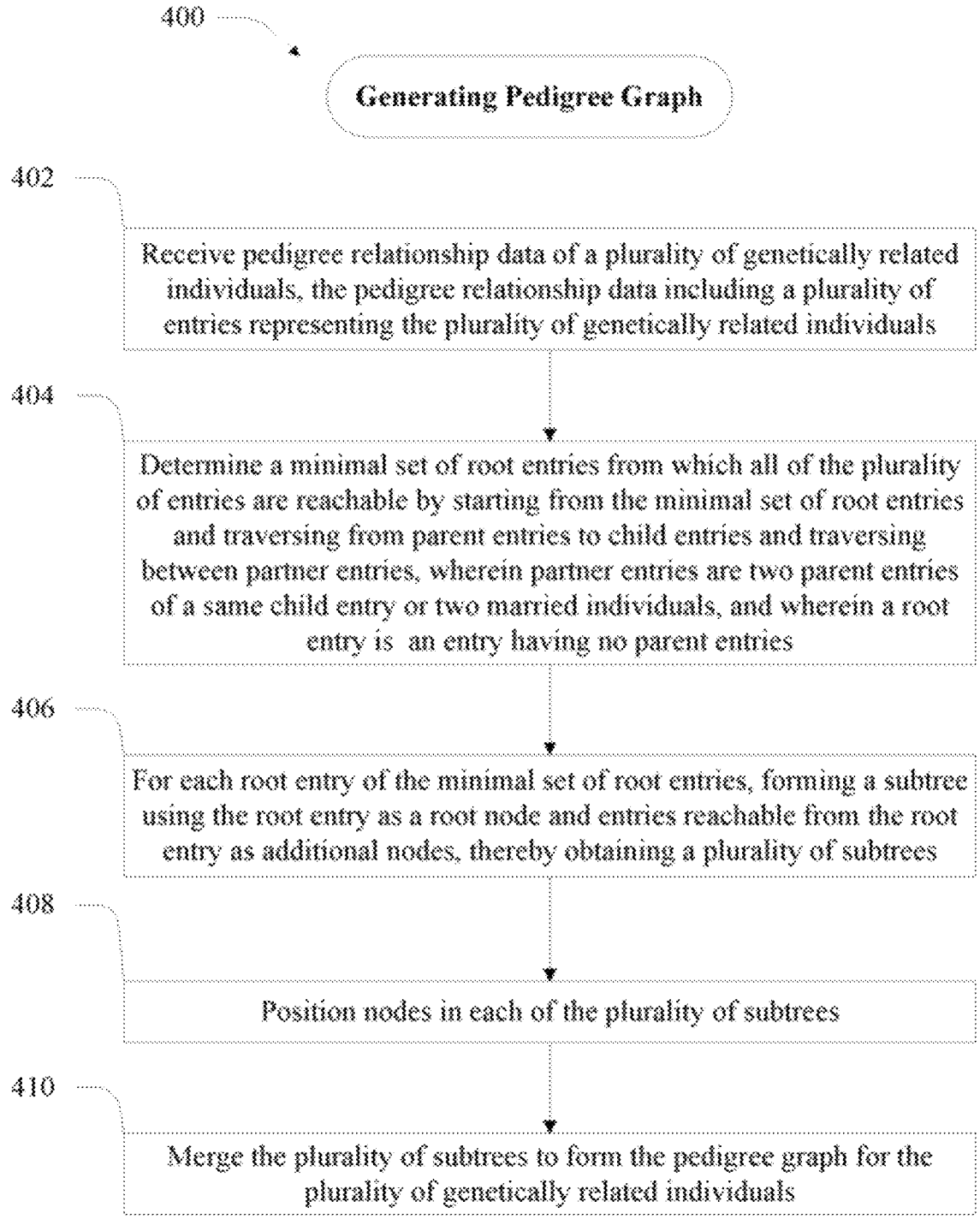
FIG. 9 shows a flowchart illustrating a process for generating pedigree graphs according to some implementations.

FIG. 9 shows a flowchart illustrating process 400 for generating pedigree graphs using a computer system that includes one or more processors and system memory. Process 400 involves receiving from a database pedigree relationship data of a plurality of genetically related individuals. See block 402. The pedigree relationship data include a plurality of entries representing the plurality of genetically related individuals. Each entry includes links relating each child entry to its parent entries in a dataset. A child entry and its parent entries represent a child and its biological parents respectively.

FIG. 10 illustrates three such entries that can be used in the process for generating the pedigree graph. The first entry has an identifier of value 1. It has a null link to its parent entries. This indicates that this entry does not have known parents in the plurality of individuals in a dataset. Such an entry is considered a root entry that may be used to generate a root node of a graph having a tree structure. The entry in the middle has an entry identifier of value 2, and a null link to its parent entries, indicating that the individual represented by the entry does not have parents in the dataset. The entry at the bottom has an identifier of value 12, and a link indicating is parent entries, showing that entry 1 and entry 2 are its parent entries.

In some implementations not shown in FIG. 9, various preprocessing steps may be performed after the pedigree relationship data are received. One of the preprocessing steps involves performing passes over entries to determine various properties on the entry. For example, determining for each entry its child entries, sibling entries, partner entries, etc. based on parent-child relations among these entries. Another preprocessing step involves determining ideal ordering of partners when there are multiple partners. For example, an entry having the largest number of partners is placed towards the center of a row of partners. This can help to reduce crossing of lines that connect different nodes. Another preprocessing step involves marking entries for important nodes, such as the focal node, nodes in the nuclear family, core nodes, etc. Another preprocessing step involves determining the chain of nodes linking each node back to the focal node.

Process 400 then involves determining a minimal set of root entries from which all of the plurality of entries are reachable by starting from the minimal set of root entries and traversing from parent entries to child entries and traversing between partner entries. See block 404. As mentioned above, a root entry is an entry having no parent entries. Partner entries are two parent entries of the same child entry. In some implementations, two partner entries may be generated based on other information, such as non-genetic information indicating marriage or partnership that does not yield children. One can travel from one partner to another partner through the partner's children.

Process 400 further involves forming a subtree, for each root entry of the minimal set of root entries, using the root entry as a root node and entries reachable from the root entry as additional nodes. This operation obtains a plurality of subtrees. See block 406. Root nodes do not have parent nodes, and they tend to be at the top of a subtree. On the contrary, leaf nodes do not have child nodes, and they tend to be at the bottom of a subtree.

Process 400 further involves positioning nodes in each of the plurality of subtrees. See block 408. In some implementations, positioning the nodes involves starting from the root node and recursively going through nodes in a defined order to reach nodes to be positioned. In some implementations, the defined order is as follows.

1. children of partners to the left;
2. children of partners to the right;
3. partners to the left;
4. self; and
5. partners to the right In some implementations, positioning nodes in each of the plurality of subtrees involves placing a leaf node without any siblings on the left at an origin. It also involves placing a leaf node with a sibling immediately to its left at a position immediately to the right of said sibling. In some implementations, it also involves positioning parent nodes relative to their child nodes so that they are further from the horizontal center of a row of nodes than its child nodes are. In some implementations, positioning nodes also involves positioning parent nodes relative to their child nodes' partner nodes, so that they are further from the horizontal center of a row of nodes than their child nodes' partner nodes are.

Figure 11:
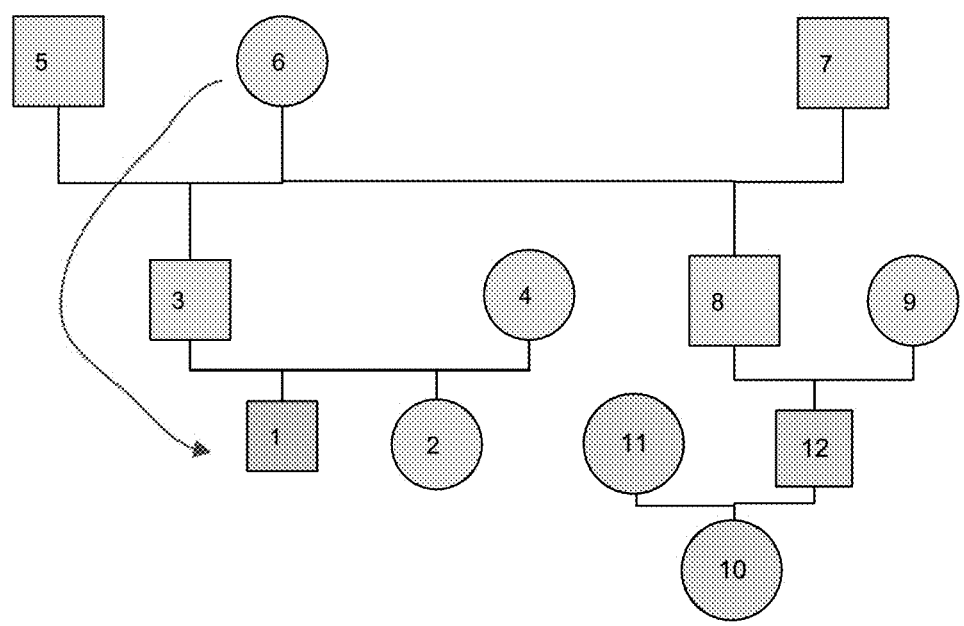
FIG. 11 shows a subtree that can be formed from a root node according to some implementations.

FIG. 11 shows a subtree that can be formed from a root node (node 6). By recursively going through nodes in the defined order described above, one gets to node 1, which is a leaf node without any siblings on the left. So it can be placed at an origin (0, 0). The process of positioning nodes next would reach node 2, which is a leaf node with a sibling immediately to its left (node 1). The process places node 2 at a position immediately to the right of node 1 at (1, 0). Following the same rules to reach different nodes and positioning the nodes, the left branch of the subtree can be placed as shown at the top of FIG. 12A.

Figure 12:
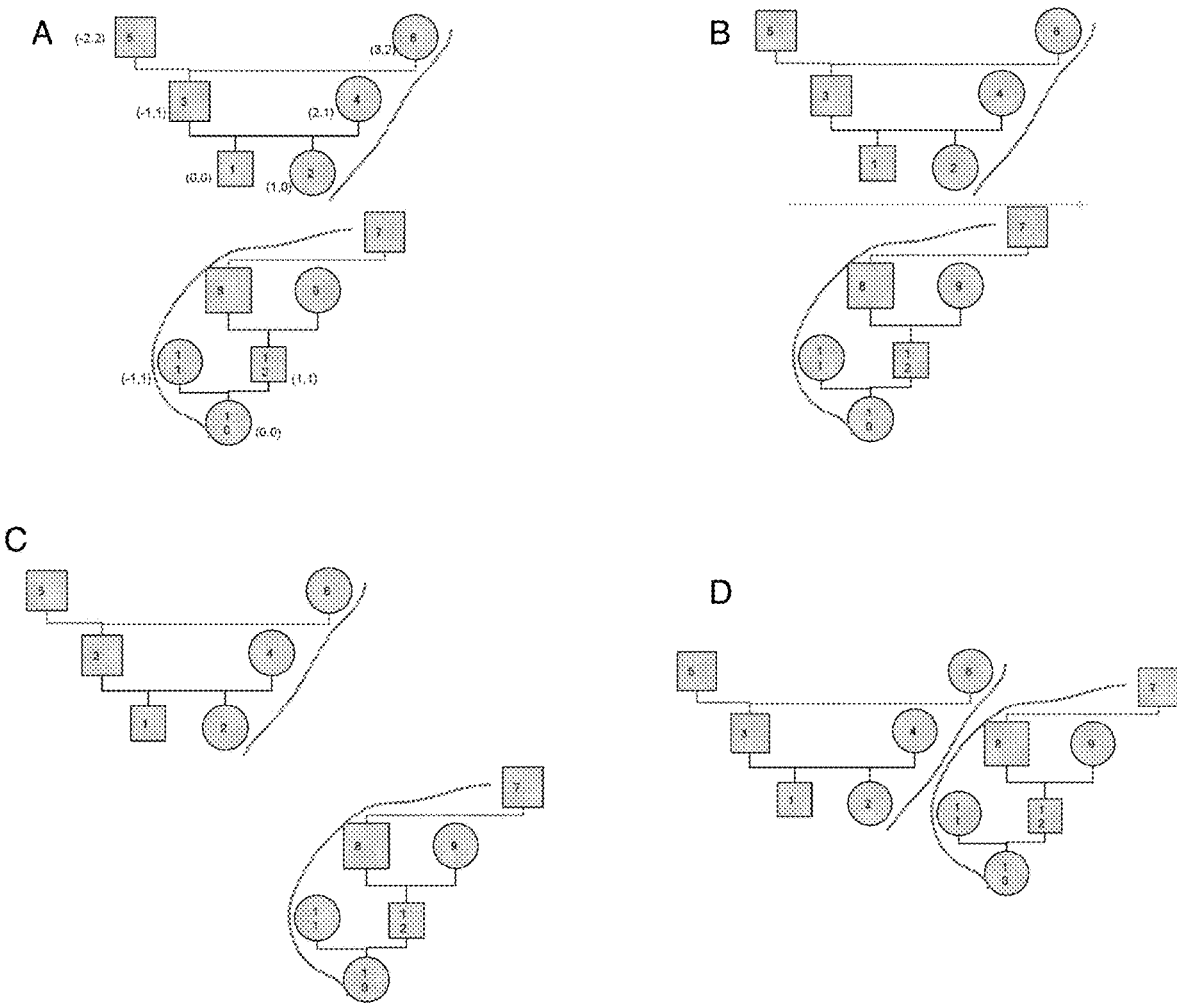
FIG. 12 illustrates shifting one branch of a subtree.

Similarly, the right branch of the subtree may be placed in positions as shown in FIG. 12A at the bottom. Note that even though the left branch and the right branch are illustrated as the top half and the bottom half of FIG. 12A, they actually overlap, because, e.g., node 1 and node 10 are both placed at the origin (0, 0). The process maintains positions of the right contour of the left branch and the left contour of the right branch. The positions of the contours are obtained from parent nodes that are not on the outside of the subtree and its children nodes not on the outside of the subtree. The right contour of the left branch and the left contour of the right branch may then be used to horizontally shift the two branches so that the two branches do not overlap on non-corresponding nodes as shown in FIGS. 12A-D.

In some implementations, there are more than two parent nodes in a row. A first parent node is not on either end of the row. A second parent node is immediately to the left of the first parent node. These implementations include a rule of positioning the first parent node relative to the child nodes of the second parent node, so that the first parent node is to the right of the child nodes of the second parent node.

Figure 14:
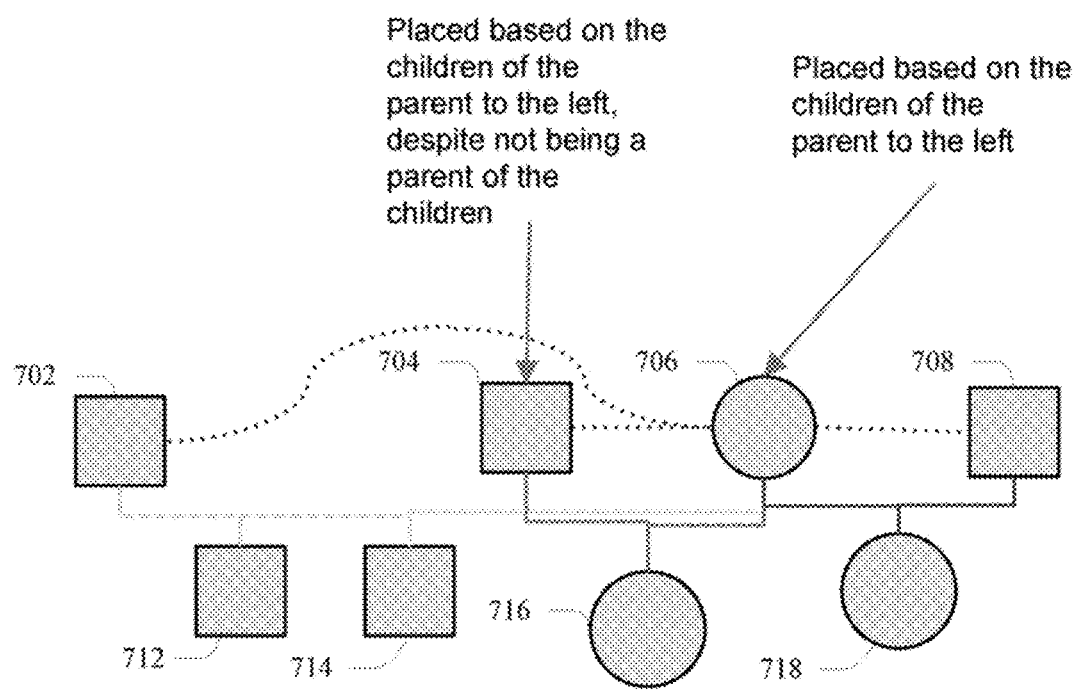
FIG. 14 illustrates positioning of a row of four parent nodes according to some implementations.

FIG. 14 illustrates the positioning of a row of four parent nodes according to the rule. In this illustrative example, there are four parent nodes in a row (702, 704, 706, 708). Node 706 is the partner of nodes 702, 704, and 708. Node 718 is the child of parent nodes 706 and parent nodes 708. Node 716 is the child of nodes 704 and 706. Node 712 and node 714 are children of node 706 and node 702.

Parent node 706 is not on either end of the row. Parent node 704 is immediately to the left of parent node 706. In this case, the rule described above positions the parent node 706 relative to child node 716, which is the child of parent node 704. Node 702 is not a partner of node 704. Nonetheless, the same rule described above applies to node 704 and 702. Node 704 is not on either end of the row. It is placed relative to the two child nodes of node 702 so that it is to the right of node 714, a child of node 702.

In some implementations, after positioning the first parent nodes relative to the child nodes of the second parent, the process shifts the child nodes of the first parent node to maintain previous relative relations between positions between the first parent and the child nodes of the first parent.

Returning to FIG. 9, process 400 finally merges the plurality of subtrees to form the pedigree graph for the plurality of genetically related individuals after the nodes are positioned in the subtree. See block 410.

In some implementations, merging the subtrees to form the pedigree graph involves shifting one or more of the subtrees so that non-corresponding nodes of different subtrees do not overlap. Non-corresponding nodes on different trees are nodes that do not represent the same individual. FIGS. 12A-D illustrate shifting one branch of a subtree, but the same shifting techniques are also used to shift subtrees. Some implementations also involve merging corresponding nodes on different trees into one node. Corresponding nodes are nodes on different subtrees that represent the same individual.

In some implementations, merging the subtrees to form the pedigree graph includes identifying core nodes that include a focal node representing a focal individual, any sibling nodes representing siblings of the focal individual, any parent nodes representing parents of the focal individual, any descendant nodes presenting descendants of the focal individual, and any partner nodes presenting partners of the descendants.

Figure 13:
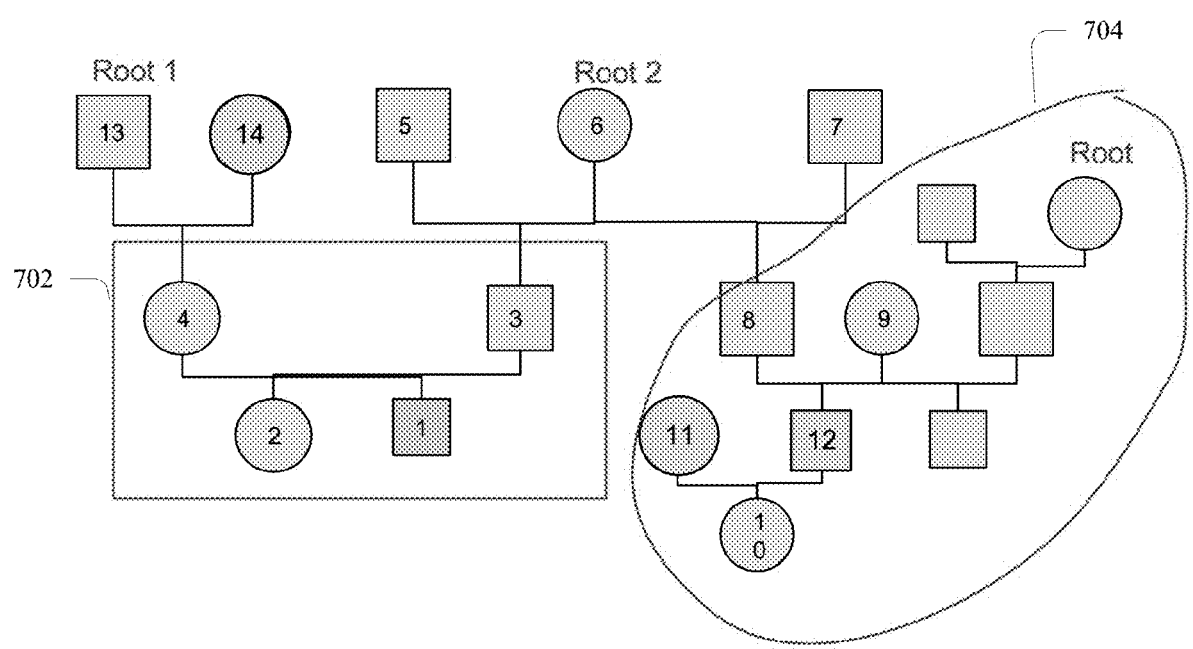
FIG. 13 shows a pedigree graph obtained by merging pedigree subtrees.

For example, for the pedigree graph in FIG. 13, the focal node is node 1. The core nodes include nodes 1-4 shown in box 702. Two subtrees from root node 13 and node 6 merge on the four core nodes. In some implementations, the process further involves merging subtrees that do not intersect with the core nodes into subtrees that do intersect with the core nodes. In FIG. 13, the subtree 704 does not overlap with any of the core nodes. However, it does intersect with the subtree including node 6. In such case, the subtree 704 is merged to the subtree including node 6, which intersects with the core nodes.

Figure 15:
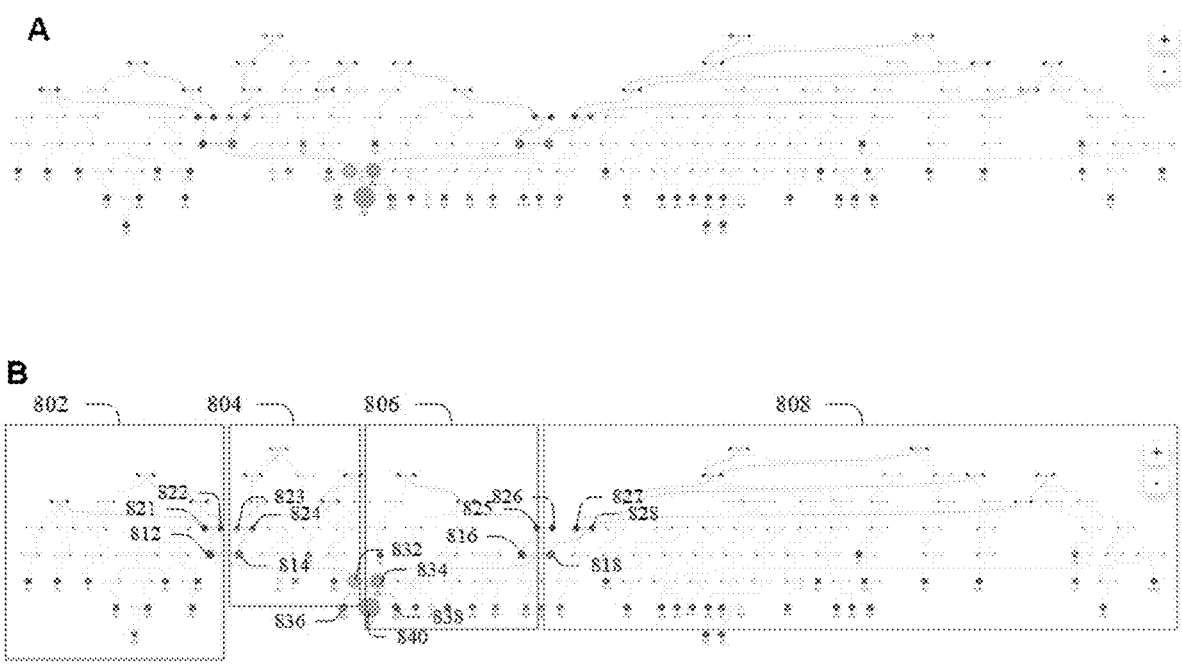
FIG. 15 shows an example of a pedigree graph in two views according to some implementations.

In some implementations, merging the plurality of subtrees involves merging each pair of four pairs of subtrees to form four grandparent subtrees. See FIGS. 15 A and B. Here the four pairs of subtrees respectively correspond to four pairs of great-grandparents of the focal individual. The four pairs of great-grandparents are nodes (821, 822), (823, 824), (825, 826) and (827, 828) as shown in FIG. 15B. The focal individual is represented by node 840. The four grandparent trees are shown in box 802 corresponding to grandparent 812, box 804 corresponding to grandparent 814, box 806 corresponding to grandparent 816, and box 808 corresponding to grandparent 818.

Figure 16:
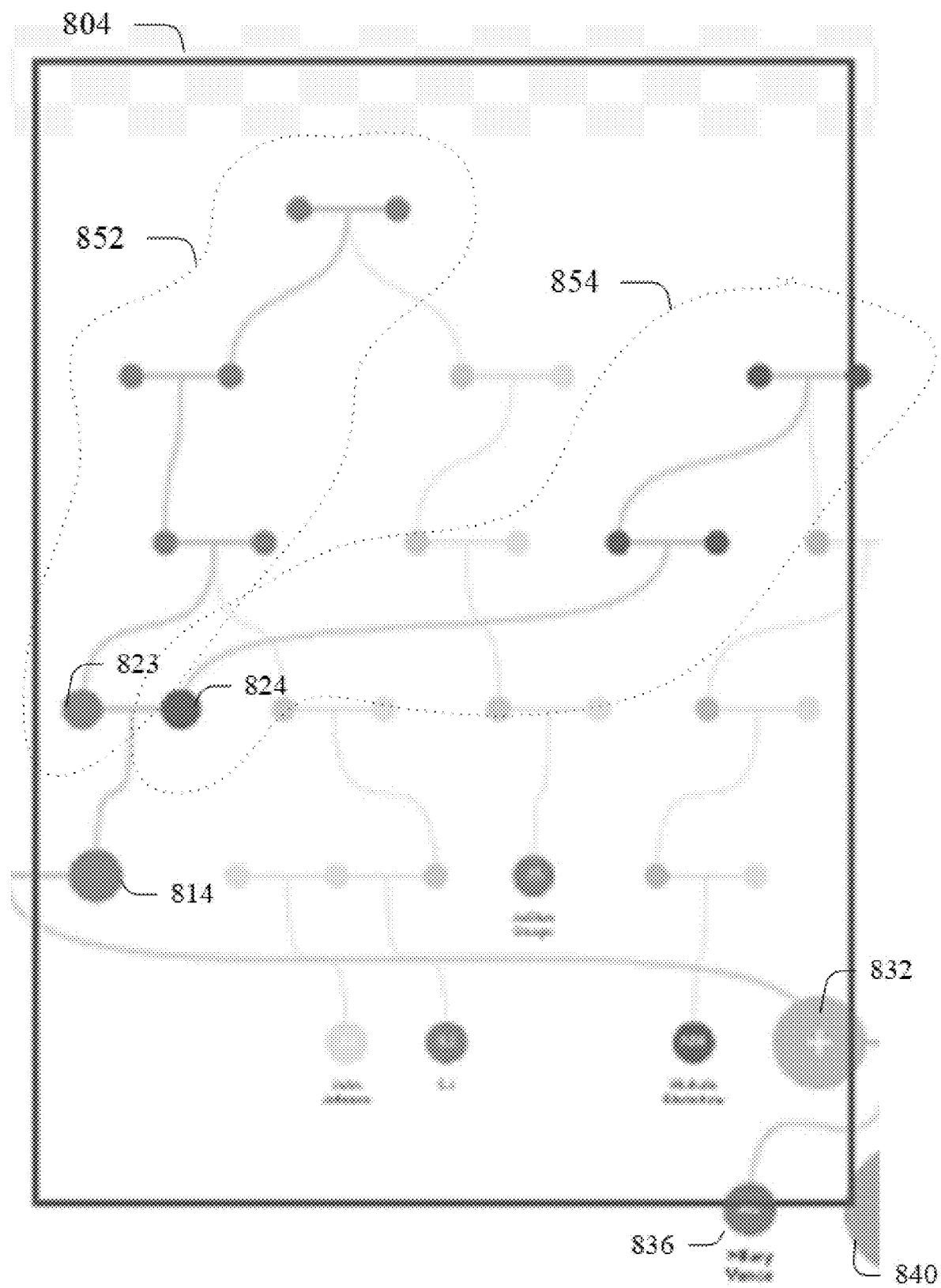
FIG. 16 shows a close-up of a grandparent tree.

Here, merging each pair of subtrees includes horizontally shifting one subtree so that non-corresponding nodes of the two subtrees do not overlap, and merging two corresponding nodes on the pair of subtrees representing the same grandparent into one node. See FIG. 16. FIG. 16 is a close-up of the grandparent tree corresponding to grandparent 814 in box 804. This subtree includes two subtrees for two great-grandparents 823 and 824, which are direct ancestors of the focal node. In these two great grandparent trees, the direct ancestors of the focal node 840 are colored as orange. Nodes that are not direct ancestors of the focal node are not connected by colored lines. The colored branch of the great-grandparents subtree above great-grandparent 823 is shown in area 852. The colored branch of the great-grandparents tree above great-grandparent 824 is shown in area 854. These two branches include non-corresponding nodes because they do not represent same individuals on the two great-grandparent subtrees. Merging these two great-grandparents trees involves shifting one of the two trees so that non-corresponding nodes on them do not overlap.

In some implementations, the process further involves merging the four grandparent subtrees to form the pedigree graph. The merging involves horizontally shifting one or more of the grandparents subtrees so that non-corresponding nodes of different grandparent subtrees do not overlap and merging corresponding nodes on different grandparent subtrees presenting the same individual into one node. In the pedigree tree graph in FIG. 15B, node 832, 834, and 840 are obtained by merging corresponding nodes from the four grandparent subtrees.

In some implementations, the subtree corresponding to a great grandparent is obtained by merging two or more subtrees. See, e.g., FIG. 15B, the great-grandparent subtree corresponding to great grandparent 818 shown in box 808, which is obtained by merging two or more subtrees.

In some implementations, the two grandparent subtrees in the middle are smaller than the two grandparent subtrees on the outside. See FIGS. 15 A and B for example. In some implementations, generating pedigree graphs further involves swapping positions of two partner nodes whose parental subtrees are on the opposite side from the partner nodes.

Some implementations further involve removing empty spaces in the pedigree graph. In some implementations, this involves removing a column of empty spaces in the pedigree graph when the removal of the empty spaces does not cause any non-corresponding nodes to overlap.

In some implementations, the process further includes applying force directed graph drawing techniques to redraw one or more nodes and lines connecting them. In some implementations, the one or more nodes include leaf nodes and their parent nodes.

In some implementations each pair of two or more pairs of parent nodes in the pedigree graph includes two nodes rendered in different colors. In some implementations, the lines connecting each child node to its parent nodes includes curved lines.

Graphical User Interface for Pedigree Graphs

Another aspect of the disclosure relates to methods for displaying the pedigree graph for a plurality of genetically related individuals on a graphical user interface (GUI). The method is implemented using a computer system including a processor, system memory, and a display device. The method includes using the display device to display a pedigree graph including a plurality of nodes representing a plurality of genetically related individuals and lines connecting each child node to its pair of parent nodes. The child node and its pair of parent nodes present a child and its pair of parents. Each pair of two or more pairs of parent nodes includes two nodes rendered in different colors. The lines connecting each child node to its pair of parent nodes include curved lines.

FIG. 15B shows an example pedigree graph that is displayed according to some implementations. In the pedigree graph, the two or more pairs of parent nodes include (832, 834), (812, 814), (816, 818), (821, 822), (823, 824), (825, 826), (827, 828). For these pairs, two nodes of each pair are rendered in different colors.

In some implementations, e.g., FIG. 15B, all nodes of the two or more pairs of parent nodes are rendered in different colors. In other words, all of the nodes listed above have colors that are different from each other.

In some implementations, the two or more pairs of parent nodes are direct ancestors of a focal node. In the example shown in FIG. 15, all of the above listed parent nodes are direct ancestors of focal node 840.

In some implementations, the relative nodes that are not direct ancestors of the focal node have the same coloring as a direct ancestor that is on the same family side and at the same generational level as the relative nodes.

In some implementations, generation levels at and above great-grandparents are rendered in the same color on the same side of the family.

In some implementations, nodes at the pedigree graph include core nodes that include the focal node representing a focal individual, any sibling nodes resenting siblings of the focal individual, any parent nodes representing parents of the focal individual, any descendant nodes resenting descendants of the focal individual, and any nodes resenting partners of the descendants. In the example in FIG. 15B, the core nodes include focal node 840, sibling nodes 836, 838, and parent nodes 832 and 834.

In some implementations, the pedigree graph includes lines indicating direct ancestry of the focal individual. The lines indicating the direct ancestry of the focal individual are rendered in a color or shade that is different from lines not indicating the direct ancestry of the focal individual. In the example in FIG. 15B, the lines indicating the direct ancestry of the focal individual 840 are rendered in yellow, which is different from other lines not indicating direct ancestry of the focal individual.

In some implementations, at least one pair of parent nodes has an off-center alignment relative to their child nodes. See, e.g., parent nodes 827 and 828 relative to their child node 818.

In some implementations, two subtrees having the same topology in the pedigree graph are represented in different forms.

In some implementations, at least one pair of parent nodes has an inter-pair physical distance of larger than the smallest possible distance. See, e.g., parent nodes 814 and 812.

In some implementations, one or more nodes and lines connecting them are drawn using force directed graph drawing techniques. In some implementations, the one or more nodes include leaf nodes and their parent nodes. See e.g., leaf nodes 836, 840, and 838, and parent nodes 832 and 834.

In some implementations, each child node is connected through a curved line to a straight line connecting the child node's parent nodes. See most of the direct ancestry lines on pedigree graph in FIG. 15B.

In some implementations, the GUI can interactively display and update the pedigree graph. A user may provide user input relating to genealogy information on any individuals represented by the nodes of the pedigree graph. In some implementations, the user input is provided in a way that involves an interaction with an input text field of the GUI and/or an interaction with a graphical element of the pedigree graph. For example, the user may point and click at a node on the pedigree graph, which activates an editing mode of the node. Then the user may provide genealogical or other information about the individual represented by the node. The information may include age, gender, partnership, ethnicity, nationality, relative relationship, name, photos, etc. A computer processor can then use data provided by or derived from the user input data to update the pedigree information underlying the pedigree graph or update the pedigree graph directly. Some implementations store and/or propagate the updated pedigree information to generate other pedigree graphs involving said information.

In some implementations, two or more different users may provide input to two or more different pedigree graphs. In some implementations, a computer system uses the input from one user to update the pedigree graph of another user, and vice versa. In such implementations, two or more different users can collaboratively update their pedigree graphs in real time.

In various embodiments, the pedigree graph is interactive. Namely, the pedigree graph is designed or configured to receive user input, modify information associated with the pedigree graph, and update the pedigree graph using the modified information. In some implementations, the user input is received via a user interaction with the pedigree graph in a GUI. In some implementations, the user interaction includes clicking an interactive node in the pedigree. An interactive node is one that is configured to receive user input and present information, sometimes the presented information being updated by the user input.

In some implementations, updating the pedigree graph automatically updates one or more display elements of the pedigree graph or in the GUI. In some implementations, the user interaction includes entering data using a window activated by clicking the interactive node. In some implementations, updating one or more elements of the pedigree graph includes changing a relationship between the interactive node and at least one other node in the pedigree graph. In some implementations, at least one interactive node in the pedigree graph is associated with information of health, traits, diseases, physical conditions, or phenotypes of an individual represented by the at least one interactive node.

In some implementations, the at least one interactive node is associated with a graphical element representing the information of health traits, diseases, physical conditions, or phenotypes of the individual. In some implementations, the user input includes clicking the interactive node. The user provides input by clicking the interactive node. In some implementations, the user input includes entering information of individuals in a window activated by clicking the interactive node. In some implementations, updating the one or more elements of the pedigree graph includes changing at least one relationship between two nodes. In some implementations, updating the one or more elements of the pedigree graph includes changing the graphical element representing information of traits, diseases, physical conditions, or phenotypes of the individual.

In some implementations, the nodes of the pedigree graph, or associated with information relating to diseases, physical conditions, traits, or phenotypes. In some implementations, the information of diseases, traits, physical conditions, or phenotypes is represented by a graphical icon by graphical elements positioned next to the node. The graphical elements reflect conditions of the individual represented by the node.

Figure 32:
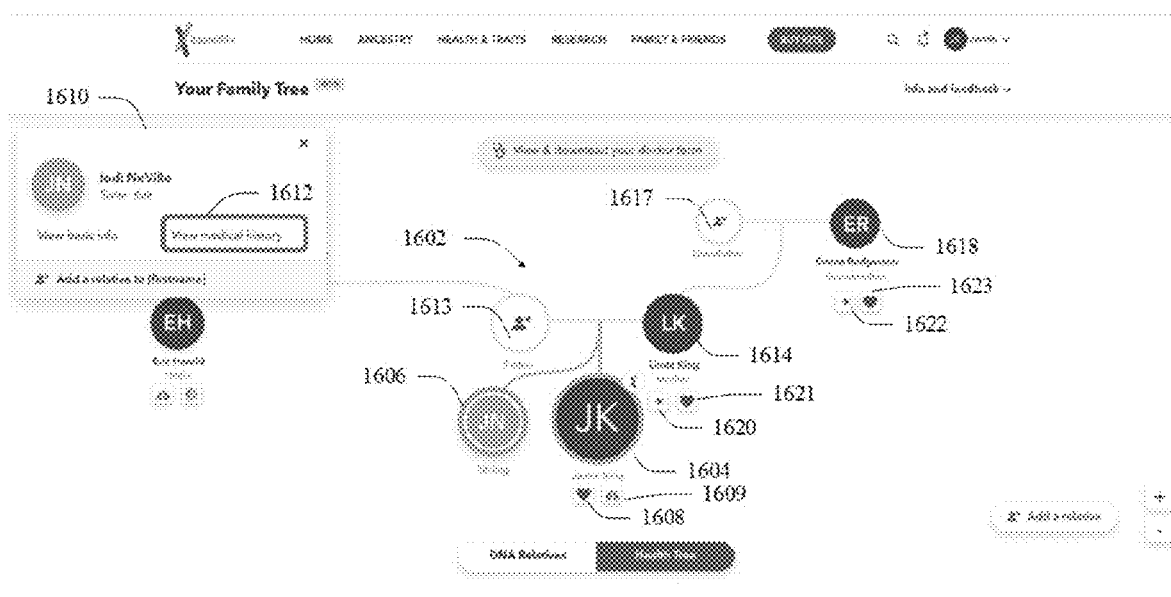
FIG. 32 shows an example of a pedigree graph with health related information.

FIG. 32 shows a pedigree graph as an example according to some implementations. The pedigree graph 1602 has a focal node 1604, a sibling node 1606, a father node 1613, a mother node 1614, a grandfather node 1617, a grandmother node 1618, etc. Node 1604, node 1614, and node 1618 are associated with health information of the individuals represented by the nodes.

Graphical icons 1608 and 1609 respectively represent a heart condition and a lung condition of a focal individual represented by node 1604. Graphical icons 1608 and 1609 are positioned with respect to node 1604. Similarly, graphical icons 1620 and 1621 respectively represent an eye color and a heart condition of the mother represented by node 1614. Graphical icons 1620 and 1621 are positioned with respect to mother node 1614. Similarly, graphical icons 1622 and 1623 respectively represent an eye color and a heart condition of the grandmother represented by 1618. Graphical icons 1622 and 1623 are positioned with respect to the node 1618. The juxtaposition of the nodes and icons in the pedigree graph visualizes the heritability of diseases and traits.

In this example, the user interacts with the pedigree graph by inputting information related to the pedigree or individuals in the pedigree. In some implementations, the information comprises traits, diseases, physical conditions, or phenotypes. In some implementations, the user may provide input regarding a node, such as node 1606 by clicking the node 1606, which brings up a graphical window or GUI 1610 for displaying and receiving information about Jodi Neville represented by node 1606. In GUI 1610, user may interact with elements in the window to display further information and/or input information related to Jodi. In this example, the user may further view Jodi's medical history information by clicking a link or button 1612, which brings up another GUI 1702 in FIG. 33 showing Jodi's medical information or ways to enter information about Jodi.

Figure 33:
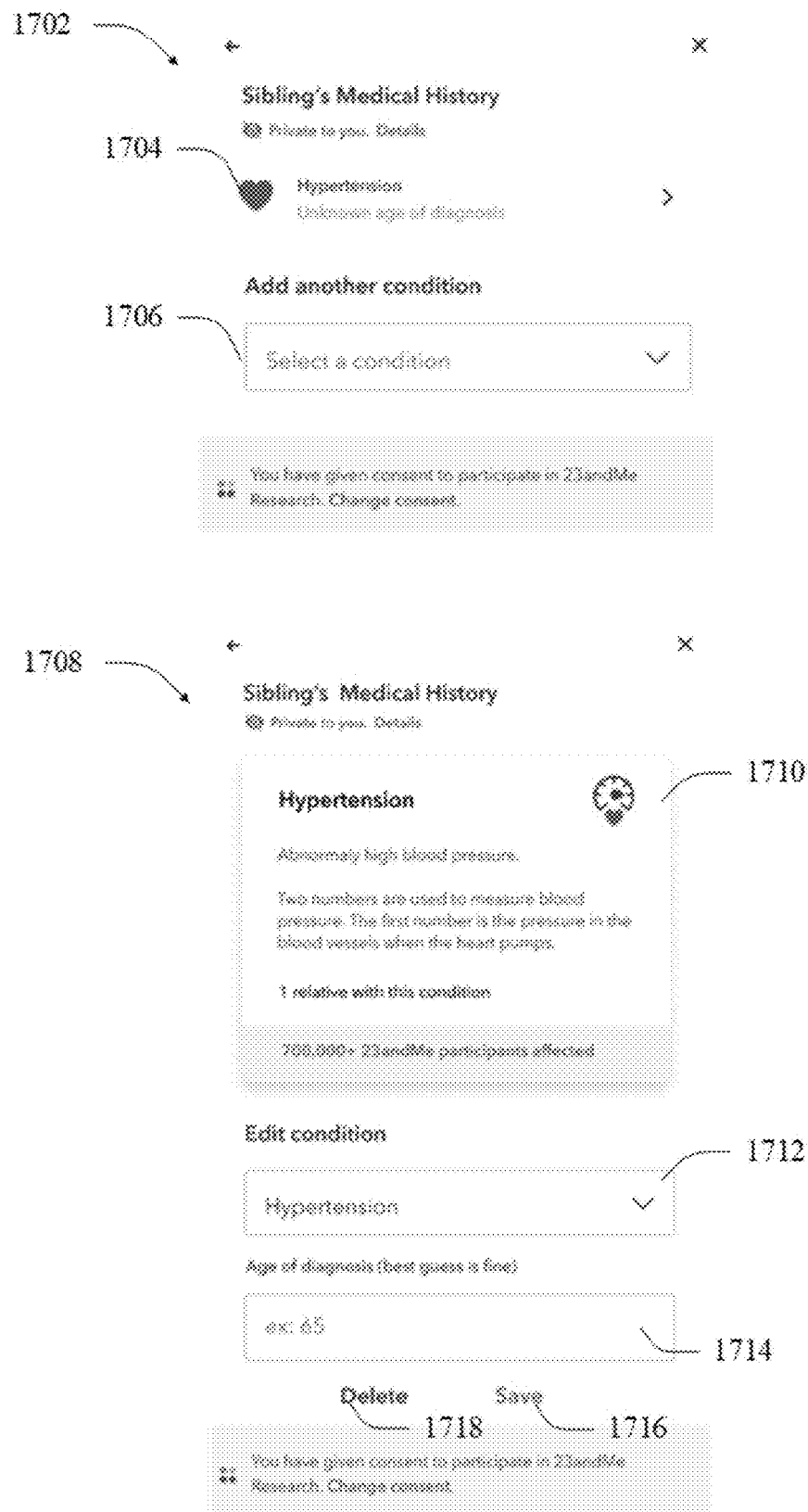
FIG. 33 shows two GUIs activated from the pedigree graph with health related information.

FIG. 33 shows GUI 1702 and GUI 1708 for viewing and inputting data about Jodi. Jodi has hypertension as indicated by display element 1704 in GUI 1702. GUI 1702 also allows the user to input other conditions of the individual via display element 1706. The user may click on display element 1704 to bring up GUI 1708 that includes more information of the hypertension condition. GUI 1708 includes community and relative information regarding hypertension in display element 1710. In GUI 1708, the user may also edit the condition in area 1712 and area 1714. A user may also save the information using display element 1716, or delete the information using display element 1718.

Re-Annotating Pedigree Graphs

In many implementations and applications, a pedigree graph includes nodes for both genotyped individuals and ungenotyped individuals. Pedigree graphs can also be referred to as family trees. A genotyped node represents an individual whose genetic data have been used to determine the pedigree relationships depicted by the pedigree graph. An ungenotyped node represents an individual whose genetic data have not been used to determine the pedigree relationships depicted by the pedigree graph. Since ungenotyped nodes are inferred from the pedigree relationships, information about the individual is limited to the inference from the pedigree relationships.

Figure 27:
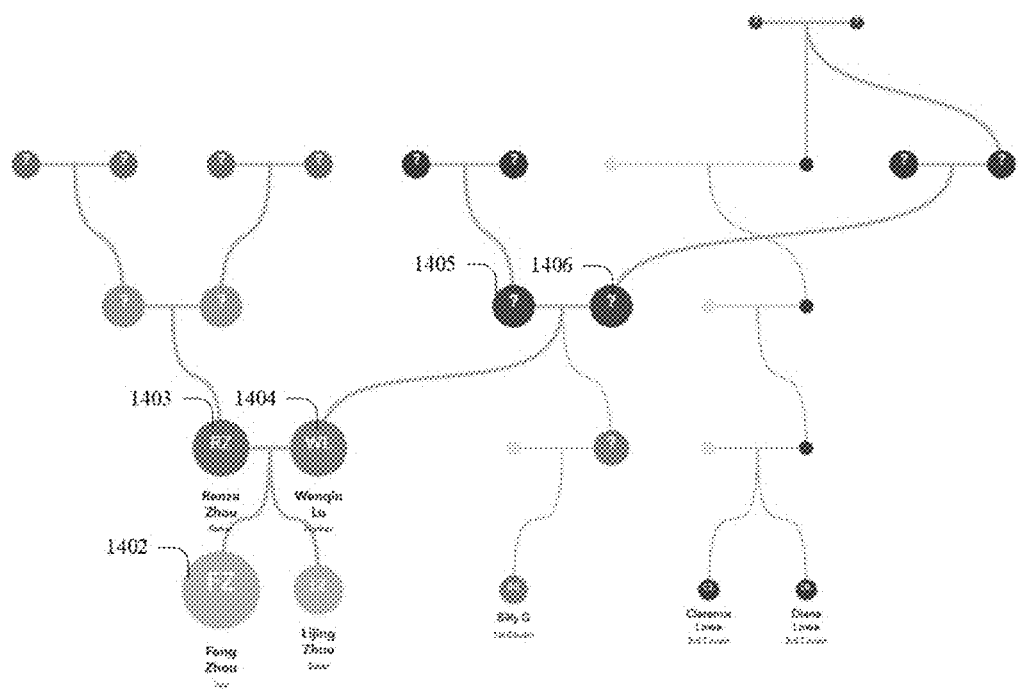
FIG. 27 shows an example implementation of displaying a pedigree graph and receiving user input for annotating un-genotyped nodes of the pedigree graph.

For example, FIG. 27 shows a pedigree graph including genotyped nodes and ungenotyped nodes. Each genotyped node is labeled with two letters. For example, the focal node (node 1402) labeled as FZ has a genotyped sibling labeled as LZ. It also has two genotyped parents 1403 and 1404. It can be inferred that each of the parents has two parents and four grandparents. For instance, the parent node 1404 is inferred to have two parents 1405 and 1406. These inferred individuals are also shown in the pedigree graph. They are not associated with data beyond the inferred relationships among them.

A user may annotate ungenotyped nodes using annotation information such as name, gender, date of birth, etc. Such information and annotation are helpful for understanding individuals and the relationships represented by the pedigree graph, making the graph more informative. When a pedigree graph is updated with new relationships or additional individuals based on genotyped data, the identities of genotyped nodes are known, and their matching between an old graph and a new graph is straightforward. However, because the identities of the unannotated, ungenotyped nodes in a new graph are unknown, matching them to annotated, ungenotyped nodes in an old graph is not as straightforward. The matching requires using relationships between ungenotyped nodes and genotyped nodes. But such relationships in the old graph and the new graph may not be the same, making it difficult to re-annotate ungenotyped nodes in the new graph using annotation data of corresponding nodes in the old graph. Some implementations provide methods and systems for re-annotating un-genotyped nodes in pedigree graphs using annotation data of prior graphs.

Figure 25:
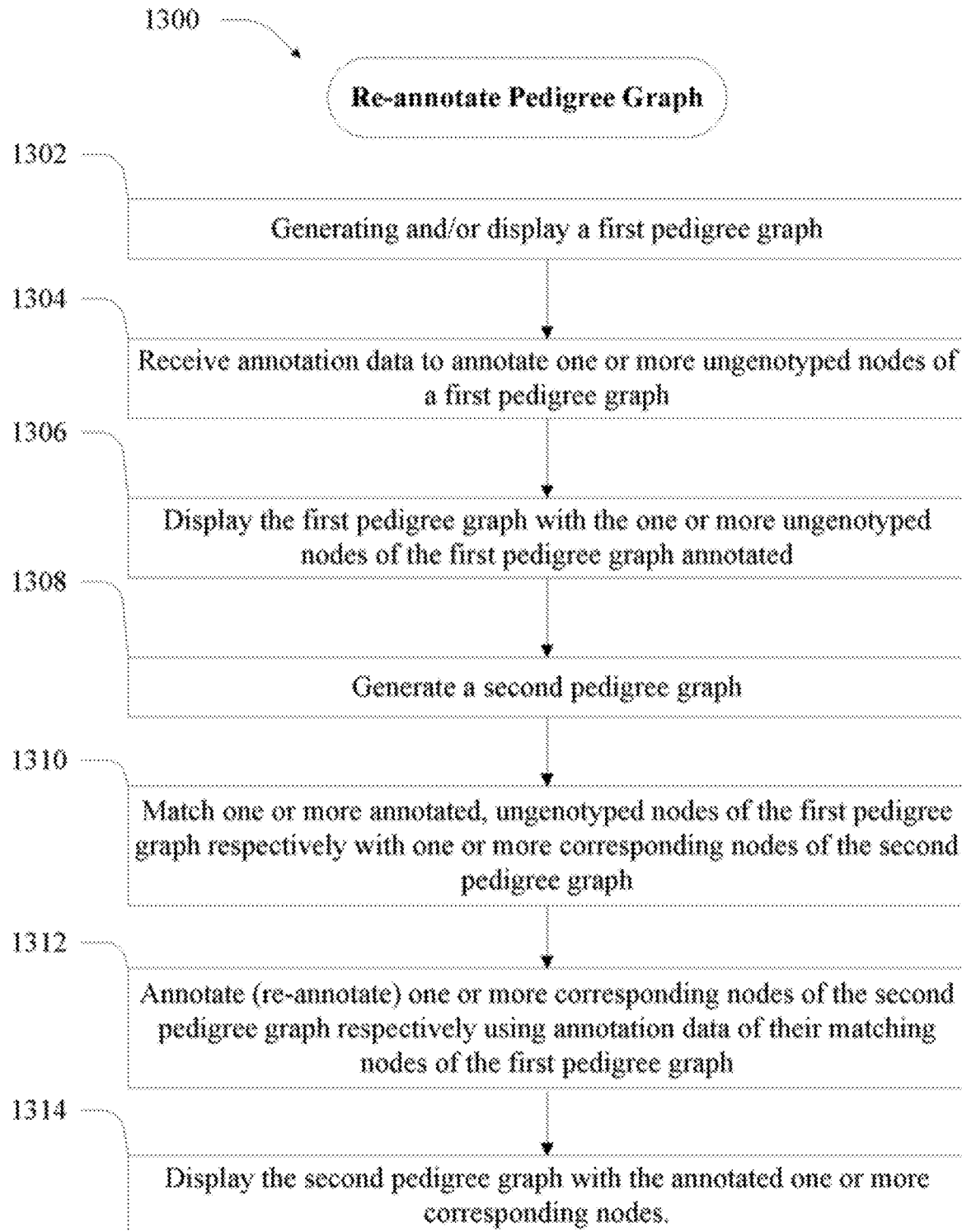
FIG. 25 shows a flowchart illustrating a process for re-annotating pedigree graphs according to some implementations.

FIG. 25 shows a flowchart illustrating process 1300 for re-annotating pedigree graphs. Process 1300 involves generating and/or displaying a first pedigree graph. See box 1302. The first pedigree graph in some implementations can be rendered as the graph displayed in FIG. 27. The first pedigree graph depicts relationships among a first plurality of individuals. It includes a plurality of genotyped nodes and one or more un-genotyped nodes. Each node represents an individual. Each genotyped node represents an individual whose genetic data have been used to determine the pedigree relationships depicted by the pedigree graph. Each ungenotyped node represents an individual whose genetic data have not been used to determine the pedigree relationships depicted by the pedigree graph. The ungenotyped individual is inferred from the pedigree relationships determined from genetic data.

Process 1300 also involves receiving annotation data to annotate one or more un-genotyped nodes of the first pedigree graph. See box 1304. Process 1300 also involves displaying the first pedigree graph with the one or more un-genotyped nodes annotated. See box 1306.

Figure 28:
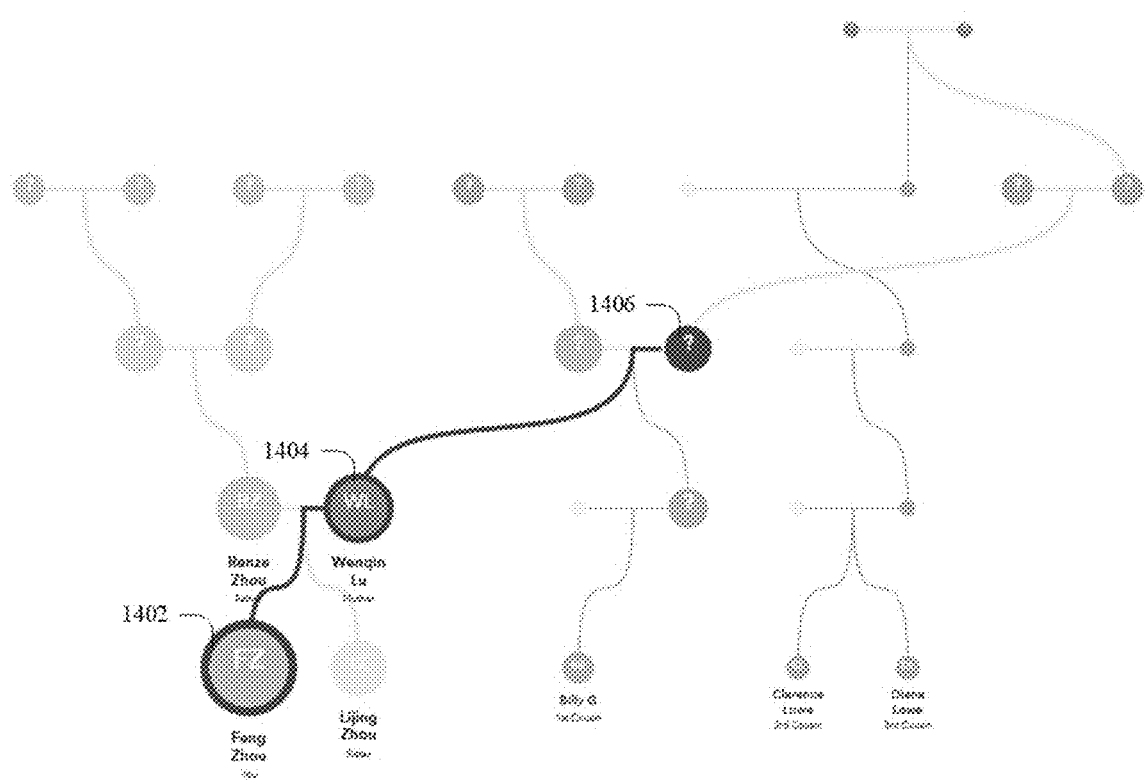
FIG. 28 shows an example implementation of displaying a pedigree graph and receiving user input for annotating un-genotyped nodes of the pedigree graph.

FIGS. 27-30 show example implementations of displaying a pedigree graph and receiving user input for annotating un-genotyped nodes of the pedigree graph. A user may provide user input to annotate any one of the ungenotyped nodes. FIG. 28 shows that in some implementations, the user may select an ungenotyped node 1406 in a graphical user interface. After the ungenotyped node 1406 is selected, some implementations automatically highlight the focal node, the selected node and intermediate nodes through which the first two are related. In this example, when grandparent node 1406 is selected, focal node 1402, parent node 1404, and grandparent node 1406 are highlighted.

Figure 29:
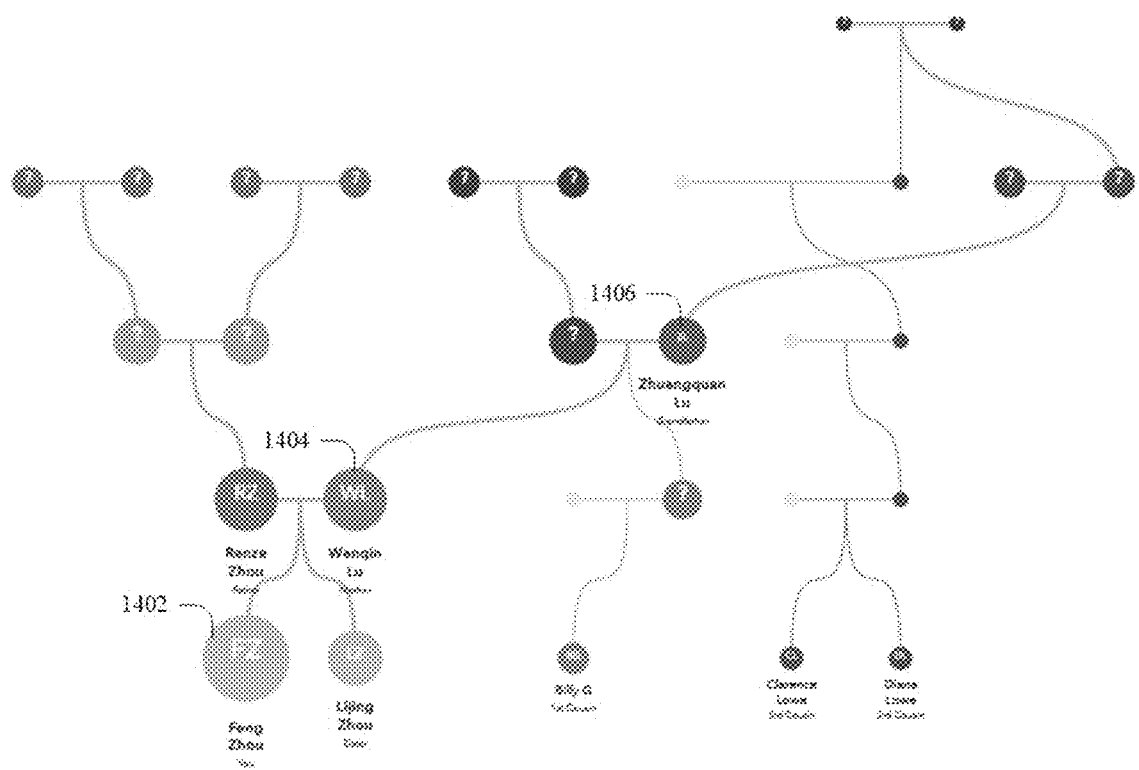
FIG. 29 shows an example implementation of displaying a pedigree graph and receiving user input for annotating un-genotyped nodes of the pedigree graph.

After annotation data are provided by the user, the first pedigree graph is displayed with grandparent node 1406 annotated as shown in FIG. 29. The annotation shown here includes the name of the grandparent and an indication that the grandparent is a grandfather (e.g., based on gender information). In some implementations, the annotation data can be provided through a graphical user interface such as the one shown in FIG. 30.

Returning to FIG. 25, process 1300 further involves generating a second pedigree graph. See box 1308. The second pedigree graph also includes a plurality of genotyped nodes and one or more ungenotyped nodes. The individuals represented by the first pedigree graph and the second pedigree graph overlap.

Process 1300 further involves matching one or more annotated, ungenotyped nodes of the first pedigree graph respectively with one or more corresponding nodes of the second pedigree graph. See box 1310. Process 1300 involves annotating one or more corresponding nodes of the second pedigree graph respectively using annotation data of their matching nodes of the first pedigree graph. This annotation can be referred to as re-annotating nodes in a second pedigree graph using annotation data of corresponding nodes in the first pedigree graph. See box 1312.

Figure 31:
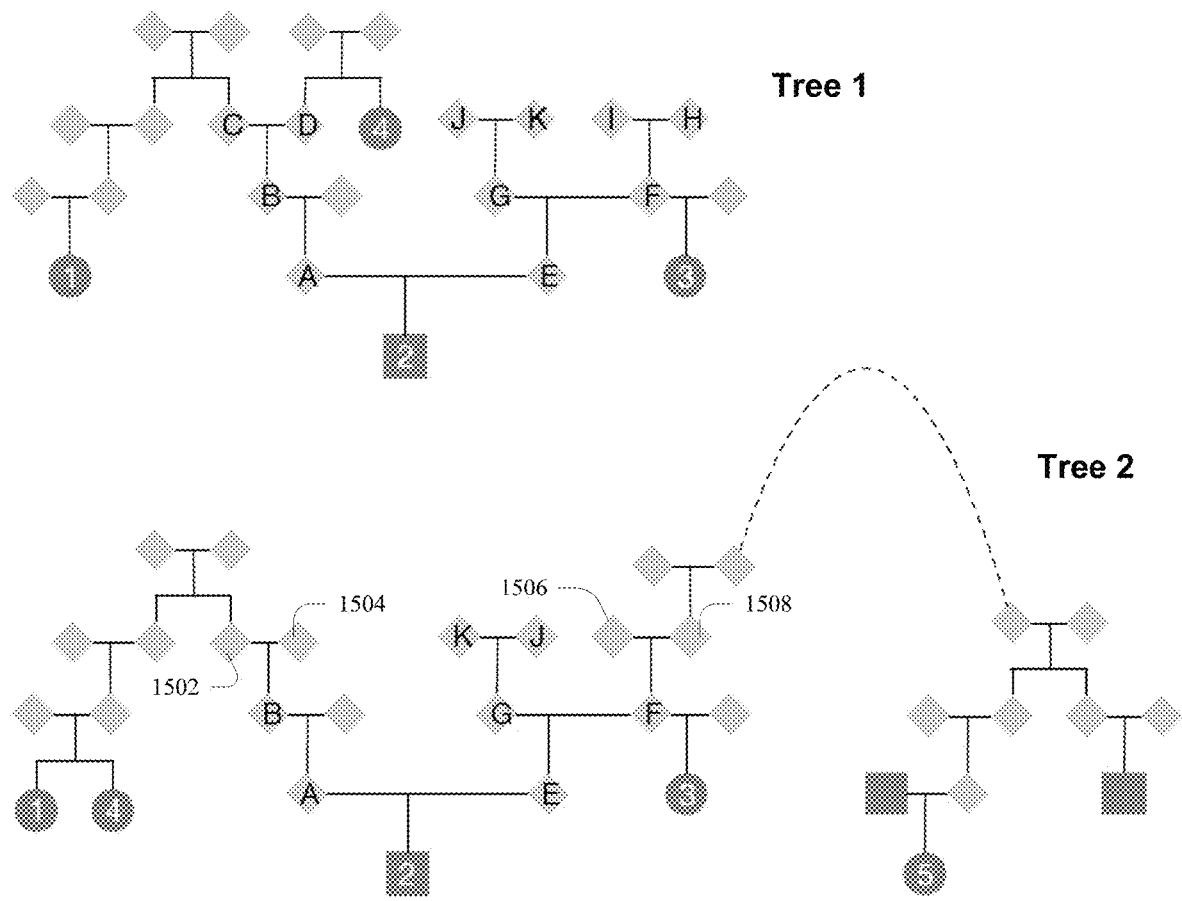
FIG. 31 shows an example of a first pedigree graph and a second pedigree graph respectively labeled as Tree 1 and Tree 2, illustrating how ungenotyped nodes can be matched according to some implementations.

Process 1300 further involves displaying the second pedigree graph with the annotated one or more corresponding nodes. See box 1314. FIG. 31 includes a pedigree graph labeled as "Tree 2," which is an example of a second pedigree graph with one or more genotyped nodes annotated using annotation data from corresponding nodes in a first pedigree graph labeled as "Tree 1." Tree 2 includes a branch with node 5 that is not in Tree 1.

Figure 26:
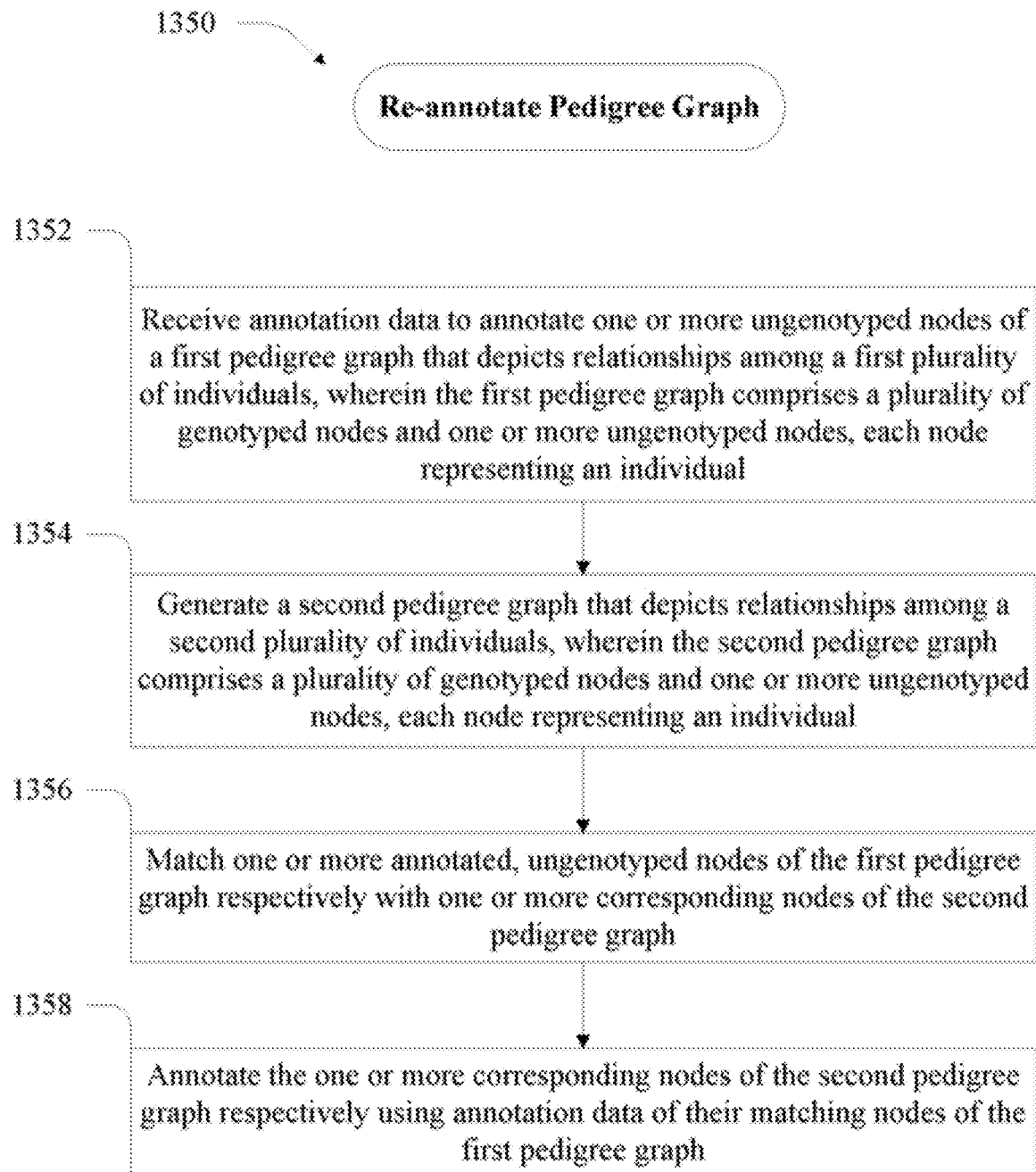
FIG. 26 illustrates another process for re-annotating pedigree graph according to some implementations.

FIG. 26 illustrates process 1350 for re-annotating pedigree graph. Process 1350 includes a subset of steps of process 1300. The operations illustrated in boxes 1352, 1354, 1356, and 1358 of process 1350 correspond to operations in boxes 1304, 1308, 1310, and 1312 in process 1300 in FIG. 25. Process 1350 includes further details and limitations than process 1300.

Process 1350 for re-annotating pedigree graph involves receiving annotation data to annotate one or more ungenotyped nodes of the first pedigree graph that depicts relationships among a first plurality of individuals. See box 1352. In some implementations, the annotation data include name, maiden name, gender, date of birth, year of birth, place of birth, ethnicity, living or deceased state, date of birth, date of death, place of death, and/or photographic data.

The first pedigree graph includes a plurality of genotyped nodes and one or more ungenotyped nodes, each node representing an individual. The genotyped node represents an individual whose genetic data have been used to determine the pedigree relationships depicted by the pedigree graph. An ungenotyped node represents an individual whose genetic data have not been used to determine the pedigree relationships depicted by the pedigree graph.

In some implementations, the first pedigree graph is displayed before annotation data is received. The annotation data may be provided by the user with reference to the displayed first pedigree graph.

An example of the first pedigree graph is shown in FIG. 31 as Tree 1 in the top half of the figure. In this example, genotyped nodes are labeled by numbers and rendered as squares or circles. Ungenotyped nodes are rendered as diamonds. The ungenotyped nodes that are annotated are labeled with capital letters.

Process 1350 also involves generating a second pedigree graph that depicts relationships among the second plurality of individuals. The second pedigree graph includes a plurality of genotyped nodes and one or more ungenotyped nodes, each node representing an individual. See box 1354. In some implementations, the second plurality of individuals includes at least one individual who is not among the first plurality of individuals. In other implementations, the first plurality of individuals includes at least one individual who is not among the second plurality of individuals. In various implementations, the first plurality of individuals and the second plurality of individuals overlap. In some implementations, the second plurality of individuals is identical to the first plurality of individuals, but the relationships among the second plurality of individuals are not identical to the relationships among the first plurality of individuals.

Process 1350 also involves matching one or more annotated, ungenotyped nodes of the first pedigree graph respectively with one or more corresponding nodes of the second pedigree graph. See box 1356.

Process 1350 further involves annotating the one or more corresponding nodes of the second pedigree graph respectively using annotation data of their matching nodes of the first pedigree graph. See box 1358. In some implementations, the process further involves displaying the annotated second pedigree graph using a display device.

In some implementations, matching nodes of the first pedigree graph with nodes of the second pedigree graph includes the steps in the following pedigree matching procedure:

Procedure (Pedigree Matching).
1. Determine that an individual N in the first pedigree graph matches an individual N in the second pedigree graph;
2. identify, among individuals represented by genotyped nodes in the first pedigree graph, relatives of P(1, 1, N) and relatives of P(1, 2, N), wherein P(1, 1, N) is in the first pedigree graph a first parent of N, P(1, 2, N) is in the first pedigree graph a second parent of N, and the relatives are biologically related and exclude any common direct descendants;
3. identify, among individuals represented by genotyped nodes in the second pedigree graph, relatives of P(2, 1, N) and relatives of P(2, 2, N), wherein P(2, 1, N) is in the second pedigree graph a first parent of N, and P(2, 2, N) is in the second pedigree graph a second parent of N, and the relatives are biologically related and exclude any common direct descendants; and
4. a) match node P(1, 1, N) with node P(2, 1, N) or P(2, 2, N) when matching conditions are met, wherein the matching conditions comprise: any identified relatives of P(1, 1, N) are also identified relatives of P(2, 1, N) or P(2, 2, N) respectively, or
b) match node P(1, 1, N) with either node P(2, 1, N) or node P(2, 2, N) when P(1, 1, N), P(1, 2, N), P(2, 1, N) and P(2, 2, N) all have zero identified relatives.

In some implementations, one or more of the following must be met for matching a parent P(1, 1, N) of N on Tree 1 to a parent P(2, 1, N) of N on Tree 2. In some implementations, all of the following must be met to match.

Conditions (Pedigree Matching).
1. Any identified relative of P(1, 1, N) appearing on both trees is also an identified relative of P(2, 1, N);
2. any identified relative of P(1, 2, N) appearing on both trees is also an identified relative of P(2, 2, N);
3. no identified relative of P(1, 1, N) is also an identified relative of P(2, 2, N);
4. no identified relative of P(1, 2, N) is also an identified relative of P(2, 1, N);
5. all shared identified descendants of P(1, 1, N) and P(2, 1, N) have the same degrees of relationship to P(1, 1, N) and P(2, 1, N);
6. all shared identified descendants of P(1, 2, N) and P(2, 2, N) have the same degrees of relationship to P(1, 2, N) and P(2, 2, N);
7. P(1, 1, N) and P(2, 1, N) have at least one common identified relative, or P(1, 2, N) and P(2, 2, N) have at least one common identified relative, or P(1,1, N), P(1, 2, N), P(2, 1, N), and P(2, 2, N) have no identified relatives.

In some implementations, the matching conditions further include: each identified relative of P(1, 1, N) who is also an identified relative of P(2, 1, N) or P(2, 2, N) has a same category of relationships with P(1, 1, N) and P(1, 2, N) or P(1, 1, N) and P(2, 2, N) respectively.

In some implementations, each category of relationship is selected from: direct ancestor relationships, direct descendant relationships, and other relationships. In some implementations, each category of relationships corresponds to a degree of relationship or similar degrees of relationships.

In some implementations, a data structure with a relationship dictionary is used to store the relatives of each node of interest, as well as relationships, relationship types, relationship degrees, or relationship categories of the relatives. By querying the dictionary, all relatives of an individual of interest can be determined. In some implementations, the relationship dictionary groups relationships of relatives into three categories: ancestors, descendants, and other relatives. In some implementations, relatives who are related through only marriage are excluded.

In some implementations, both the first pedigree graph and the second pedigree graph include a genotyped node representing a same focal individual, and the individual N is the focal individual.

In some implementations, matching nodes includes repeating steps 1-4 of the pedigree matching procedure one or more times using the matched P(1, 1, N) and P(2, 1, N) in step 4 as the individual N in step 1.

In some implementations, matching nodes further includes, when matching conditions are not met in step 4 of the pedigree matching procedure, repeating steps 1-4 of the pedigree matching procedure using an individual represented by a genotyped node whose parents have not been matched.

In some implementations, matching nodes further includes, matching a first node on the first pedigree graph with a second node on the second pedigree graph when the partner node of the first node and the partner node of the second node are matched. The partner node of the first node and the partner node of the second node can be matched based on the matching conditions. They can also be matched because they correspond to a same genotyped individual in the database.

A matching process can start by selecting a focal node 2 on both Tree 1 and Tree 2 corresponding to a same focal person that was genotyped. The same genotyped data of the person for the two nodes indicate that the two nodes represent the same individual. The matching process identifies all relatives of node A (a first parent of node 2) of Tree 1, which include node 1 and node 4. The relatives are biologically related and exclude any common direct descendants. The matching process also identifies all relatives of node A (a first parent of node 2) of Tree 2, which include node 1 and node 4. Therefore, pedigree matching conditions 1 and 7 are satisfied.

Moreover, the relatives of E in Tree 1 are node 3, and the relatives of node E in Tree 2 are node 3 and node 5. No relative of node A in Tree 1 (1, 4) is also a relative of node E in Tree 2 (3, 5). Similarly, no relatives of node E in Tree 1 (3) is also a relative of node A in Tree 2 (1, 4). As such, pedigree matching conditions 2, 3, and 4 are satisfied.

Finally, on both Tree 1 and Tree 2, the only descendant of A and E is node 2. As such, pedigree matching conditions 5 and 6 are satisfied. Therefore, because all pedigree matching conditions are satisfied, node A of Tree 1 is matched with node A of Tree 2.

In some implementations, the process matches a first node on the first pedigree graph with a second node on the second pedigree graph when the partner nodes of the first and second nodes are matched. In this example, when the partner of node E in Tree 1 (node A) is matched with the partner of node E in Tree 2 (node A), node E in Tree 1 is also matched with node E of Tree 2.

The matching process in some implementations proceeds to use node A as the focal node and identify the relatives of node B and its partner node as two parent nodes of node A. Because relatives of node B in Tree 1 (1, 4) are also relatives of node B in Tree 2 (1,4), pedigree matching conditions 1 and 7 are satisfied. Because the partner of B has no relatives in either Tree 1 or Tree 2, pedigree matching condition 2 is satisfied. Because no relatives of node B in Tree 1 (1, 4) are also relatives of node B's partner in Tree 2 (none), pedigree matching condition 3 is satisfied. Because no relatives of node B's partner in Tree 1 (none) are also relatives of node B in Tree 2 (1,4), pedigree matching condition 4 is satisfied. Finally, because B and their partner have the same descendants (A and 2) in both Tree 1 and Tree 2, and because the relationships between these descendants and B and B's partner are the same in both trees, pedigree matching conditions 5 and 6 are satisfied. Therefore, node B of Tree 1 is matched with node B of Tree 2.

The matching process in some implementations proceeds to use node B as the focal node and identify the relatives of node C and node D as two parent nodes of node B in Tree 1 and node 1502 and node 1504 as two parent nodes of node B in Tree 2. Because a relative of node C in Tree 1 (1) is one of the relatives of node 1502 in Tree 2 (1,4), pedigree matching condition 7 is satisfied. Because no relative of node C in Tree 1 (1) is also a relative of node 1504 in Tree 2 (none), pedigree matching condition 3 is satisfied. However, because a relative of node D in Tree 1 (4) is also one of the relatives of node 1502 in Tree 2 (1,4), pedigree matching condition 4 is not satisfied. Therefore, node C of Tree 1 cannot be matched with node 1502 of Tree 2. Similarly, node D of Tree 1 cannot be matched with node 1502 of Tree 2. Also, neither node C nor node D of Tree 1 cannot be matched with node 1504 of Tree 2. Therefore, node C and node D of Tree 1 cannot be matched with any nodes of Tree 2.

The matching process in some implementations proceeds to use node E as the focal node and identify node G and node F as two parent nodes of node E. Because the relatives of node G in Tree 1 (none) and the relatives of node G in Tree 2 (none) are the same, pedigree matching condition 1 is satisfied. Because the relative of node F in Tree 1 (3) is also one of the relatives of node F in Tree 2 (3,5), pedigree matching conditions 2 and 7 are satisfied. Because no relatives of node F in Tree 1 (3) are also relatives of node G in Tree 2 (none), pedigree matching condition 3 is satisfied. Moreover, because no relatives of node G in Tree 1 (none) are also the relatives of node F in Tree 2 (3,5), pedigree matching condition 4 is satisfied. Finally, because E and 2 are the only descendants of F and G in both Tree 1 and Tree 2, and because these descendants have the same degrees of relationship to F and G in both trees, pedigree matching conditions 5 and 6 are satisfied. Therefore, node F of Tree 1 is matched with node F of Tree 2. Also, their partner nodes, node G on Tree 1 and node G on Tree 2 are matched.

In some implementations, when two parent nodes in Tree 1 and two parent nodes in Tree 2 all have zero relatives, either parent node in Tree 1 can be matched to either parent node of Tree 2. In these implementations, node J and node K in Tree 1 and node J and node K in Tree 2 all have zero relatives. Note that node 2 is not a relative, because it is a common descendant that is excluded. Moreover, the identified descendants of J and K are 2, E, and G and these descendants have the same degrees to J and K in both Tree 1 and Tree 2. Thus, all criteria are satisfied and either node J or node K in Tree 1 can be matched to either node J or node K in Tree 2.

However, node I and node H in Tree 1 cannot be matched to nodes 1506 or node 1508 in Tree 2, because node I and node H in Tree 1 have no relatives, but 1509 in Tree 2 has relative node 5. Therefore, pedigree matching condition 7 is not satisfied.

Pseudocode for matching nodes on two pedigree graphs for reannotation is provided below.

Apparatus and Systems

Figure 17:
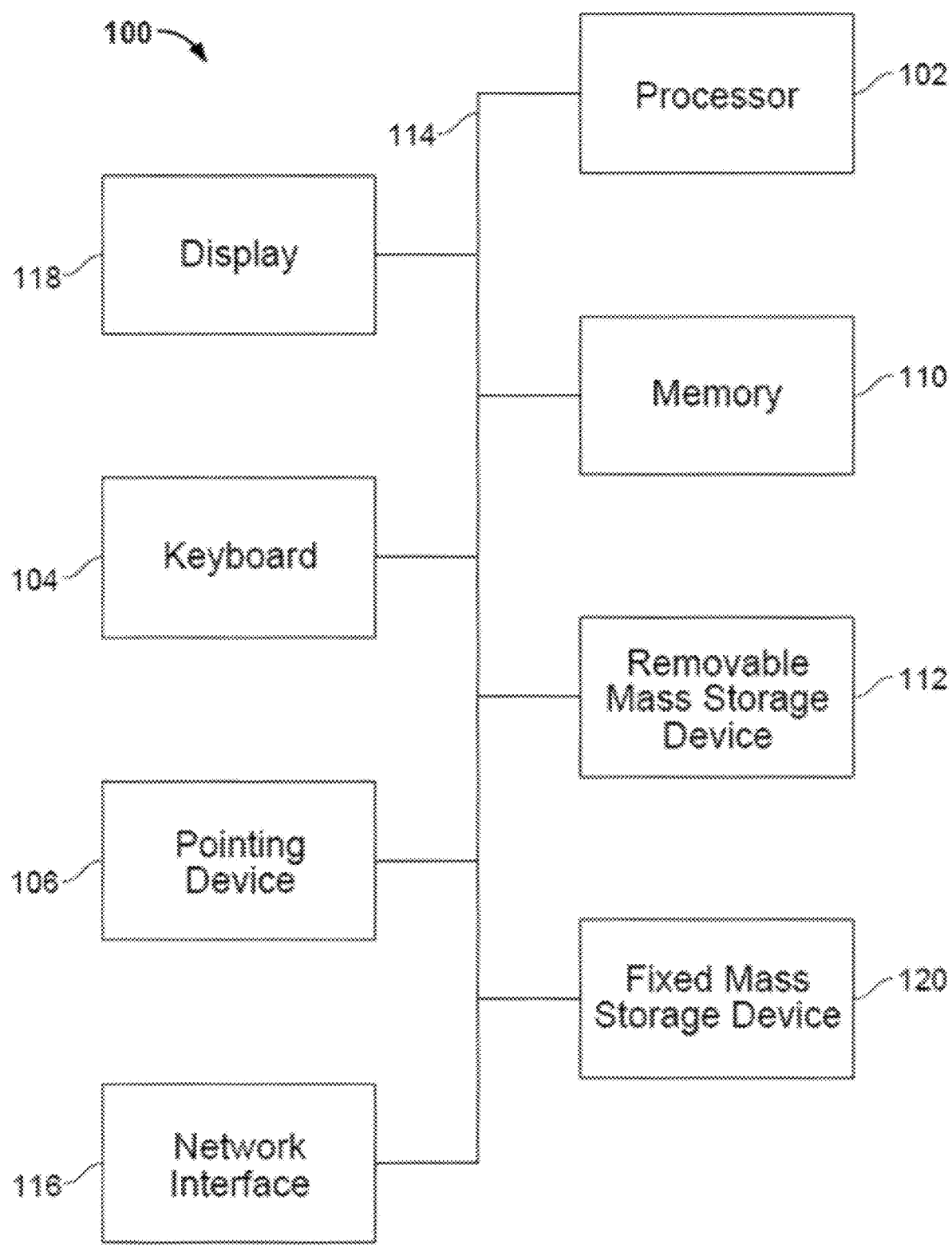
FIG. 17 shows a functional diagram illustrating a programmed computer system for performing processes for determining or displaying pedigrees in accordance with some implementations.

FIG. 17 is a functional diagram illustrating a programmed computer system for performing processes for determining or displaying pedigrees in accordance with some implementations. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some implementations, processor 102 is a general purpose digital processor that controls the operation of the computer system 100. Using instructions retrieved from memory 110, the processor 102 controls the reception and manipulation of input data, and the output and display of data on output devices (e.g., display 118). In some implementations, processor 102 includes and/or is used to provide IBD determination, pedigree determination, pedigree drawing and displaying, etc. as described herein.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and

--- if $i_1$ or $i_2$ was inferred to be un-matchable on a previous step then
    Return
end if
$p_{1,1}, p_{1,2}$ = Get parent ids of $i_1$ in pedigree 1
$p_{2,1}, p_{2,2}$ = Get parent ids of $i_2$ in pedigree 2
relSet($p_{1,1}$) = Get non-descendant relatives of parent 1 of $i_1$
relSet($p_{1,2}$) = Get non-descendant relatives of parent 2 of $i_1$
relSet($p_{2,1}$) = Get non-descendant relatives of parent 1 of $i_2$
relSet($p_{2,2}$) = Get non-descendant relatives of parent 2 of $i_2$
descSet($p_{1,1}$) = Get descendants of parent 1 of $i_1$
descSet($p_{1,2}$) = Get descendants of parent 2 of $i_1$
descSet($p_{2,1}$) = Get descendants of parent 1 of $i_2$
descSet($p_{1,2}$) = Get descendants of parent 2 of $i_2$
relCheck($p_{1,1}, p_{2,1}$) = Check conditions 1-4 and 7 of the pedigree matching conditions for matching parent 1 of $i_1$ and parent 1 of $i_2$
relCheck($p_{1,2}, p_{2,1}$) = Check conditions 1-4 and 7 of the pedigree matching conditions for matching parent 2 of $i_1$ and parent 1 of $i_2$
descCheck($p_{1,1}, p_{2,1}$) = Check conditions 5 and 6 of the pedigree matching conditions for matching parent 1 of $i_1$ and parent 1 of $i_2$
descCheck($p_{1,2}, p_{2,1}$) = Check conditions 5 and 6 of the pedigree matching conditions for matching parent 2 of $i_1$ and parent 1 of $i_2$
Initialize empty list matchedPairList
if relCheck($p_{1,1}, p_{2,1}$) and descCheck($p_{1,1}, p_{2,1}$) then
    Map $p_{1,1}$ to $p_{2,1}$ and map $p_{1,2}$ to $p_{2,2}$
    Append the tuples ($p_{1,1}, p_{2,1}$) and ($p_{1,2}, p_{2,2}$) to matchedPairList
else if relCheck($p_{1,2}, p_{2,1}$) and descCheck($p_{1,2}, p_{2,1}$) then
    Map to $p_{2,1}$ and map to $p_{2,2}$
    Append the tuples ($p_{1,2}, p_{2,1}$) and ($p_{1,1}, p_{2,2}$) to matchedPairList
else
    Add $p_{1,1}$ and $p_{1,2}$ to mismatch set 1
    Add $p_{2,1}$ and $p_{2,2}$ to mismatch set 2
end if
for ($i_1, i_2$) in matchedPairList do
    Recursively match the parents of $i_1$ the parents of $i_2$
end for

--- data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer-readable storage media, described below, depending on whether, for example, data access needs to be bi-directional or uni-directional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process implementations disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various implementations disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 17 is but an example of a computer system suitable for use with the various implementations disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 18:
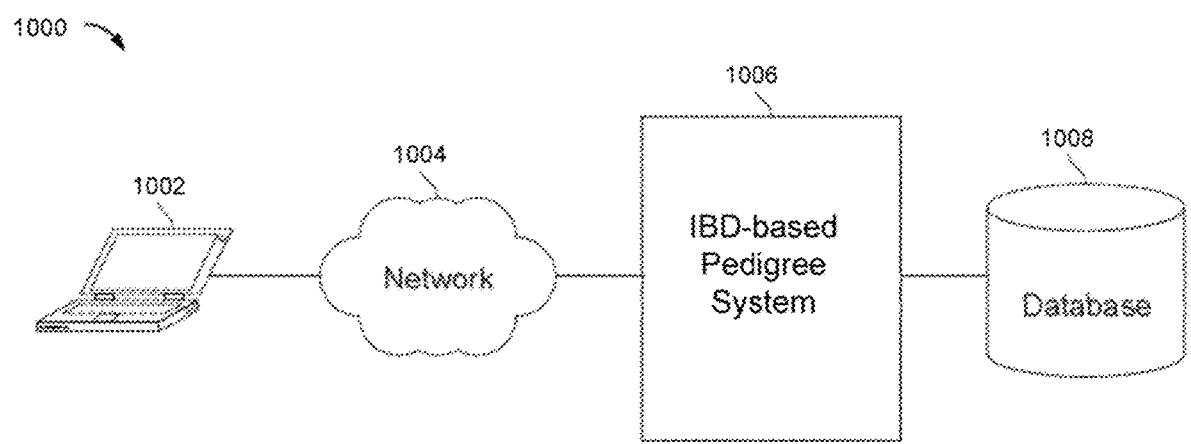
FIG. 18 shows a block diagram illustrating an implementation of an IBD-based pedigree determination and display system.

FIG. 18 is a block diagram illustrating an implementation of an IBD-based pedigree services system that provides services based on IBD information, which include but are not limited to relatedness estimation, relative detection, pedigree determination, combination, drawing and display. In this example, a user uses a client device 202 to communicate with an IBD-based pedigree services system 206 via a network 204. Examples of device 202 include a laptop computer, a desktop computer, a smart phone, a mobile device, a tablet device or any other computing device. IBD-based personal genomics services system 206 is used to perform a pipelined process to determine and or display pedigrees based on users IBD information. IBD-based pedigree services system 206 can be implemented on a networked platform (e.g., a server or cloud-based platform, a peer-to-peer platform, etc.) that supports various applications. For example, implementations of the platform perform pedigree determination or display and provide users with access (e.g., via appropriate user interfaces) to their personal genetic information (e.g., genetic sequence information and/or genotype information obtained by assaying genetic materials such as blood or saliva samples) and predicted ancestry information. In some implementations, the platform also allows users to connect with each other and share information. Device 100 can be used to implement 202 or 206.

In some implementations, DNA samples (e.g., saliva, blood, etc.) are collected from genotyped individuals and analyzed using DNA microarray or other appropriate techniques. The genotype information is obtained (e.g., from genotyping chips directly or from genotyping services that provide assayed results) and stored in database 208 and is used by system 206 to make ancestry predictions or pedigree determination. Reference data, including genotype data of reference individuals, simulated data (e.g., results of machine-based processes that simulate biological processes such as recombination of parents' DNA), pre-computed data (e.g., a precomputed reference haplotype data used in phasing and model training) and the like can also be stored in database 208 or any other appropriate storage unit.

EXPERIMENTAL

Accuracy of the Likelihood and Generalized DRUID Estimators

This experiment shows the accuracy of the likelihood and generalized DRUID estimators (Equations 21 and 24) for inferring the degree of relationship between two distantly-related pedigrees.

Practitioners applied these estimators to infer the degree between common ancestors $A_1$ and $A_2$ of two small pedigrees $\mathcal{P}_1$ and $\mathcal{P}_2$. For this analysis, two identical small pedigrees $\mathcal{P}_1$ and $\mathcal{P}_2$ were simulated. Each small pedigree had the same topology comprised of the common ancestor $A_1$ or $A_2$, their spouse, their two children, and four grandchildren, where the grandchildren were comprised of two children for each child of $A_1$ or $A_2$. The ancestors $A_1$ and $A_2$ were then connected by degree d through a pair of common ancestors, where the degree d varied from 1 to 10.

Figure 6:
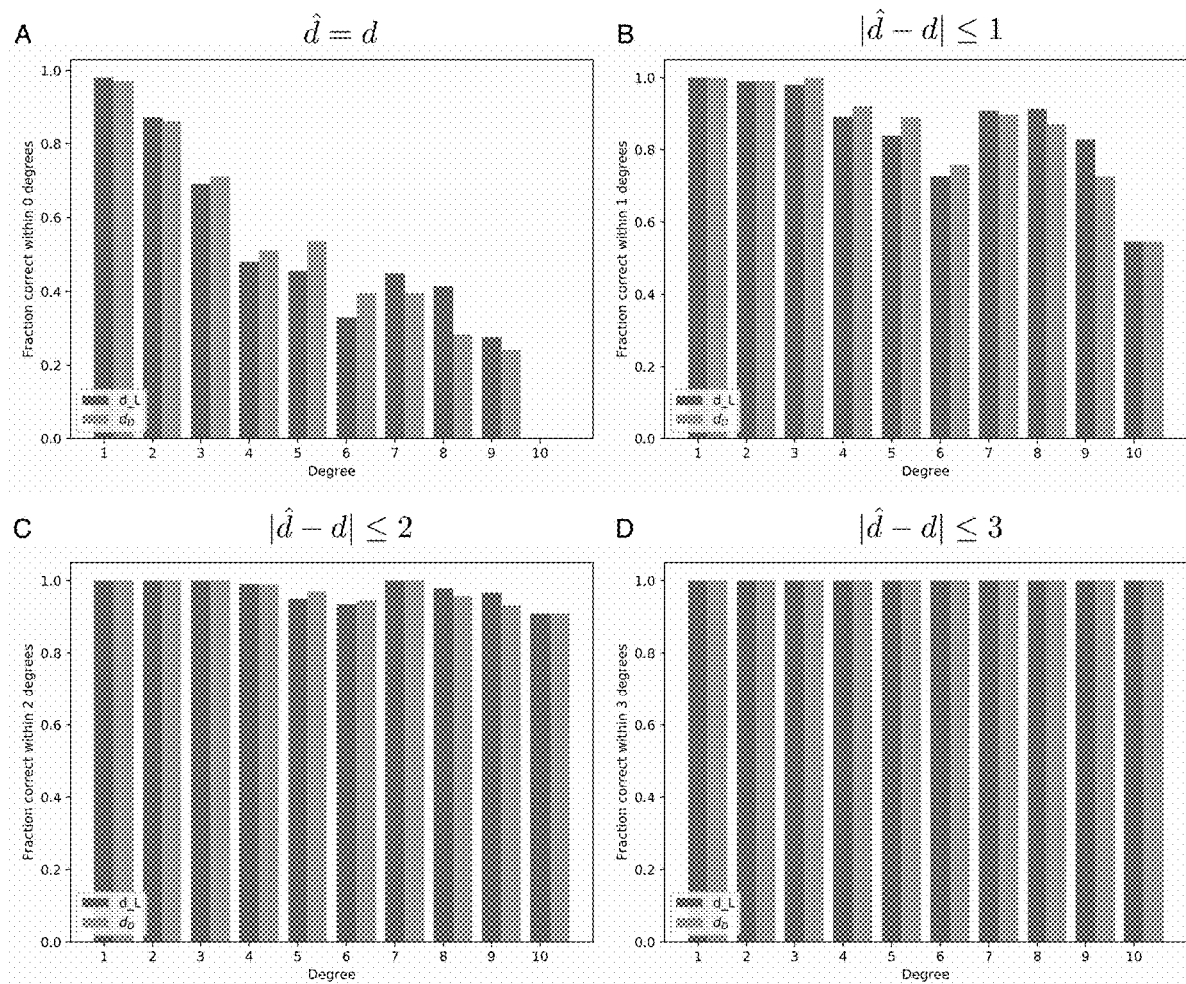
FIG. 6 includes data comparing pedigree estimates between a likelihood method (Equation 21) according to some implementations and a novel generalized version of the existing DRUID method (Equation 24). The figure shows that both the likelihood method and the generalized DRUID method perform accurately. Pedigrees were simulated in which two smaller pedigrees were connected by a path of degree d between their respective common ancestors. The accuracy of the methods for inferring degree d is shown for four different tolerances: (A) exactly equal to the true degree, (B) within one degree of the true degree, (C) within two degrees of the true degree, and (D) within three degrees of the true degree.

FIG. 6 shows the accuracy of the likelihood estimator $d_L$ (Equation 21) and the generalized DRUID estimator $d_D$ (Equation 24) for inferring the degree d, conditional on the event that any IBD at all is observed between the leaf nodes in $\mathcal{P}_1$ and $\mathcal{P}_2$. From FIG. 6 it can be seen that both the maximum likelihood estimator $d_L$ and the generalized DRUID estimator $d_D$ have similar accuracies for inferring the degree d. Moreover, the generalized DRUID estimate is nearly identical to the maximum likelihood estimate, which is important in practice because it implies that connecting two pedigrees through the degree inferred by DRUID results in a pedigree that is approximately the maximum likelihood pedigree. This result can dramatically speed up pedigree inference and, in practice, practitioners use the generalized DRUID estimator for inferring the degree of separation between two small pedigrees.

Accuracy and Runtime

This experiment compares accuracy and computer runtime between a computer implemented method referred to as Bonsai according to some implementation with a method based on the PRIMUS method.

The experiment is conducted to evaluate 204 pedigrees of 23andMe customers. Pedigrees were chosen in which each nuclear family had at least two genotyped offspring and two genotyped parents. Pedigrees spanned at least two generations.

To evaluate the accuracy of pedigree inference, practitioners subsampled these pedigrees, sampling 10, 20, 30, 40, or 50% of their members uniformly at random without replacement. The subsampled individuals were then used to reconstruct the pedigrees using PRIMUS and Bonsai.

Figure 19:
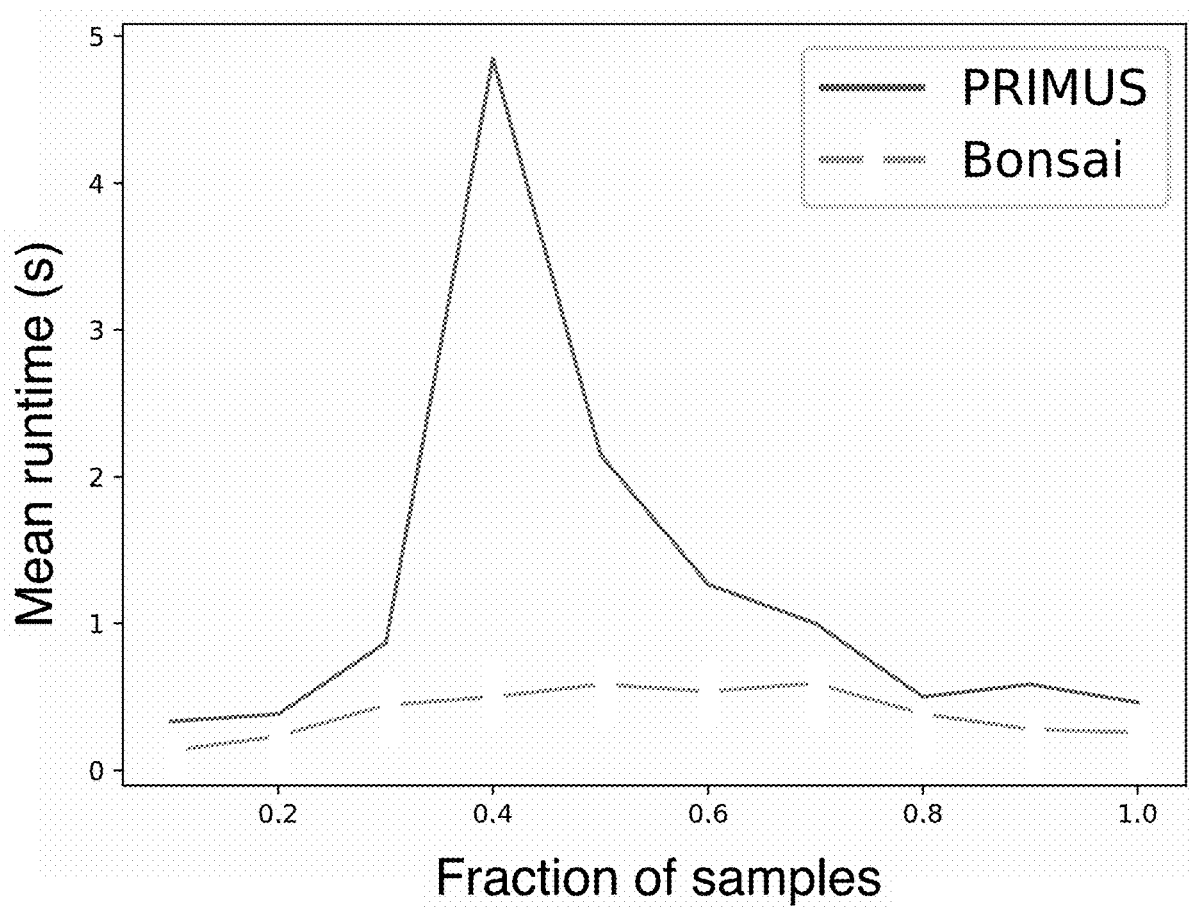
FIG. 19 shows results comparing computer runtime between a method according to some implementation and an existing method.
Figure 20:
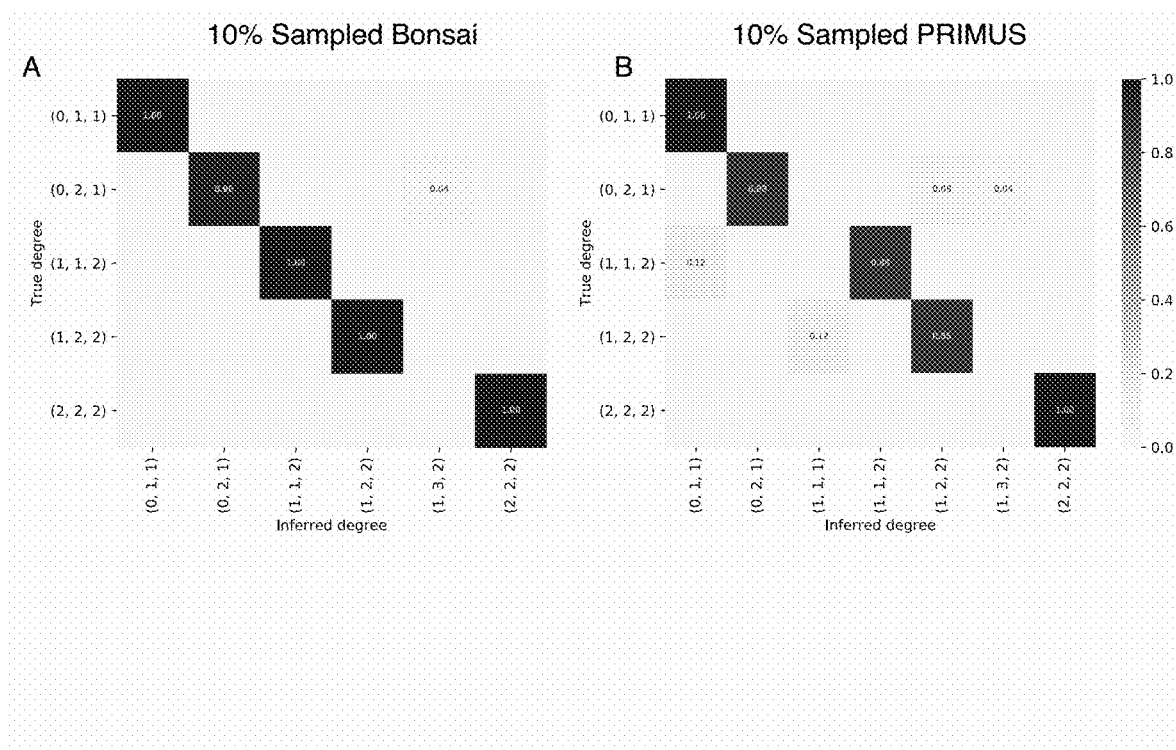
FIG. 20 shows accuracies of inferred relationships for pedigrees with 10 percent of individuals sampled according to some implementations and the existing method.
Figure 21:
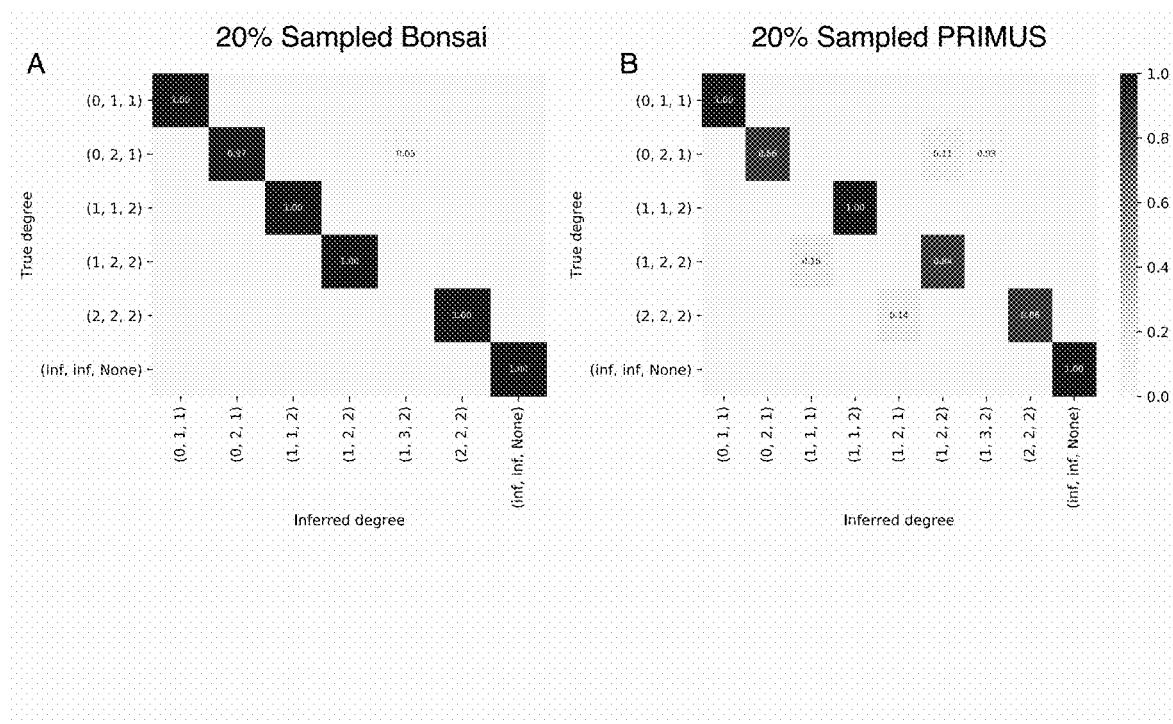
FIG. 21 shows accuracies of inferred relationships for pedigrees with 20 percent of individuals sampled according to some implementations and the existing method.
Figure 22:
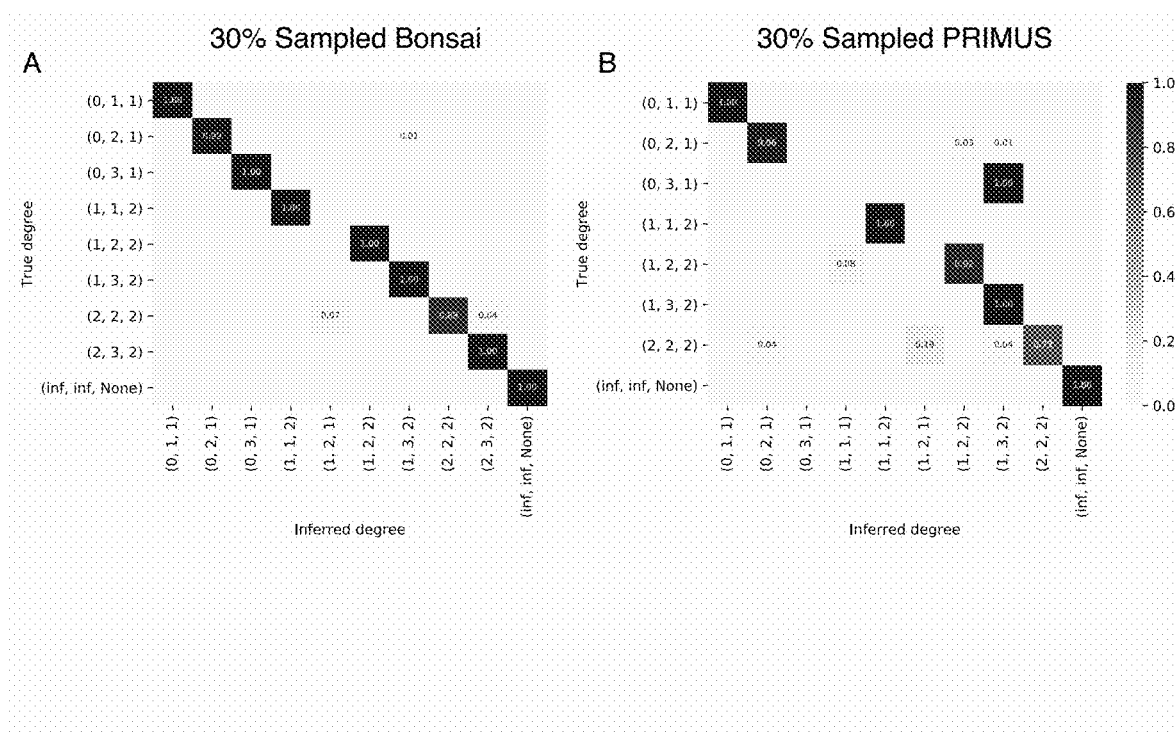
FIG. 22 shows accuracies of inferred relationships for pedigrees with 30 percent of individuals sampled according to some implementations and the existing method.
Figure 23:
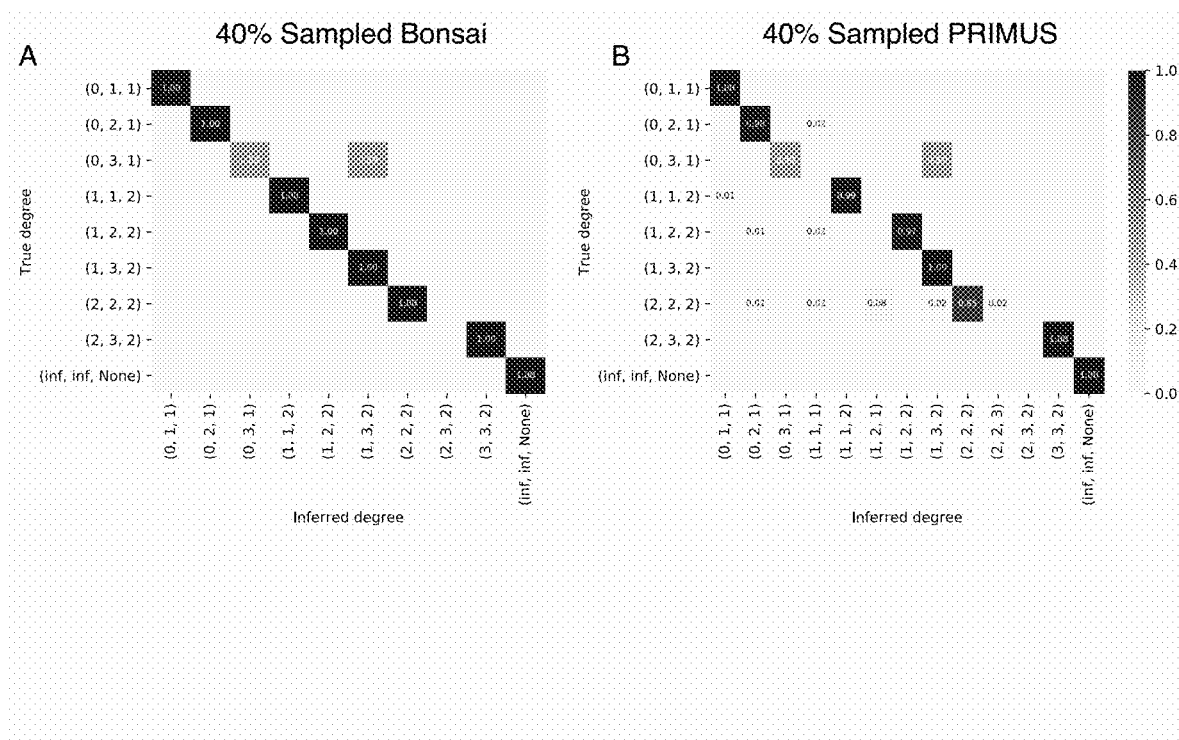
FIG. 23 shows accuracies of inferred relationships for pedigrees with 40 percent of individuals sampled according to some implementations and the existing method.
Figure 24:
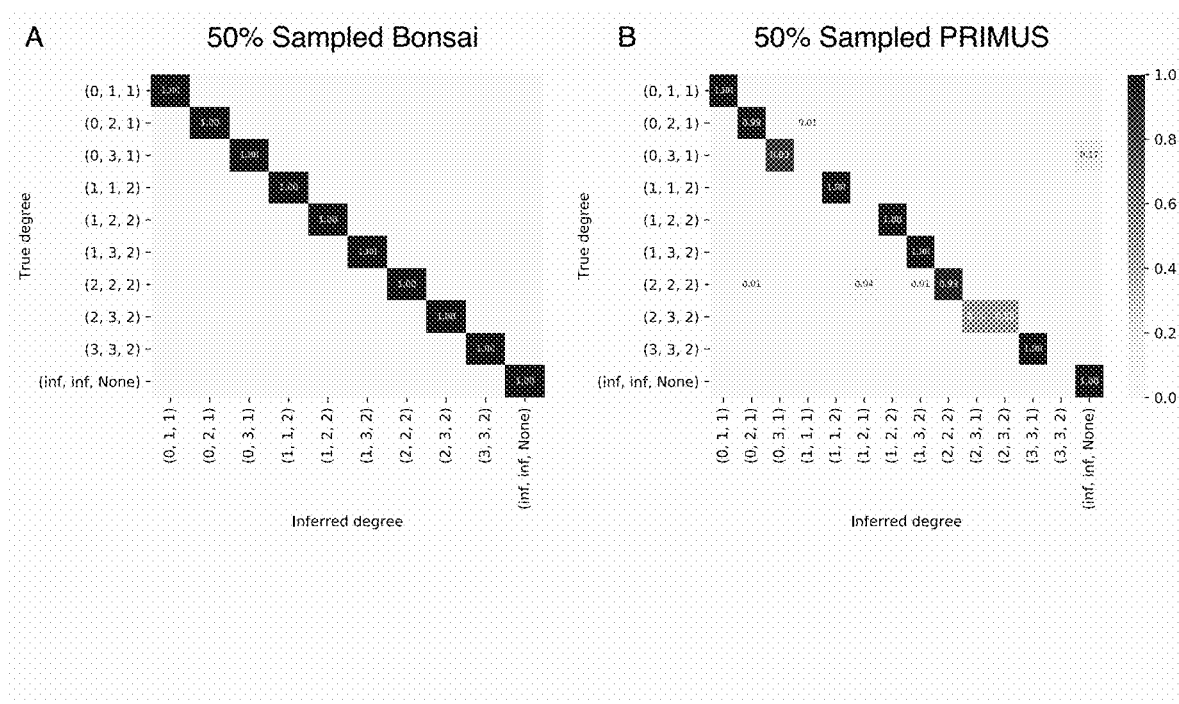
FIG. 24 shows accuracies of inferred relationships for pedigrees with 50 percent of individuals sampled according to some implementations and the existing method.

The Bonsai and PRIMUS methods were applied to exactly the same pedigree subsets. The x-axis in FIG. 19 is the fraction of sampled individuals in each of the 204 pedigrees that were used for pedigree inference. The y-axis is the average computer runtime in seconds required to reconstruct a pedigree. Bonsai is considerably faster than PRIMUS for pedigrees in which an intermediate number of individuals have been sampled.

Bonsai and PRIMUS have similar runtimes when few or many individuals are sampled because there are many fewer possible pedigrees to explore. This suggests that Bonsai gains considerable computational efficiency by ignoring very low likelihood pedigrees. The experiment illustrates that due to the computational efficiency of Bonsai, it runs faster on computers and conserves computer resources compared to prior art methods.

FIGS. 20-24 illustrate accuracies of Bonsai compared with PRIMUS, computed on 204 validated customer pedigrees in which all individuals were consented for research. Pedigrees were formed from quartets of individuals containing at least two genotyped offspring and two genotyped parents that could be used to triangulate and validate the other relationships in the quartet. Pedigrees spanned at least two generations, containing at least one pair of first cousins. Because pedigree inference becomes increasingly difficult as the fraction of sampled individuals in a pedigree decreases, we downsampled individuals in each pedigree to create sparse pedigrees in which relationships were known. We considered pedigrees in which 10, 20, 30, 40, and 50 percent of individuals were sampled. The subsampled individuals were then used to reconstruct the pedigrees using PRIMUS and Bonsai. The Bonsai and PRIMUS methods were applied to the same pedigree subsets and the same set of inferred pairwise likelihoods. FIG. 20A shows the accuracy of Bonsai for inferring different relationships when 10% of individuals were sampled from each pedigree. Tuples are of the form (up, down, number of ancestors) where up is the number of meioses from the first individual to their common ancestor(s) with the second, down is the number of meioses from the common ancestor(s) to the second individual, and the number of ancestors is the number of most recent common ancestors. The vertical axis indicates the true degrees of relationship, while the horizontal axis indicates the inferred degrees of the relationship. Different levels of shade indicate portions of a particular actual relationship determined by the model as various inferred relationships. Perfect predictions should have inferred relationships 100% on the identity line.

FIG. 20B shows the accuracy for PRIMUS applied to the same individuals with the same pairwise likelihoods as FIG. 20A. Comparing FIGS. 20A and 20B, one sees that Bonsai has more accurate predictions than PRIMUS when 10% of individuals are sampled.

Similarly, FIGS. 21-24 compare Bonsai with PRIMUS for increasingly large subsamples. Bonsai consistently has more accurate predictions than PRIMUS at different levels of sampling. When the fraction of sampled individuals was at least 50%, Bonsai had perfect accuracy, whereas PRIMUS continued to infer some relationships incorrectly.

What is claimed:

1. A method, implemented using a computer system that includes one or more processors and system memory, for training a probabilistic relationship model for predicting genetic relationships based on Identity-by-Descent (IBD) data and age data, the method comprising:
   a) receiving, by the computer system from a database, IBD data of a plurality of training sets for a plurality of relationships, wherein each training set comprises one or more pairs of individuals, each pair of individuals being genetically related with a same relationship, each training set is associated with a unique relationship, and the IBD data of each training set comprise pairwise IBD data of individuals in the training set;
   b) obtaining, by the computer system, age data of the plurality of training sets for the plurality of relationships, wherein the age data of each training set comprise pairwise age data of individuals in the training set; and
   c) training, by the computer system, the probabilistic relationship model using the IBD data of the plurality of training sets and the age data of the plurality of training sets, wherein the trained probabilistic relationship model is configured to take as input pairwise IBD data for two test individuals including a length of IBD segments and a number of IBD segments and pairwise age data for the two test individuals and provide as output various likelihoods of various potential relationships for the two test individuals, and wherein each likelihood of each potential relationship for the two individuals is a composite likelihood obtained by combining a likelihood given a length of IBD segment, a likelihood given a number of IBD segments, and a likelihood given an age difference between the two individuals.

2. The method of claim 1, further comprising:
   a) identifying, among the plurality of genetically related individuals, a closest relative of a starting individual using genetic data of the plurality of genetically related individuals;
   b) applying pairwise Identity-by-Descent (IBD) data and pairwise age data of the starting individual and the closest relative to a probabilistic relationship model to obtain various likelihoods of various potential relationships between the starting individual and the closest relative;
   c) selecting one or more potential relationships between the starting individual and the closest relative that have relationship likelihoods meeting a relationship criterion, and forming a pedigree from each of the one or more potential relationships;
   d) identifying, among genetically related individuals not included in pedigrees already formed, a closest relative of any individual already in a pedigree;
   e) applying pairwise IBD data and pairwise age data of the closest relative and the individual already in the pedigree to the probabilistic relationship model to obtain various likelihoods of various potential relationships between the closest relative and the individual already in the pedigree;
   f) selecting one or more potential relationships between the closest relative and the individual already in the pedigree that have relationship likelihoods meeting the relationship criterion, and adding each of the one or more potential relationships to each pedigree already formed to grow each pedigree into one or more growing pedigrees;
   g) selecting growing pedigrees that have pedigree likelihoods meeting a pedigree criterion as the pedigrees already formed; and
   h) repeating (1d)-(1g) one or more times,
   wherein (1a)-(1h) are performed by the computer system.

3. The method of claim 1, wherein the pairwise IBD data comprise a length of full IBD segments and/or a length of half IBD segments.

4. The method of claim 1, wherein the pairwise IBD data comprise a number of full IBD segments and/or a number of half IBD segments.

5. The method of claim 1, wherein the probabilistic relationship model is a machine-learning model.

6. The method of claim 1, wherein the probabilistic relationship model models a probability distribution of the pairwise IBD data for each relationship and/or a probability distribution of the pairwise age data for each relationship as a Gaussian distribution, a Poisson distribution, or an exponential distribution.

7. The method of claim 6, wherein training the probabilistic relationship model comprises using a method-of-moments technique to fit the probability distribution to training data.

8. The method of claim 1, wherein the plurality of relationships comprise relationships of the $4^{th}$, $5^{th}$, $6^{th}$, $7^{th}$, $8^{th}$, $9^{th}$, $10^{th}$, $11^{th}$, $12^{th}$, $13^{th}$, $14^{th}$ or $15^{th}$ degree or further.

9. The method of claim 1, wherein the various relationships comprise relationships of at least 4 meioses on a common-ancestor path.

10. The method of claim 1, wherein the various relationships comprise relationships having a coefficient of relationship smaller than 0.25.

11. The method of claim 1, wherein each training set comprises hundreds of individuals.

12. The method of claim 1, wherein each training set comprises thousands of individuals.

13. The method of claim 1, wherein each training set comprises tens of thousands of individuals.

14. The method of claim 1, wherein each training set comprises data of actual individuals.

15. The method of claim 1, wherein each training set comprises data of simulated individuals.

16. A system comprising one or more processors and one or more computer-readable storage media having stored thereon instructions, said one or more processors being configured to:
   a) receive, from a database, Identity-by-Descent (IBD) data of a plurality of training sets for a plurality of relationships, wherein each training set comprises one or more pairs of individuals, each pair of individuals being genetically related with a same relationship, each training set is associated with a unique relationship, and the IBD data of each training set comprise pairwise IBD data of individuals in the training set;

b) obtain age data of the plurality of training sets for the plurality of relationships, wherein the age data of each training set comprise pairwise age data of individuals in the training set; and c) train a probabilistic relationship model using the IBD data of the plurality of training sets and the age data of the plurality of training sets, wherein the trained probabilistic relationship model is configured to take as input pairwise IBD data for two test individuals including a length of IBD segments and a number of IBD segments and pairwise age data for the two test individuals and provide as output various likelihoods of various potential relationships for the two test individuals, and wherein each likelihood of each potential relationship for the two individuals is a composite likelihood obtained by combining a likelihood given a length of IBD segment, a likelihood given a number of IBD segments, and a likelihood given an age difference between the two individuals.

17. A computer program product comprising one or more computer-readable non-transitory storage media having stored thereon computer-executable instructions that, when executed by one or more processors of a computer system, cause the computer system to:

a) receive, from a database, Identity-by-Descent (IBD) data of a plurality of training sets for a plurality of relationships, wherein each training set comprises one or more pairs of individuals, each pair of individuals being genetically related with a same relationship, each training set is associated with a unique relationship, and the IBD data of each training set comprise pairwise IBD data of individuals in the training set;

b) obtain age data of the plurality of training sets for the plurality of relationships, wherein the age data of each training set comprise pairwise age data of individuals in the training set; and c) train a probabilistic relationship model using the IBD data of the plurality of training sets and the age data of the plurality of training sets, wherein the trained probabilistic relationship model is configured to take as input pairwise IBD data for two test individuals including a length of IBD segments and a number of IBD segments and pairwise age data for the two test individuals and provide as output various likelihoods of various potential relationships for the two test individuals, and wherein each likelihood of each potential relationship for the two individuals is a composite likelihood obtained by combining a likelihood given a length of IBD segment, a likelihood given a number of IBD segments, and a likelihood given an age difference between the two individuals.

\* \* \* \* \*